(12) United States Patent
Rapoport et al.

(10) Patent No.: US 11,278,461 B2
(45) Date of Patent: *Mar. 22, 2022

(54) DEVICES AND METHODS FOR A NEONATE INCUBATOR, CAPSULE AND CART

(71) Applicant: Aspect Imaging Ltd., Shoham (IL)

(72) Inventors: Uri Rapoport, Moshav Ben Shemen (IL); Shmuel Azulay, Tel Aviv (IL); Itzhak Rabinovitz, Ness Tsiyona (IL)

(73) Assignee: Aspect Imaging Ltd., Shoham (IL)

( * ) Notice: Subject to any disclaimer, the term of this patent is extended or adjusted under 35 U.S.C. 154(b) by 345 days.

This patent is subject to a terminal disclaimer.

(21) Appl. No.: 15/688,124

(22) Filed: Aug. 28, 2017

(65) Prior Publication Data

US 2019/0328596 A1 Oct. 31, 2019

Related U.S. Application Data

(63) Continuation-in-part of application No. 15/402,437, filed on Jan. 10, 2017, now Pat. No. 10,191,127, which is a continuation-in-part of application No. 13/903,057, filed on May 28, 2013, now Pat. No. 9,562,956, application No. 15/688,124, which is a continuation-in-part of application No. 15/367,839, filed on Dec. 2, 2016, now Pat. No. 10,499,830, which is a continuation-in-part of application No. 13/808,476, filed as application No.
(Continued)

(51) Int. Cl.
A61G 11/00 (2006.01)
A61B 50/13 (2016.01)
A61B 5/055 (2006.01)

(52) U.S. Cl.
CPC ............ *A61G 11/005* (2013.01); *A61B 5/055* (2013.01); *A61B 50/13* (2016.02); *A61G 11/009* (2013.01); *A61G 2203/46* (2013.01); *A61G 2203/80* (2013.01)

(58) Field of Classification Search
CPC ....... A61B 50/13; A61B 5/055; A61G 11/005; A61G 11/009
See application file for complete search history.

(56) References Cited

U.S. PATENT DOCUMENTS

| 1,900,342 A | 3/1933 | Hess |
| 2,638,087 A | 5/1953 | Livsey |

(Continued)

FOREIGN PATENT DOCUMENTS

| CA | 2815746 | 5/2012 |
| CN | 2448344 | 9/2001 |

(Continued)

OTHER PUBLICATIONS https://www.cdc.gov/growthcharts/html_charts/lenageinf.htm (Year: 2001).*

(Continued)

*Primary Examiner* — Dixomara Vargas
(74) *Attorney, Agent, or Firm* — Loeb & Loeb LLP

(57) ABSTRACT

Systems and method for positioning a neonate within an imaging device are provided. A capsule incubator, a cart, and a docking incubator are used to move a baby between an imaging device and a incubator, such that a baby can be imagined without having to move the baby from its environment.

6 Claims, 37 Drawing Sheets

Related U.S. Application Data

PCT/IL2011/000537 on Jul. 7, 2011, now abandoned, said application No. 15/367,839 is a continuation-in-part of application No. 14/892,207, filed as application No. PCT/IL2014/050450 on May 21, 2014, now Pat. No. 10,548,508.

(60) Provisional application No. 61/720,440, filed on Oct. 31, 2012, provisional application No. 61/361,936, filed on Jul. 7, 2010, provisional application No. 61/994,901, filed on May 18, 2014, provisional application No. 62/380,750, filed on Aug. 29, 2016, provisional application No. 62/380,758, filed on Aug. 29, 2016, provisional application No. 62/380,753, filed on Aug. 29, 2016, provisional application No. 62/381,079, filed on Aug. 30, 2016, provisional application No. 62/381,081, filed on Aug. 30, 2016, provisional application No. 62/380,768, filed on Aug. 29, 2016, provisional application No. 62/460,173, filed on Feb. 17, 2017, provisional application No. 62/471,672, filed on Mar. 15, 2017.

(56) References Cited

U.S. PATENT DOCUMENTS

| | | | |
|---|---|---|---|
| 2,708,927 | A | 5/1955 | Dixon et al. |
| 3,012,836 | A | 12/1961 | Smith et al. |
| 3,315,671 | A | 4/1967 | Creelman |
| 3,470,866 | A | 10/1969 | Gittelson |
| 3,534,251 | A | 10/1970 | Richards |
| 3,655,178 | A | 4/1972 | Vezina |
| 3,710,791 | A | 1/1973 | Deaton |
| 3,920,000 | A | 11/1975 | Atherton et al. |
| 4,008,388 | A | 2/1977 | McLafferty |
| 4,161,172 | A | 7/1979 | Pickering |
| 4,509,505 | A | 4/1985 | Mercey et al. |
| 4,543,959 | A | 10/1985 | Sepponen |
| 4,567,894 | A | 2/1986 | Bergman |
| 4,612,505 | A | 9/1986 | Zijlstra |
| 4,613,820 | A | 9/1986 | Edelstein |
| 4,698,611 | A | 10/1987 | Vermilyea |
| 4,712,263 | A | 12/1987 | Pronzinski |
| 4,715,073 | A | 12/1987 | Butler |
| 4,750,474 | A | 6/1988 | Dukhan et al. |
| 4,758,813 | A | 7/1988 | Holsinger |
| 4,875,485 | A | 10/1989 | Matsutani |
| 4,899,109 | A | 2/1990 | Tropp |
| 4,931,733 | A | 6/1990 | Hanawa |
| 4,936,824 | A | 6/1990 | Koch et al. |
| 4,937,454 | A | 6/1990 | Itoh |
| 4,968,961 | A | 11/1990 | Miyajima |
| 5,028,872 | A | 7/1991 | Nakabayashi |
| 5,038,515 | A | 8/1991 | Moorhead |
| 5,059,906 | A | 10/1991 | Yamanaka |
| 5,100,375 | A | 3/1992 | Koch |
| 5,153,546 | A | 10/1992 | Laskaris |
| 5,235,284 | A | 8/1993 | Tahara |
| 5,343,151 | A | 8/1994 | Cory |
| 5,359,310 | A | 10/1994 | Pissanetzky |
| 5,436,607 | A | 7/1995 | Chari |
| 5,446,934 | A | 9/1995 | Frazier |
| 5,534,669 | A | 7/1996 | Schroeder et al. |
| 5,539,316 | A | 7/1996 | Sukumar |
| 5,565,834 | A | 10/1996 | Hanley |
| 5,635,889 | A | 6/1997 | Stelter |
| 5,664,569 | A | 9/1997 | Damadian |
| 5,759,149 | A | 6/1998 | Goldberg et al. |
| 5,760,585 | A | 6/1998 | Dorri |
| 5,797,833 | A | 8/1998 | Kobayashi et al. |
| 5,800,335 | A | 9/1998 | Koch et al. |
| 5,817,003 | A | 10/1998 | Moll et al. |
| 5,840,010 | A | 11/1998 | Kobayashi |
| 5,883,558 | A | 3/1999 | Laskaris |
| 5,917,324 | A | 6/1999 | Leussler |
| 5,943,716 | A | 8/1999 | Chu |
| 5,971,913 | A | 10/1999 | Newkirk et al. |
| 6,036,634 | A | 3/2000 | Goldberg et al. |
| 6,081,120 | A | 6/2000 | Shen |
| 6,128,522 | A | 10/2000 | Acker |
| 6,147,578 | A | 11/2000 | Panfil |
| 6,155,970 | A | 12/2000 | Dykes et al. |
| 6,157,278 | A | 12/2000 | Katznelson |
| 6,177,795 | B1 | 1/2001 | Zhu |
| 6,193,285 | B1 | 2/2001 | Proctor |
| 6,208,142 | B1 | 3/2001 | Wagshul |
| 6,228,106 | B1 | 5/2001 | Simbruner |
| 6,231,499 | B1 | 5/2001 | Jones |
| D446,675 | S | 8/2001 | Straub |
| 6,278,274 | B1 | 8/2001 | Biglieri |
| 6,317,618 | B1 | 11/2001 | Livni et al. |
| 6,323,647 | B1 | 11/2001 | Anderson |
| 6,409,654 | B1 | 6/2002 | McClain et al. |
| 6,411,187 | B1 | 6/2002 | Rotem |
| 6,433,548 | B1 | 8/2002 | Furuta et al. |
| 6,471,634 | B1 | 10/2002 | Dykes et al. |
| 6,511,414 | B1 | 1/2003 | Hamsund |
| 6,535,092 | B1 | 3/2003 | Hurley |
| 6,611,702 | B2 * | 8/2003 | Rohling ............ A61B 5/0555 600/22 |
| 6,641,521 | B2 | 11/2003 | Kolarovic |
| 6,666,816 | B2 | 12/2003 | Mountain |
| 6,687,526 | B2 | 2/2004 | Brand |
| RE38,453 | E | 3/2004 | Lessard et al. |
| 6,707,363 | B1 | 3/2004 | Abele |
| 6,751,496 | B2 | 6/2004 | Su |
| 6,776,527 | B1 | 8/2004 | Tybinkowski et al. |
| 6,838,964 | B1 | 1/2005 | Knight |
| 6,860,272 | B2 | 3/2005 | Carter et al. |
| 6,992,486 | B2 | 1/2006 | Srinivasan |
| 7,071,692 | B2 | 7/2006 | Branch |
| 7,148,689 | B2 | 12/2006 | Huang |
| 7,255,671 | B2 | 8/2007 | Boone et al. |
| 7,274,192 | B2 | 9/2007 | Havens |
| 7,278,962 | B2 | 10/2007 | Lonneker-Lammers |
| D567,948 | S | 4/2008 | Tierney et al. |
| 7,378,848 | B2 | 5/2008 | Gao |
| 7,400,147 | B2 | 7/2008 | Rapoport |
| 7,482,558 | B2 | 1/2009 | Koch |
| 7,486,982 | B2 | 2/2009 | Branch |
| 7,529,575 | B2 | 5/2009 | Rezzonico |
| 7,551,954 | B2 | 6/2009 | Green |
| 7,599,728 | B2 * | 10/2009 | Feenan ............ A61B 5/055 600/411 |
| 7,621,815 | B2 | 11/2009 | Bosserdet, Jr. |
| 7,719,279 | B2 | 5/2010 | Rapoport |
| 7,784,121 | B2 | 8/2010 | Ahlman |
| 7,800,368 | B2 | 9/2010 | Vaughan |
| 7,999,541 | B2 | 8/2011 | Chisholm |
| 8,034,007 | B2 | 10/2011 | Avitable |
| 8,087,203 | B2 | 1/2012 | Boesel |
| 8,089,281 | B2 | 1/2012 | Zhai |
| 8,118,488 | B2 | 2/2012 | Gregerson |
| 8,147,396 | B2 | 4/2012 | Srinivasan |
| 8,194,866 | B2 | 6/2012 | Smith |
| 8,217,653 | B2 | 7/2012 | Vaughan |
| 8,319,496 | B2 | 11/2012 | Eryaman |
| 8,471,558 | B2 | 6/2013 | Chisholm |
| 8,525,116 | B2 | 9/2013 | Schulz |
| 8,555,578 | B2 | 10/2013 | Hushek |
| 8,807,084 | B2 | 8/2014 | Rapoport |
| 8,851,018 | B2 | 10/2014 | Rapoport |
| 8,969,829 | B2 | 3/2015 | Wollenweber |
| 9,055,912 | B2 | 6/2015 | Graumann |
| 9,100,111 | B2 | 8/2015 | Behrendt |
| 9,159,479 | B2 | 10/2015 | Rotem |
| 9,400,318 | B2 | 7/2016 | Fautz |
| 9,562,956 | B2 * | 2/2017 | Rapoport ............ G01R 33/422 |
| 9,696,269 | B2 | 7/2017 | Fordham |
| 9,974,705 | B2 | 5/2018 | Rapoport |
| 10,012,711 | B2 * | 7/2018 | Rapoport ............ G01R 33/422 |
| 10,078,122 | B2 | 9/2018 | Rapoport |
| 10,094,896 | B2 | 10/2018 | Rapoport |

(56) References Cited

U.S. PATENT DOCUMENTS

| | | |
|---|---|---|
| 10,132,887 B2 | 11/2018 | Rapoport |
| 10,224,134 B2 | 3/2019 | Nakatsu |
| 10,383,782 B2* | 8/2019 | Rapoport ............. A61G 11/006 |
| 10,426,376 B2* | 10/2019 | Rapoport ............. A61B 5/0555 |
| 10,499,830 B2* | 12/2019 | Rapoport ............. A61B 5/0555 |
| 10,524,690 B2* | 1/2020 | Rapoport ............. A61G 11/00 |
| 10,548,508 B2* | 2/2020 | Rapoport ............. A61G 11/002 |
| 10,847,295 B2 | 11/2020 | Rapoport |
| 2001/0013779 A1 | 8/2001 | Marek |
| 2001/0049465 A1 | 12/2001 | Goldberg et al. |
| 2002/0050895 A1 | 5/2002 | Zuk |
| 2002/0072648 A1 | 6/2002 | Dykes et al. |
| 2002/0123681 A1 | 9/2002 | Zuk et al. |
| 2002/0143233 A1 | 10/2002 | Donnelly et al. |
| 2002/0173696 A1 | 11/2002 | Kolarovic et al. |
| 2002/0173717 A1* | 11/2002 | Rohling ............... A61B 5/0555 600/415 |
| 2003/0016518 A1 | 1/2003 | Arz |
| 2003/0088175 A1* | 5/2003 | Branch ................ G01R 33/422 600/410 |
| 2004/0030241 A1 | 2/2004 | Green et al. |
| 2004/0034273 A1 | 2/2004 | Boris |
| 2004/0106844 A1 | 6/2004 | Lonneker-Lammers |
| 2004/0116799 A1 | 6/2004 | Srinivasan |
| 2004/0127786 A1 | 7/2004 | Schmit |
| 2004/0133064 A1 | 7/2004 | Castillon Levano et al. |
| 2004/0135687 A1 | 7/2004 | Keene |
| 2004/0147833 A1 | 7/2004 | Czipott |
| 2004/0186341 A1 | 9/2004 | McDermott |
| 2004/0194989 A1 | 10/2004 | Branch |
| 2004/0196043 A1 | 10/2004 | Branch |
| 2004/0236174 A1 | 11/2004 | Boone et al. |
| 2004/0236175 A1 | 11/2004 | Boone et al. |
| 2005/0004422 A1 | 1/2005 | Caspary et al. |
| 2005/0020906 A1 | 1/2005 | Seijger et al. |
| 2005/0027189 A1 | 2/2005 | Branch |
| 2005/0038314 A1 | 2/2005 | Falk |
| 2005/0043612 A1 | 2/2005 | Saint-Jalmes |
| 2005/0113668 A1 | 5/2005 | Srinivasan |
| 2006/0079730 A1 | 4/2006 | Getsla |
| 2006/0267585 A1 | 11/2006 | Havens |
| 2007/0068862 A1 | 3/2007 | Sisemore |
| 2007/0135704 A1 | 6/2007 | Branch |
| 2007/0232894 A1* | 10/2007 | Feenan ................ A61B 5/055 600/410 |
| 2007/0238950 A1 | 10/2007 | Vija |
| 2007/0249928 A1 | 10/2007 | Blezek |
| 2007/0273378 A1 | 11/2007 | Trequattrini |
| 2008/0001601 A1 | 1/2008 | Sellers |
| 2008/0103388 A1 | 5/2008 | Maschke |
| 2008/0122441 A1 | 5/2008 | Hayakawa |
| 2008/0163425 A1 | 7/2008 | White |
| 2008/0171931 A1 | 7/2008 | Maschke |
| 2008/0204028 A1 | 8/2008 | DeVries |
| 2008/0234571 A1 | 9/2008 | Hay |
| 2008/0246476 A1 | 10/2008 | Rapoport |
| 2008/0281187 A1 | 11/2008 | Massengill |
| 2009/0044335 A1 | 2/2009 | Brewin et al. |
| 2009/0072939 A1 | 3/2009 | Shen |
| 2009/0120615 A1 | 5/2009 | Icoz |
| 2009/0209846 A1 | 8/2009 | Bammer |
| 2009/0237077 A1 | 9/2009 | Vaughan |
| 2010/0004502 A1 | 1/2010 | Honma et al. |
| 2010/0010599 A1 | 1/2010 | Chen et al. |
| 2010/0066368 A1 | 3/2010 | Gao |
| 2010/0154325 A1 | 6/2010 | Boesel |
| 2010/0168502 A1 | 7/2010 | Delaporte et al. |
| 2010/0172468 A1 | 7/2010 | Gregerson |
| 2010/0198047 A1 | 8/2010 | Zagorchev |
| 2010/0219347 A1 | 9/2010 | Schulz |
| 2010/0245543 A1 | 9/2010 | Greer |
| 2010/0315085 A1 | 12/2010 | Brown |
| 2011/0048424 A1 | 3/2011 | Radko |
| 2011/0113555 A1 | 5/2011 | Smith |
| 2011/0125010 A1 | 5/2011 | Vaquero Lopez et al. |
| 2011/0160521 A1 | 6/2011 | Khodak et al. |
| 2011/0162652 A1 | 7/2011 | Rapoport |
| 2011/0172487 A1 | 7/2011 | Khodak |
| 2011/0274238 A1 | 11/2011 | Maschke |
| 2011/0280364 A1 | 11/2011 | Maschke |
| 2011/0280380 A1 | 11/2011 | Maschke |
| 2011/0282184 A1 | 11/2011 | Klingenbeck |
| 2011/0304333 A1 | 12/2011 | Rapoport |
| 2012/0071745 A1 | 3/2012 | Rapoport |
| 2012/0073511 A1 | 3/2012 | Rapoport |
| 2012/0078034 A1 | 3/2012 | Falk et al. |
| 2012/0126814 A1 | 5/2012 | Fischer et al. |
| 2012/0140899 A1 | 6/2012 | Bailey |
| 2012/0247488 A1 | 10/2012 | Tonks |
| 2013/0025062 A1 | 1/2013 | Esch |
| 2013/0109956 A1* | 5/2013 | Rapoport ............. A61B 5/055 600/411 |
| 2013/0150656 A1 | 6/2013 | Falk et al. |
| 2013/0204074 A1 | 8/2013 | Belval et al. |
| 2013/0204617 A1 | 8/2013 | Kuo et al. |
| 2013/0267765 A1 | 10/2013 | Rapoport |
| 2013/0334439 A1 | 12/2013 | Etters |
| 2014/0003614 A1* | 1/2014 | Levitov ................ G10K 11/002 381/71.7 |
| 2014/0051976 A1 | 2/2014 | Rapoport et al. |
| 2014/0055136 A1 | 2/2014 | Leussler |
| 2014/0078301 A1 | 3/2014 | Fazzi et al. |
| 2014/0098934 A1 | 4/2014 | Kondo |
| 2014/0099010 A1* | 4/2014 | Rapoport ......... G01R 33/56509 382/131 |
| 2014/0117989 A1* | 5/2014 | Rapoport ............. G01R 33/422 324/322 |
| 2014/0128725 A1 | 5/2014 | Rapoport |
| 2014/0152302 A1 | 6/2014 | Rapoport |
| 2014/0152310 A1 | 6/2014 | Rapoport |
| 2014/0155732 A1* | 6/2014 | Patz ...................... A61G 11/00 600/410 |
| 2014/0158062 A1 | 6/2014 | Rapoport |
| 2014/0230850 A1 | 8/2014 | Rapoport |
| 2014/0266203 A1 | 9/2014 | Rapoport |
| 2014/0354279 A1 | 12/2014 | Dumoulin et al. |
| 2014/0357981 A1* | 12/2014 | Dumoulin .......... A61G 13/1285 600/415 |
| 2014/0364722 A1* | 12/2014 | Dumoulin ............. G01G 19/44 600/415 |
| 2014/0378821 A1 | 12/2014 | Rapoport |
| 2014/0378825 A1 | 12/2014 | Rapoport |
| 2015/0005618 A1 | 1/2015 | Dumoulin |
| 2015/0059157 A1 | 3/2015 | Rapoport |
| 2015/0059655 A1 | 3/2015 | Rapoport |
| 2015/0061680 A1 | 3/2015 | Leskowitz |
| 2015/0065788 A1 | 3/2015 | Rapoport |
| 2015/0137812 A1 | 5/2015 | Rapoport |
| 2015/0141799 A1* | 5/2015 | Rapoport ............. A61B 5/0555 600/410 |
| 2015/0168519 A1 | 6/2015 | Rapoport |
| 2015/0226817 A1 | 8/2015 | Pourrahimi |
| 2015/0230766 A1 | 8/2015 | Wang |
| 2015/0253397 A1 | 9/2015 | Rapoport |
| 2015/0253400 A1 | 9/2015 | Rapoport |
| 2015/0253401 A1 | 9/2015 | Rapoport |
| 2016/0022123 A1 | 1/2016 | Katznelson |
| 2016/0030264 A1 | 2/2016 | Lehmann et al. |
| 2016/0032712 A1 | 2/2016 | Frosell |
| 2016/0081582 A1* | 3/2016 | Rapoport ................. A61F 7/00 600/415 |
| 2016/0089054 A1* | 3/2016 | Rapoport ............... G01R 33/34 600/415 |
| 2017/0143271 A1 | 5/2017 | Gustafsson |
| 2017/0146619 A1 | 5/2017 | Strauss |
| 2017/0181912 A1* | 6/2017 | Rapoport ............. A61B 5/0036 |
| 2019/0172620 A1 | 6/2019 | Rapoport |

FOREIGN PATENT DOCUMENTS

| | | |
|---|---|---|
| CN | 101185383 | 5/2008 |
| CN | 102136337 | 7/2011 |
| CN | 102551719 A | 7/2012 |

(56) References Cited

FOREIGN PATENT DOCUMENTS

| | | |
|---|---|---|
| CN | 103565437 B | 2/2014 |
| CN | 105358053 A | 2/2016 |
| DE | 19617739 | 6/1997 |
| DE | 102008009673 | 8/2009 |
| DE | 102008009674 | 8/2009 |
| DE | 202013105211 U1 | 12/2013 |
| DE | 202014102343 U1 | 6/2014 |
| EP | 0187691 | 7/1986 |
| EP | 0921527 | 6/1999 |
| EP | 1132072 | 9/2001 |
| EP | 1619667 | 1/2006 |
| EP | 2581071 | 4/2013 |
| GB | 863272 | 3/1961 |
| IL | 226488 | 7/2016 |
| JP | S5961763 | 4/1984 |
| JP | H04317630 | 11/1992 |
| JP | 2004531313 | 10/2004 |
| JP | 2005514078 | 5/2005 |
| JP | 2007252741 | 10/2007 |
| JP | 2010178857 | 8/2010 |
| JP | 2016539683 | 11/2016 |
| WO | 8910722 A1 | 11/1989 |
| WO | WO1998048756 | 11/1998 |
| WO | WO9921526 | 5/1999 |
| WO | 03030801 A2 | 4/2003 |
| WO | 2004029644 | 4/2004 |
| WO | 2005074608 | 8/2005 |
| WO | 2007052275 | 5/2007 |
| WO | WO2008137003 | 11/2008 |
| WO | WO2010054457 | 5/2010 |
| WO | 2010125559 | 11/2010 |
| WO | 2011001429 | 1/2011 |
| WO | WO2011109761 | 9/2011 |
| WO | WO2012143825 | 10/2012 |
| WO | 2013115847 A1 | 8/2013 |
| WO | WO2013115847 | 8/2013 |
| WO | 2014100106 A1 | 6/2014 |
| WO | 2014141251 | 9/2014 |
| WO | 2014188424 | 11/2014 |
| WO | 2014188426 | 11/2014 |

OTHER PUBLICATIONS https://pubmed.ncbi.nlm.nih.gov/10790632/ (Year: 2000).*
http://mriquestions.com/why-rf-shielding.html (Year: 2021).*
https://info.atlantisworldwide.com/blog/bid/348631/everything-you-need-to-know-about-rf-shielding-for-mri#:~:text=Both%20copper%20and%20galvanized%20steel,your%20MRI%20and%20work%20well. (Year: 2016).*
https://info.blockimaging.com/bid/90630/rf-shielding-for-mri-scanners-two-types-compared (Year: 2012).*
Glossary of MR Terms 4th edition; pp. 48-49 (Year: 1995).*
Antonucci, et al., The infant incubator in the neonatal intensive care unit: unresolved issues and future developments, J. Perinat. Med. 37(2009), 587-598.
Baby Pod II Infant Transport Device, Advance Healthcare Technology, brochure, pp. 1-6.
Baby Pod II Operation and Maintenance Manual, revision 5, Jan. 2011, pp. 1-11.
Ferris et al., The design of neonatal incubators: a systems-oriented, human centered approach, J. Perinatology, 2013, 33, S24-S31.
Kim et al., Air transparent soundproof window, AIP Advances 4, 117123 (2014), published online, doi: http//dx.org/10.1063/1.4902155.
Knutson, Allysa Jennie, Acceptable noise levels for neonates in the neonatal intensive care unit, A Capstone Project submitted in partial fulfillment of the requirements for the degree of: Doctor of Audiology, Washington University School of Medicine Program in Audiology and Communication Sciences, May 17, 2013, pp. 1-59.
Liu, Lichuan et al., Development and Applications of Active Noise Control System for Infant Incubators, Proceedings of the 2009 IEEE International Conference on Systems, Man, and Cybernetics San Antonio, Tx, USA—Oct. 2009, pp. 1-6.
Mahil et al., Hybrid Swarm Algorithm for the Suppression of Incubator Interference in Premature Infants ECG, Research Journal of Applied Sciences, Engineering and Technology 6(16): 2931-2935, 2013.
Marik et al., Neonatal incubators: A toxic sound environment for the preterm infant?, Pediatr Crit Care Med 2012 vol. 13, No. 6, pp. 1-6.
Paley et al., An MR-compatible neonatal incubator, The British Journal of Radiology, 85, 2012, 952-958.
American National Standard, Medical Electrical Equipment—Parts 2-19: Particular requirements for the basic safety and essential performance of infant incubators, Association for the advancement of medical instrumentation, ANSI/AAI/IEC 60601-2-19:2009, pp. 1-19.
Ranganna et al., Reducing noise on the neonatal unit, Infant, 2011, vol. 7, Issue 1, pp. 25-28.
Jenkins, S., ScanPod, BabyPod-Products-ScanPod, 2002-2011 Advance Healthcare Technology, ltd., internet website http://babypod.com:80/products/scanpod.php.
Science Daily, Inside the preemie brain, Incubator enables MRI scans on premeeies for preventing birth asphyxia, Dec. 1, 2005, pp. 1-2, Web address: http://web.archive.org/web/20130303154220/http://www.sciencedaily.com/videos/2005/1211-Inside_the_preemie_brain.htm.
Kitterman et al., Catheterization of umbilical vessels in newborn infants, Pediatric Clinics of North America, vol. 17, No. 4, Nov. 1970, 895-912.
Thermaxx Jackets, 5 most common thermal insulation materials, pp. 1-4, internet: https://www.thermaxxjackets.com/5-most-common-thermal-insulation-materials/.
Canadian Examiner Requisition for Application No. CA3,033,328, dated Jan. 31, 2020, 3 pages.
Eberich et al., Functional MRI in neonates using neonatal head coil and MR compatible incubator, NeuroImage 20 (2003) 683-692.
Extended European Search Report for Application No. EP17838915.1, dated Mar. 23, 2020, 8 pages.
International Preliminary Report on Patentability for PCT Application No. PCT/IL2014/50450 dated May 8, 2015. 7 pages.
International Search Report dated Jul. 27, 2012 in corresponding International Application No. PCT/IL2011/000537, 2 pages.
International Search Report for Application No. EP17785567.3, dated Nov. 20, 2019, 7 pages.
International Search Report for PCT Application No. PCT/IL2014/50451 dated Mar. 16, 2015. 2 pages.
International Search Report from PCT/IL2014/050450, dated May 21, 2014, 35 pages.
Notice of Allowance dated Mar. 25, 2020 for U.S. Appl. No. 16/040,214 (pp. 1-5).
Office Action dated Jan. 15, 2020 for U.S. Appl. No. 16/040,214 (6 pages).
Office Action for U.S. Appl. No. 14/892,209 dated Sep. 28, 2016. 22 pages.
Rapoport; U.S. App. No. 61/1905,221; filed Nov. 17, 2013; titled: MRI-Incubator's Closure Assembly. (50 pages).
Rapoport; U.S. Appl. No. 61/899,233; filed Nov. 3, 2013; titled: A Patient Transport Incubator. (54 pages).
Rapoport; U.S. Appl. No. 61/940,514; filed Feb. 17, 2014; titled: An Incubator Deployable Multi-Functional Panel. (100 pages).
Science Museum, "Fast Forward: 20 ways F1 is changing our world-Baby Pod II", uploaded Apr. 7, 2009, accessed online on May 26, 2016 at https://www.youtube.com/watch?v=KyZVhPWbWqo, 1 page.
Notice of Allowability dated Jul. 8, 2020 for U.S. Appl. No. 16/040,214 (pp. 1-2).
Chinese Office Action for App. No. CN201780053274.9, dated Aug. 25, 2020, 12 pages.
Chinese Office Action for App. No. CN201780061265.4, dated Aug. 31, 2020, 17 pages.
Office Action dated Jan. 25, 2021 for U.S. Appl. No. 16/095,612 (pp. 1-6).
Chinese Office Action (with English translation) for App. No. CN201780061265.4, dated Apr. 16, 2021, 10 pages.

(56) References Cited

OTHER PUBLICATIONS

Israeli Office Action (with English translation) for App. No. IL264729, dated Oct. 18, 2021, 9 pages.
Japanese Office Action for Application No. JP2019-506651, dated Mar. 3, 2021, 4 pages.
Notice of Allowance dated Jul. 6, 2021 for U.S. Appl. No. 16/324,218 (pp. 1-8).
Notice of Allowance dated Oct. 22, 2021 for U.S. Appl. No. 16/324,218 (pp. 1-8).
Office Action dated Aug. 31, 2021 for U.S. Appl. No. 17/103,505 (pp. 1-13).

* cited by examiner

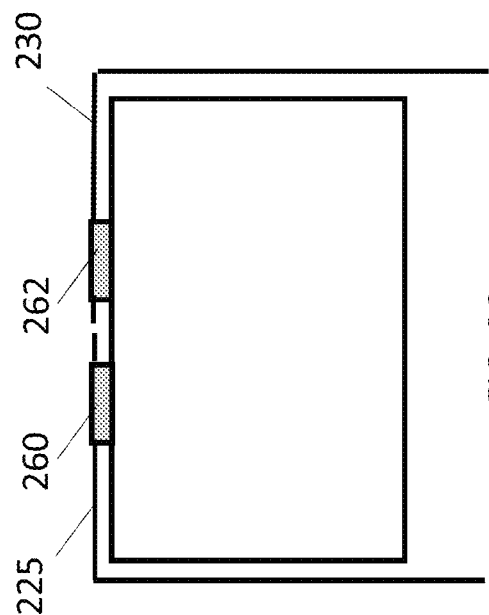
FIG. 2C
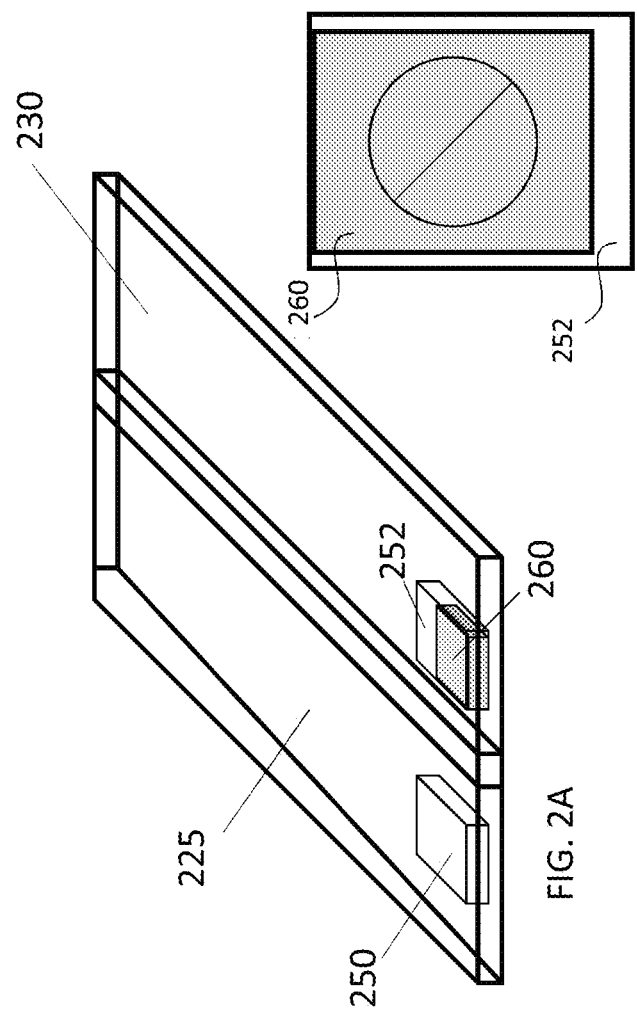
FIG. 2B
FIG. 2A

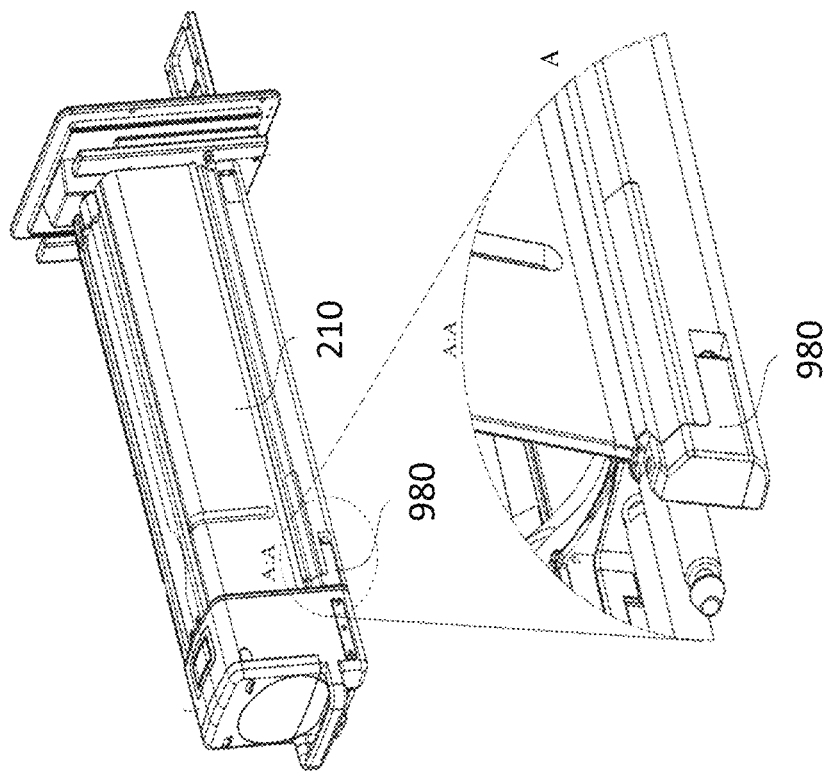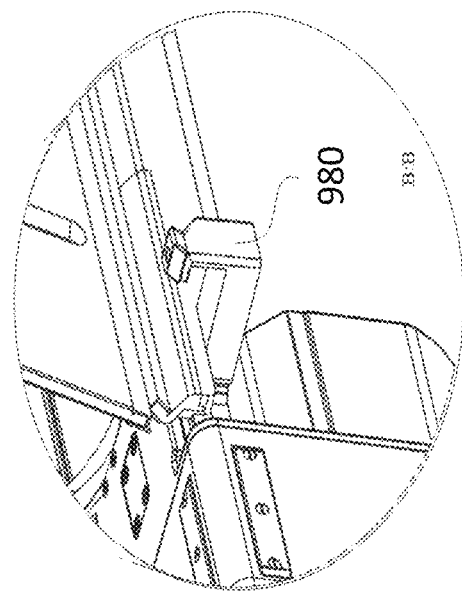

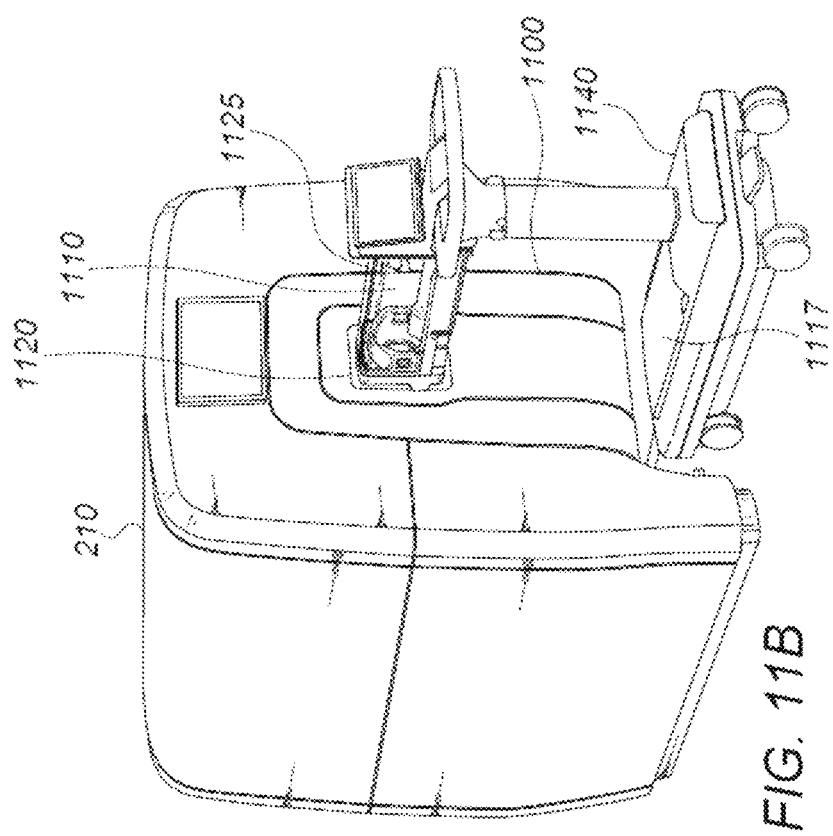

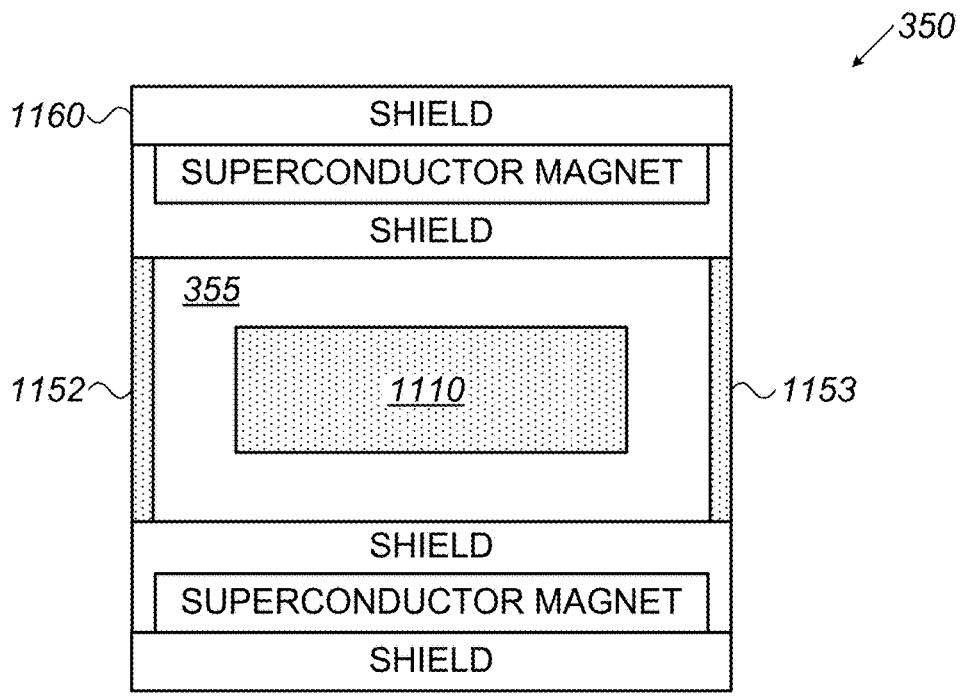
FIG. 11G
FIG. 11H
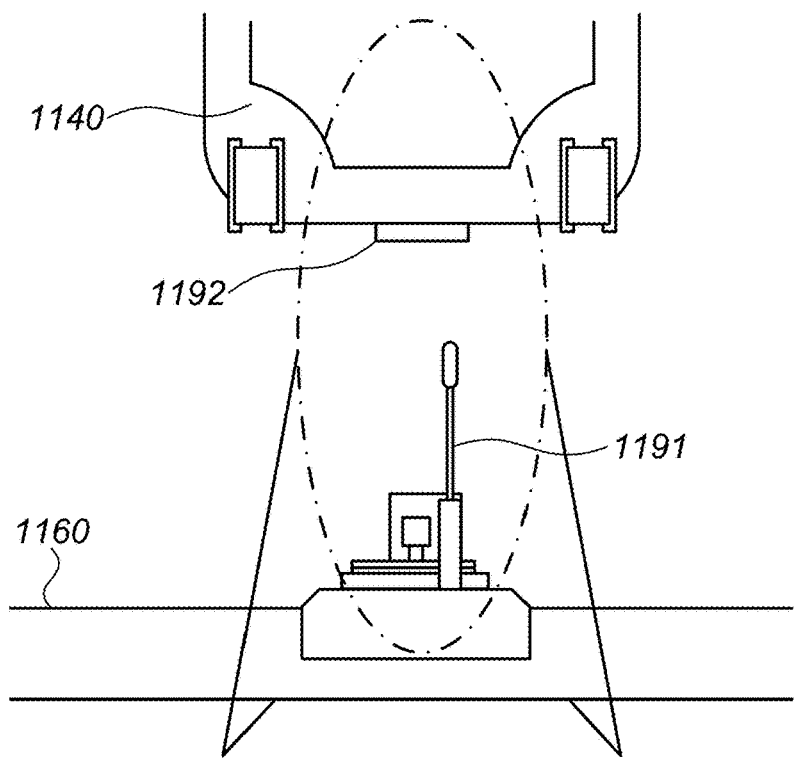

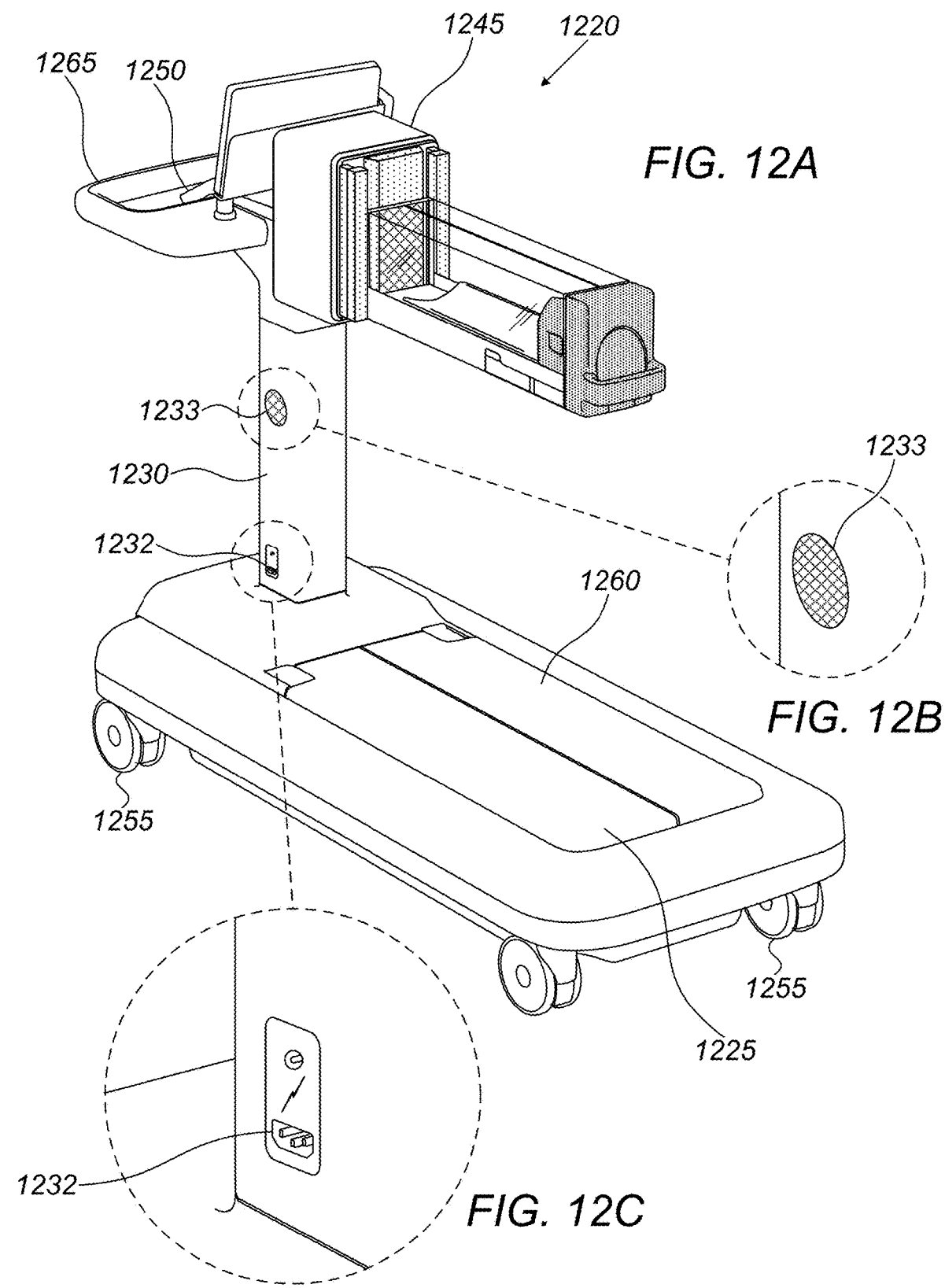

FIG. 12D
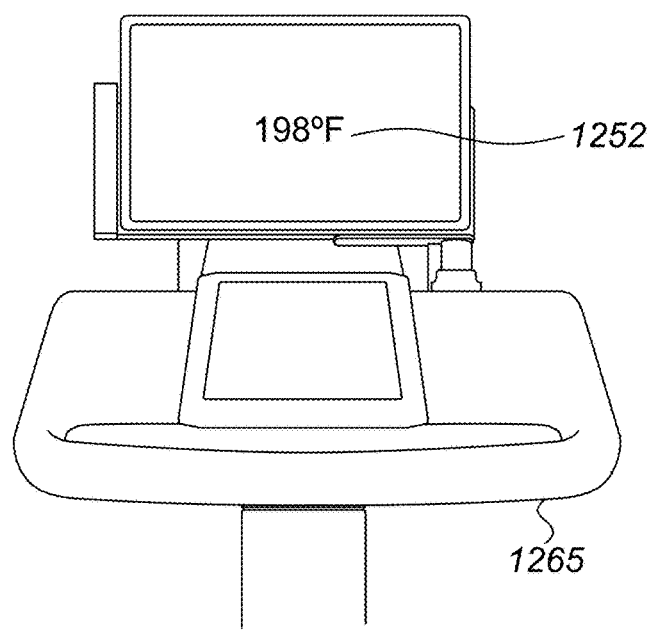
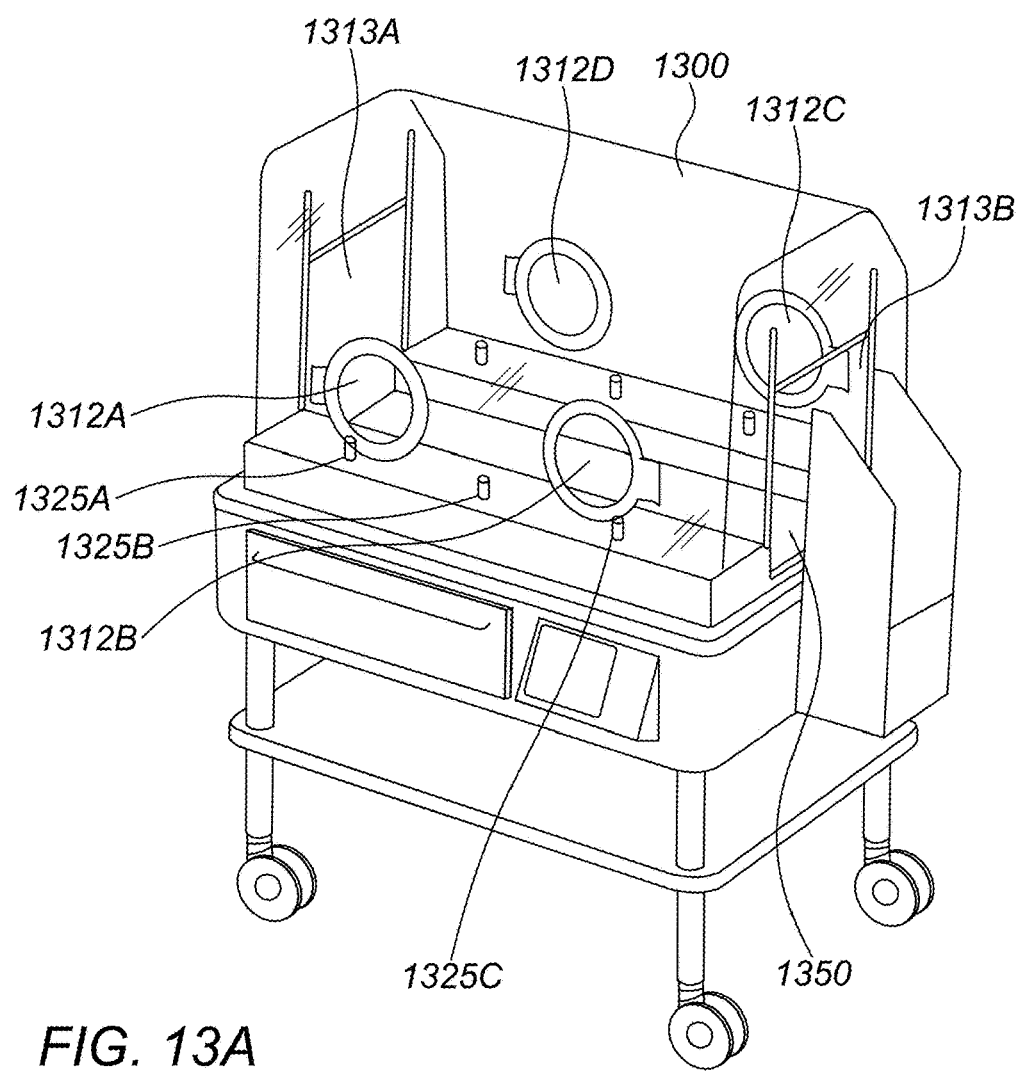
FIG. 13A

DEVICES AND METHODS FOR A NEONATE INCUBATOR, CAPSULE AND CART

CROSS-REFERENCE TO RELATED APPLICATIONS

[1] This application is continuation-in-part of PCT/IL2017/050425 filed on Apr. 6, 2017, which claims benefit of and priority to U.S. Provisional Patent Application No. 62/325,241 filed Apr. 20, 2016, the entire contents of which are all incorporated herein by reference in their entireties.

[2] This application is a continuation-in-part of U.S. patent application Ser. No. 15/402,437, filed on Jan. 10, 2017, which is a continuation-in-part of U.S. patent application Ser. No. 13/903,057, filed on May 28, 2013, which claim benefit of and priority to U.S. Provisional Application No. 61/720,440, filed on Oct. 31, 2012, the entire contents of which are all incorporated herein by reference in their entireties.

[3] This application is a continuation-in-part of U.S. patent application Ser. No. 15/367,839, filed on Dec. 2, 2016, which is a continuation-in-part of U.S. patent application Ser. No. 13/808,476, filed on Jul. 11, 2013, which is a national stage filing of PCT/IL11/00537, filed on Jul. 7, 2011, which claims benefit of and priority to U.S. Provisional Application No. 61/361,936, filed on Jul. 7, 2010, all of which are incorporated herein by reference in their entirety. U.S. patent application Ser. No. 15/367,839 is also a continuation-in-part of U.S. patent application Ser. No. 14/892,207, filed on Nov. 19, 2015, which is a national stage filing of PCT/IL2014/050450, filed on May 21, 2014, which claims the benefit of and priority to U.S. Provisional Patent Application No. 61/994,901, filed on May 18, 2014, the entire contents of which are all incorporated herein by reference in their entireties.

[4] This application claims benefit from and priority from U.S. Provisional Patent Application No. 62/380,750, filed on Aug. 29, 2016, U.S. Provisional Patent Application No. 62/380,753, filed on Aug. 29, 2016, 62/380,758, filed on Aug. 29, 2016, U.S. Provisional Patent Application No. 62/381,079, filed on Aug. 30, 2016, U.S. Provisional Patent Application No. 62/381,081 filed on Aug. 30, 2016, U.S. Provisional Patent Application No. 62/380,768 filed on Aug. 29, 2016, U.S. Provisional Patent Application No. 62/460,173, filed on Feb. 17, 2017, U.S. Provisional Patent Application No. 62/471,672, filed on Mar. 15, 2017, the entire contents of which are all incorporated herein by reference in their entireties.

FIELD OF THE INVENTION

The invention relates to imaging of a baby. In particular, the invention relates to a system for transporting a baby between a dock incubator and an imaging device.

BACKGROUND OF THE INVENTION

Neonates (e.g., human babies) are typically kept within an incubator when receiving medical treatment in a hospital. The incubator can provide constant environmental conditions (e.g., temperature, humidity, noise level, vibration level, light level, and/or bacteria/germ.) appropriate for life support of a baby and to support recovery of the baby. Baby incubators typically also allow for connection of various life support equipment and/or monitors to the baby and the incubator to, for example, provide feeding, monitor feeding, perform fluid exchange and/or monitor/control cardiac activity.

During medical treatment of a baby, procedures and/or imaging of the baby can require moving the baby out of the incubator about the hospital. Transporting the baby can require moving the baby from its controlled environment within the incubator, and in some instances, can require detaching/reattaching life support equipment attached to the baby (e.g., mechanical ventilation, oxygen, intravenous medications/hydration, etc.).

Transporting the baby can also require that the baby be picked up and repositioned into a transport device (e.g., a large transport incubator), which can disturb physical position and/or environment of the baby. For example, for a baby that has had surgery, it can be important to move the baby as minimally as possibly, to reduce risk of opening stiches and/or allowing infection to enter wound sites.

Transporting the baby can also require that every surface the baby touches and piece of connected/disconnected equipment be sterilized to, for example, prevent unwanted germs (e.g., staph infections) from infecting the baby.

Transporting the baby is typically done in a large incubator. This can be heavy and, in some instances, require multiple medical personnel to transport the baby.

When a baby on life support is transported, it can require such a disruption to the baby, that many times, the detriment of the disruption to the baby can outweigh the benefits that can be obtained from the reason for the transport (e.g., medical imaging of the baby's anatomy).

Therefore, it can be desirable to transport a baby for medical procedures without having to remove the baby from its controlled environment and/or detach/reattach life support equipment.

Some types of medical procedures (e.g., magnetic resonance imaging) can require magnetic and/or radio frequency (RF) shielding of life support equipment, elimination of magnetic materials in the vicinity of the baby being imagined, and/or addition of elements (e.g., an RF coil) into the environment of the baby, thus creating further disturbance to the environment of the baby.

Performing imaging of a baby can be an important diagnostic tool for a doctor. Imaging devices can be used to obtain images of a human's anatomy. For example, magnetic resonance imaging (MRI) devices can be used to create three-dimensional sections and/or layered images of body organs and/or tissue.

Other types of imaging devices that can require transporting a baby include x-ray radiography, ultrasound, elastography, tactile imaging, thermography, positron emission tomography (PET) and/or single-photon emission computer tomography (SPECT).

For some imaging devices, life support equipment may need to be magnetic and/or RF shielded. For example, MRI devices typically use a powerful magnet to create a magnetic field. The magnetic field can cause the nuclei atoms within a body to align with the magnetic field. Radio waves are typically applied to the body to cause the nuclei to change their alignment. When the radio waves are removed, the nuclei can relax back into their previous state. As the nuclei return to their previous state, they can emit distinct radio signals. The rate at which the nuclei emit signals and the frequency of the signals can depend on a type of the atom.

MRI devices can use a first radio frequency (RF) coil to generate the radio waves, which can be sometimes referred to as a gradient field, and a second RF coil to receive the radio waves, or can use the same RF coil to both transmit and/or receive.

MRI devices for medical diagnoses typically include a bore that a patient lying on a bed gets inserted into for imaging. The MRI devices are typically deployed in an MRI safe room in a hospital. The MRI safe room typically requires that all magnetic materials be left outside of the MRI room, so that they don't get pulled towards the MRI device by the force of the magnetic field to, for example, cause accidents. The MRI safe room also typically includes a RF shield in its walls. The RF shield can ensure that RF interference from outside of the MRI room does not compromise the MRI images, and can also ensure that RF energy generated by the MRI does not exit the room.

MRI imaging a patient connected to life support typically requires the patient be completely disconnected from all life support equipment, and reconnected to the life support equipment via very long tubing that is threaded through a hole in the MRI room, such that, for example, the life support equipment is outside of the MRI room and away from interference that can be caused by RF waves and/or magnetic energy. Additionally, MRI rooms are typically kept at a cold temperature, so that the magnets of the MRI don't overheat.

Obtaining MRI images of babies can require that the baby be moved out of its incubator into an uncontrolled environment (e.g., a cold/loud MRI room), all of the life support equipment be disconnected and reconnected (e.g., to move the baby into a transport incubator and/or to change/thread tubes of the life support equipment through a hole in the MRI room), placement of the baby on the same MRI bed that a non-baby patient is placed on and/or extensive and/or repeated sterilization of the MRI bed and/or life support equipment.

SUMMARY OF THE INVENTION

Advantages of the invention can include transporting a baby for imaging without removing the baby from its environment (e.g., temperature, humidity, noise level, vibration level, light level and/or bacteria/germ). Another advantage of the invention can include transporting a baby for imaging without disconnecting life support and/or medical tubing from the baby.

Another advantage of the invention can include an ability to obtain a magnetic resonance image (MRI) of a baby without a dedicated MRI room. Another advantage of the invention can include the ability to obtain a MRI of a baby with a MRI device that substantially eliminates a magnetic fringe field outside of the device, such that, for example, electronic equipment, metal and other objects that typically need to be shielded from an MRI (e.g., via an MRI shield room) can be positioned anywhere nearby the MRI device.

Another advantage of the invention can include an ability to transport the baby to multiple types of imaging devices. Another advantage of the invention can include an ability to transport of the baby with a reduced amount of help from support personnel. Another advantage of the invention can include transport of the baby without increasing a risk of infection. Another advantage of the invention can include an ability to monitor and/or vary an environment of the baby.

In one aspect, the invention involves a capsule incubator for positioning a neonate within an imaging device. The capsule incubator includes a bottom portion having a length, a width, and an inner surface for positioning the neonate thereon, a first flap includes a side portion that is coupled to and rotatable about the bottom portion along a first longitudinal edge of the bottom portion, the first side portion having a length equal to the length of the bottom portion. The first side portion also includes a top portion. The capsule incubator also includes a second flap. The second flap includes a side portion that is coupled to and rotatable about the bottom portion along a second longitudinal edge of the bottom portion, the second side portion having a length equal to the length of the bottom portion and a top portion. The first flap and the second flap are rotated to a first position such that the top portion of the first flap and the top portion of the second flap connect, to form a substantially closed housing for the neonate, and wherein the first flap and the second flap are rotated to a second position to form a substantially open housing for the neonate.

In some embodiments, the capsule incubator includes a radio frequency (RF) shield detachably mates with a first end of the capsule incubator, the RF shield comprising a conduit having a first aperture and a second aperture and the conduit having a length to width ratio of at least 5 to 1. In some embodiments, the capsule incubator includes a radio frequency (RF) coil positioning system that mates with a second end of the capsule incubator.

In some embodiments, the capsule incubator is made of a non-magnetic material. In some embodiments, the capsule incubator includes a first mating element to mate with a second mating element of a cart that connects to and transports the capsule incubator.

In some embodiments, the first flap further comprises a back portion and the second flap further comprises a back portion, and wherein the back portion of the first flap and the back portion of the second flap connect when the first flap and the second flap are rotated to the first position.

The capsule incubator of claim 1 further comprising a plug insertable into a first end of the capsule incubator or a second end of the capsule incubator to close the first end or the second end respectively. In some embodiments, the capsule incubator includes a light positioned within the capsule incubator.

In another aspect, the invention includes a dock incubator for housing a neonate that is within a capsule incubator. The dock incubator includes a first door to receive the capsule incubator and allow access to a first end of the neonate. The dock incubator also includes a second door to allow access to a second end of the neonate. The dock incubator also includes a first mating element to mate with a second mating element of the capsule incubator, to position the capsule incubator within the neonate incubator.

In some embodiments, the first mating element is a rail. In some embodiments, the first mating element is positioned on a bottom surface of the dock incubator. In some embodiments, the dock incubator includes at least two knobs positioned inside of the dock incubator coupled to a bottom surface of the dock incubator. In some embodiments, the first door and the second door are slidable doors.

In some embodiments, the dock incubator is made of non-magnetic material. In some embodiments, the dock incubator includes one or more lights positioned within the dock incubator. In some embodiments, the dock incubator includes one or more sensors to sense any temperature, sound level, air quality, and/or light level. In some embodiments, the dock incubator a transport base having a plurality of wheels to move the dock incubator.

In another aspect, the invention includes a cart for transporting a capsule incubator. a base coupled to at least two wheels. The cart includes a pillar coupled to the base and extending vertically from the base. The cart also includes a connector coupled to the pillar for detachably attaching the capsule incubator to the cart. The cart also includes a control panel for controlling the connector and one or more environmental conditions within the capsule incubator.

In some embodiments, the base includes a storage compartment. In some embodiments, the pillar is hollow and also includes an aperture. In some embodiments, the pillar is telescopic such that the height of a capsule incubator connected to the cart is adjustable relative to the base. In some embodiments, the cart includes a radio frequency (RF) shield coupled to the pillar, the RF shield including a conduit having a first aperture and a second aperture and the conduit having a length to width ratio of at least 5 to 1.

In some embodiments, the cart includes a handle. In some embodiments, the control panel includes a display. In some embodiments, the cart is made of MRI-safe material.

In another aspect, the invention includes a system for transporting a neonate to an imaging device. The system includes a capsule incubator for housing the neonate. The system also includes a dock incubator removably positioning the capsule incubator therein. The system also includes a cart for detachably attaching the capsule incubator to transport the capsule incubator. The system also includes an imaging device comprising a bore, the bore to receive the capsule incubator when attached to the cart such that when the capsule incubator is inserted into the bore the bore is closed.

In some embodiments, the system also includes a radio frequency (RF) shield coupled to the cart or the capsule, the RF shield comprising a conduit having a first aperture and a second aperture and the conduit having a length to width ratio of at least 5 to 1, and the RF shield sized to mate with the bore to close the bore.

In some embodiments, the cart also includes a base coupled to at least two wheels, the base having a storage compartment, a pillar coupled to the base and extending vertically from the base, a connector coupled to the pillar for detachably attaching the capsule incubator to the cart, and a control panel for controlling the connector, one or more environmental conditions within the capsule and the imaging device.

In some embodiments, the pillar includes an aperture such that one or more medical tubes can exit the pillar and enter an aperture of the capsule. In some embodiments, the dock incubator includes a first door to receive the capsule incubator and allow access to a first end of the neonate, a second door to allow access to a second end of the neonate, and a first mating element to mate with a second mating element of the capsule incubator, to position the capsule incubator within the neonate incubator.

In some embodiments, the first mating element and the second mating element are a rail and rail guide or a indent and roller that matches the indent. In some embodiments, the system includes a bed positioned within the capsule incubator, the bed comprising two pivot points to allow the bed to wrap around the neonate when positioned therein.

In some embodiments, the system includes the bed comprises an outer layer, an inner layer and a RF coil layer positioned between the inner layer and the outer layer. In some embodiments, the system includes the RF coil layer is rolled flexible print circuit board.

In some embodiments, the dock incubator has at least two knobs positioned inside of the dock incubator coupled to a bottom surface of the dock incubator, such that when the capsule incubator opens the sides of the capsule incubator rest upon the knobs, to allow air to flow from the bottom of the dock incubator around the capsule incubator to control air flow within the dock incubator.

In some embodiments, the system includes a radio frequency (RF) coil positioning device detachably attached to the dock incubator.

In another aspect, the invention involves a capsule incubator. The capsule incubator includes a surface for positioning a neonate thereon, the surface having a width and length sufficient for positioning a human baby. The capsule incubator also includes at least one closing structure, the closing structure to create a housing for the human baby when in a closed position and the create access to the human baby when in an open position. The capsule incubator also includes at least one coupling structure, to couple the capsule incubator to a cart, and a radio frequency (RF) shielding structure comprising a conduit having a first aperture and a second aperture and the conduit having a length to width ratio of at least 5 to 1.

BRIEF DESCRIPTION OF THE DRAWINGS

Non-limiting examples of embodiments of the disclosure are described below with reference to figures attached hereto that are listed following this paragraph. Dimensions of features shown in the figures are chosen for convenience and clarity of presentation and are not necessarily shown to scale.

The subject matter regarded as the invention is particularly pointed out and distinctly claimed in the concluding portion of the specification. The invention, however, both as to organization and method of operation, together with objects, features and advantages thereof, can be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

FIGS. 2A-2C are diagrams showing a safety mechanism that can prevent the first flap and/or the second flap from being pushed open, according to an illustrative embodiment of the invention.

FIGS. 9D and 9E are diagrams of safety mechanisms for a capsule incubator, according to illustrative embodiments of the invention.

FIG. 11B is a diagram of the MRI device of FIG. 11A with the capsule incubator positioned therein, according to an illustrative embodiment of the invention.

FIG. 11G is a diagram of the capsule incubator coupled to the cart and inserted into a superconductor magnet MRI device, according to an illustrative embodiment of the invention.

FIG. 11H is a diagram of an anti-slam locking system, according to an illustrative embodiment of the invention.

FIG. 12A is a diagram of a cart for transporting a capsule incubator, according to an illustrative embodiment of the invention.

FIG. 12B is a diagram of an air inlet of the cart of FIG. 12A, according to an illustrative embodiment of the invention.

FIG. 12C is a diagram of the electric power socket of the cart of FIG. 12A, according to an illustrative embodiment of the invention.

FIG. 12D is a diagram of the handle, the display, and the control panel, according to an illustrative embodiment of the invention.

FIG. 13A is an example of a dock incubator, in accordance with an illustrative embodiment of the invention.

DETAILED DESCRIPTION OF THE INVENTION

Figure 1:
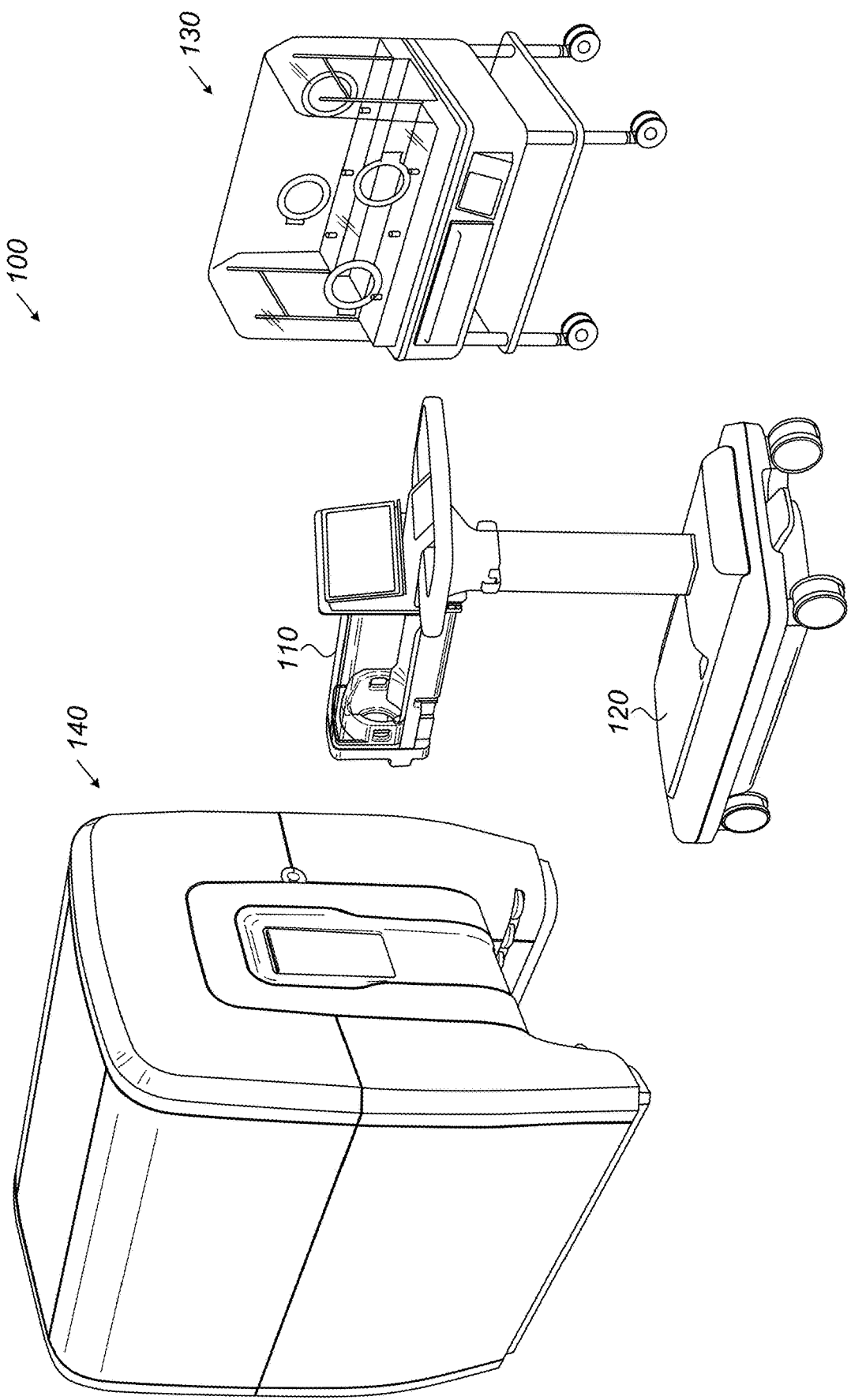
FIG. 1 is a diagram showing a system for housing and transporting a baby for imaging, according to an illustrative embodiment of the invention.

FIG. 1 is a diagram showing a system 100 for housing and transporting a baby for imaging, according to an illustrative embodiment of the invention. The system 100 can include a first incubator (e.g., capsule incubator) 110, a cart 120, a second incubator (e.g., dock incubator) 130, and an imaging device (e.g., MRI device) 140.

During operation, a baby (not shown) lies within the capsule incubator 110. The capsule incubator 110 can be positioned within the dock incubator 130, connected to the cart 120, or positioned within the MRI device 140. In some embodiments, the capsule incubator 110 is positioned in any desired location (e.g., other imaging devices, examination table and/or operating table).

The capsule incubator 110 can be moved between the dock incubator 130 and the MRI device 140 (or any desired location) via the cart 120. Life support equipment (not shown) attached to the baby can remain intact when moving the baby from the dock incubator 130 to a desired location via the cart 120 and the capsule incubator 110. The environment (e.g., temperature, humidity, noise level, vibration level, light level and/or bacteria/germ) surrounding the baby in the dock incubator 130 can be maintained in the capsule incubator 110 during movement of the baby in the capsule incubator 110.

In some embodiments, the baby is moved from the dock incubator 130 in the capsule incubator 110 attached to the cart 120, to a desired location, and the capsule incubator 110 does not detach from the cart 120 while the medical procedure occurs (e.g., imaging using the MRI device 140 with a bore to receive the capsule incubator 110). The baby can be moved from the dock incubator 130 to the medical procedure and back to the dock incubator 130 via the capsule incubator 110 and cart 120 without ever moving the life support equipment of the baby from the cart 120 or the modifying the environment of the baby.

In some embodiments, the baby is moved from the dock incubator 130 in the capsule incubator 110 attached to the cart 120, to a desired location, and the capsule incubator 110 detaches from the cart 120. The baby can be moved from the dock incubator 130 to the desired location via the capsule incubator 110 without removing the life support equipment from the baby.

The capsule incubator 110 can include a radio frequency (RF) shield (not shown) having at least two apertures and a conduit to allow tubing to be passed between an inside of the capsule incubator 110 and an environment outside of the capsule incubator 110. The RF shield substantially eliminates RF waves from entering/exiting the capsule incubator 110 despite the apertures.

Figure 2:
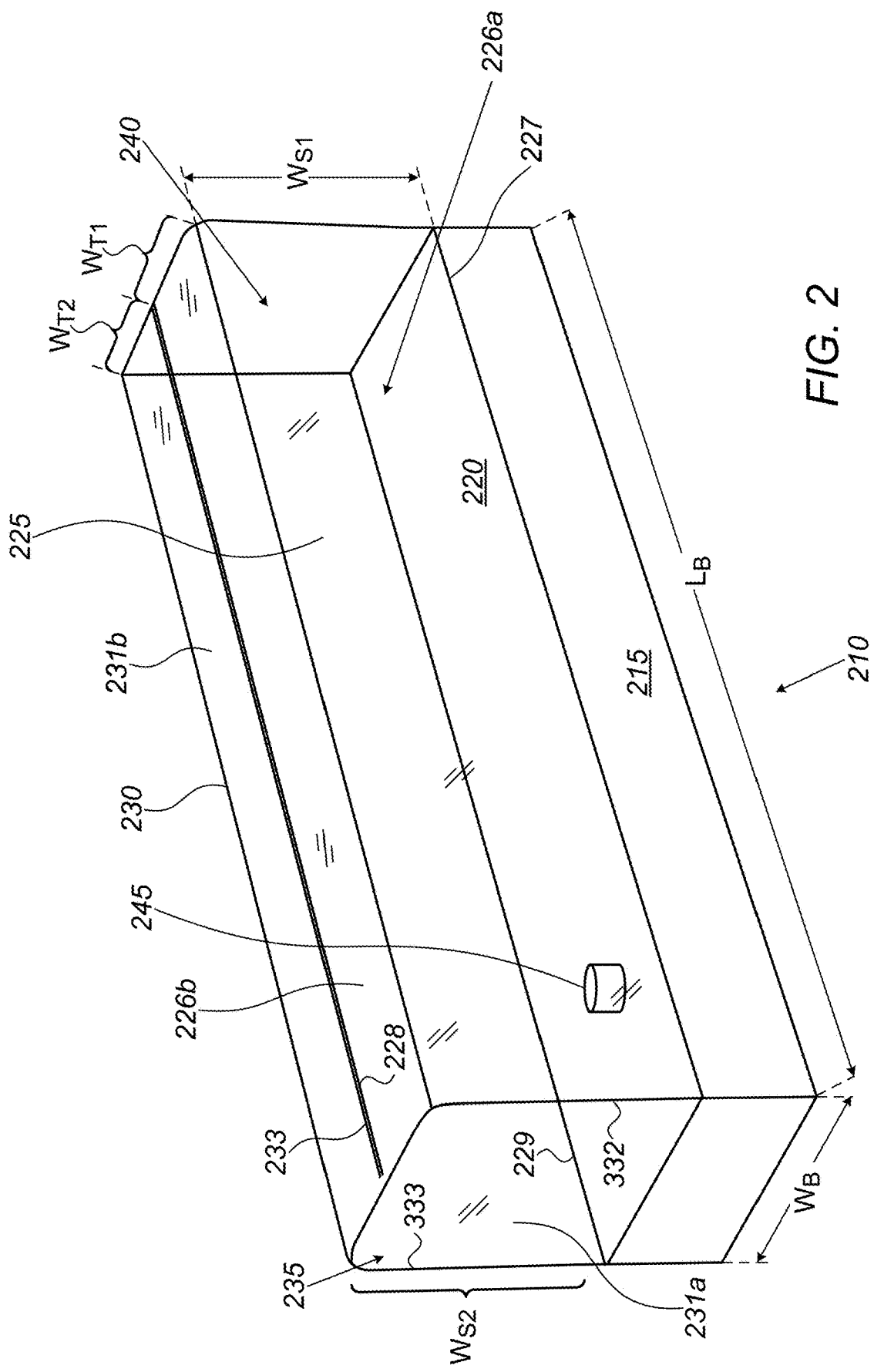
FIG. 2 is a diagram of a capsule incubator for positioning a baby within an imaging device, according to an illustrative embodiment of the invention.

FIG. 2 is a diagram of a capsule incubator 210 for positioning a baby within an imaging device, according to an illustrative embodiment of the invention. The capsule incubator 210 includes a bottom portion 215, an inner surface 220, a first flap 225, a second flap 230, a first end 235, and second end 240.

The bottom portion 215 can include the inner surface 220 (e.g., surface) that a baby can be positioned thereon. The bottom portion 215 can have a length and a width such that the baby can fit on the inner surface 220. In various embodiments, the bottom portion 215 has a length $L_B$ between 2 feet and 3 feet. In various embodiments, the bottom portion 215 has width $W_B$ between 3 inches and 6 inches.

The first flap 225 (e.g., a first closing structure) can be an L-shaped portion including a side portion 226a and a top portion 226b. The side portion 226a be coupled to and rotatable about the bottom portion 215 along a first longitudinal edge 227 of the bottom portion 215. The side portion 226a can be coupled to the bottom portion 215 via a hinge. The side portion 226a can be coupled to the bottom portion 215 as is known in the art.

The side portion 226a can have a length $L_{S1}$ equal to the length $L_B$ of the bottom portion 215. The side portion 226a can have a width $W_{S1}$ of 6 inches to 1.5 feet. The top portion 226b can have a length $L_{T1}$ equal to the length $L_B$ of the bottom portion 215. The top portion 226b can have a width $W_{T1}$ that is half the width $W_B$ of the bottom portion 215.

The top portion 226b can have a width $W_{W1}$ that can allow the top portion 226b to be a wall that prevents the baby from rolling out of the capsule incubator 210 when the side portion 226a is rotated such that the top portion 226b is parallel to a plane that is substantially perpendicular to the bottom portion 215 (e.g., in an open position). For example, the width $W_{T1}$ of the top portion 226b can be 6 inches to 1.5 feet The second flap 230 (e.g., a second closing structure) can be an L-shaped portion including a side portion 231a and a top portion 231. The side portion 231a be coupled to and rotatable about the bottom portion 215 along a second longitudinal edge 229 of the bottom portion 215. The side portion 231a can be coupled to the bottom portion 215 via a hinge.

The side portion 231a can have a length $L_{S2}$ equal to the length $L_B$ of the bottom portion 215. The side portion 231a can have a width $W_{S2}$ of 6 inches to 1.5 feet. The top portion 231 can have a length $L_{T2}$ equal to the length $L_B$ of the bottom portion 215. The top portion 231 can have a width $W_{T2}$ that is half the width $W_B$ of the bottom portion 215.

The top portion 231b can have a width $W_{W2}$ that enables the top portion 231b to be a wall that prevents the baby from rolling out of the capsule incubator 210 when the side portion 231a is rotated such that the top portion 231 is parallel to a plane that is substantially perpendicular to the bottom portion 215 (e.g., in an open position). For example, the width $W_{T2}$ of the top portion 231b can be 6 inches to 1.5 feet.

The first flap 225 and the second flap 230 can rotate to a first position (e.g., closed position) such that an edge 228 of the top portion 226b of the first flap 225 can connect to an edge 233 of the top portion 231 of the second flap 230. The edge 228 and the edge 233 can connect such that the connection is closed.

With the edges 228 and 233 connected (in other words, the first flap 225 and the second flap 230 are closed) the capsule incubator 210 can form a tubular structure, such that the first end 235 of the capsule incubator 210 and the second end 240 of the capsule incubator are open.

In some embodiments, each of the flaps include a safety mechanism that can prevent the first flap 225 and/or the second flap 230 from being pushed open when a force is applied perpendicular to (or substantially perpendicular to the first and/or second side portions 226a and 231a, the first flap 225 and/or the second flap 230 remain closed. For example, the safety mechanism can prevent the first flap 225 and/or the second flap 230 from being opened by a baby within the capsule incubator 210.

FIGS. 2A-2C show a safety mechanism that can prevent the first flap 225 and/or the second flap 230 from being pushed open, according to an illustrative embodiment of the invention. The first flap 225 and the second flap 230 (shown here only with their respective top portions) can include an opening, 250 and 252, respectively. The openings 250 and 252 can mate with a respective knob 260 and 262. The knobs 260 and 262 can fit in their respective openings 250 and 252 such that a force perpendicular to the side portions 226a and 221a (as shown in FIG. 2) does not allow the first flap 225 or the second flap 230 to open. The knobs 260 and/or 262 can be coupled to an RF shielding structure, an RF coil structure and/or a plug that is coupled to ends of the capsule incubator, as are described in further detail below.

Figure 2F:
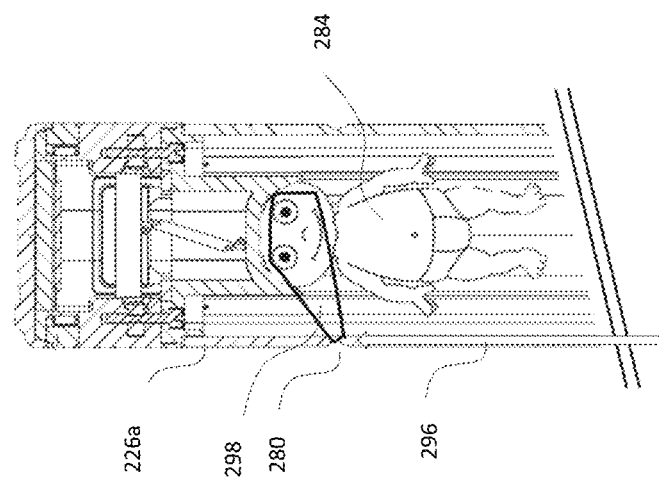
FIGS. 2D-2F are diagrams showing a mechanism for lighting a baby positioned within the capsule incubator, according to an illustrative embodiment of the invention.
Figure 2E:
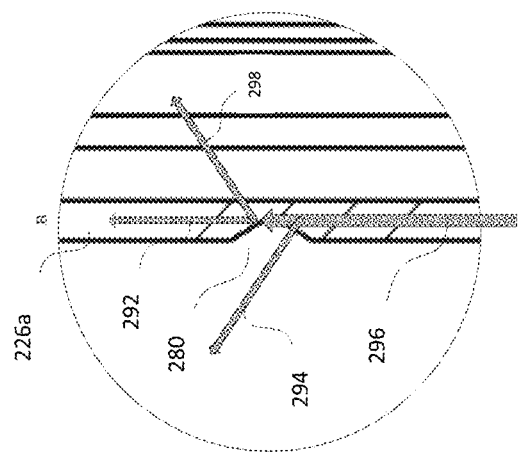
Figure 2D:
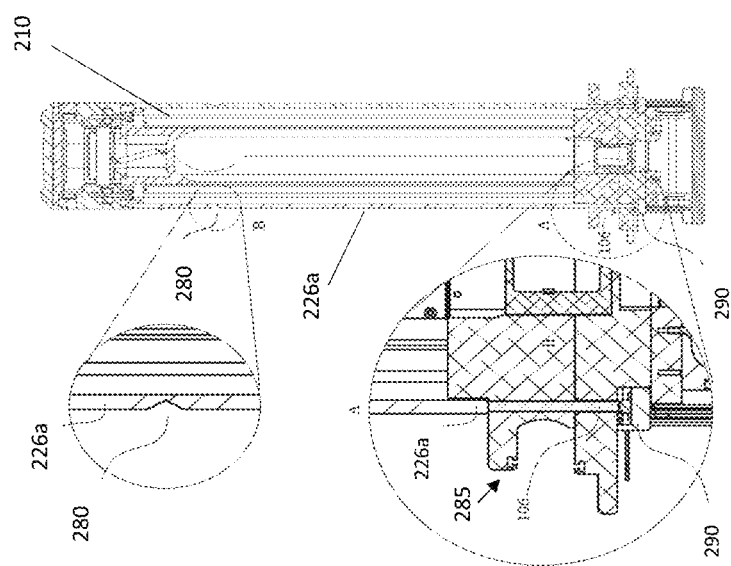

In some embodiments, the capsule incubator 210 can include a light that allows for lighting of the baby. The light can be positioned such that it causes minimal interference with a field of view of an MRI (or other imaging devices) when the baby within the capsule incubator 210 is positioned within the MRI while it is imaging the baby. FIGS. 2D-2F show diagrams that show a mechanism for lighting the baby, according to an illustrative embodiment of the invention. The light 290 (e.g., light emitting diode (LED) can be positioned at an end of a structure 285 that is coupled to an end of the capsule incubator 210. The structure 285 can be a radio frequency RF positioning system, a RF shielding structure and/or a plug as discussed in further detail below. The structure 285 can include a hollow canal 106 and a side portion 226a of the first flap 225 can include a recess 280 (e.g., a triangular recess). The side portion 226a can be a transparent material.

In some embodiments, the capsule incubator 210 is a transparent material. In some embodiments, the capsule incubator 210 is a non-magnetic material.

The transparent material can include poly-methyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, and/or polyvinyl chloride. In some embodiments, at least a portion of the transparent material is imbedded with non-transparent materials for means of strength and/or conductivity such as metallic wire.

During operation, light 296 emitted from the LED 290 can travel down the hollow canal 106 to impinge upon the side portion 226a. The light 296 can travel through the side portion 226a towards the recess 280. When the light 296 impinges upon the recess 280 it can disperse into three portion 294, 292, and/or 298, respectively. The light portion 294 can be external to the capsule incubator. The light portion 292 can continue along the side portion 226a. The light portion 298 can be directed internal to the capsule incubator 210. With a baby 284 positioned within the capsule incubator 210, the light portion 298 can illuminate the baby 284. The recess 280 can be configured to cause the light 298 to impinge upon a face of the baby 284.

In some embodiments, the first flap 225 and the second flap 230 are c-shaped. In some embodiments, the capsule incubator 210 has a one portion (e.g., a closing structure) that opens and closes the capsule incubator 210. For example, as described in further detail below in FIG. 5A and FIG. 5B.

Figure 3A:
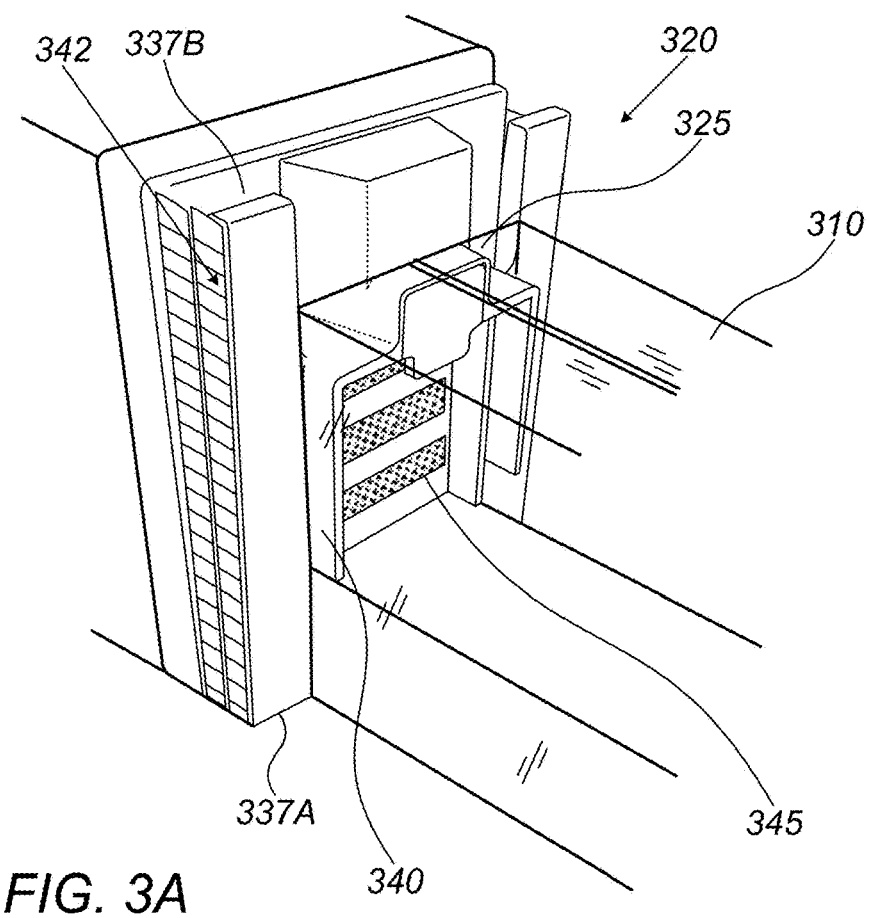
FIG. 3A is a diagram of radio frequency (RF) shield structure coupled to an end of a capsule incubator, according to an illustrative embodiment of the invention.

In some embodiments, a radio frequency (RF) shield structure (not shown) is coupled to the first end 235, such that when the first flap 225 and the second flap 230 close, the RF shield structure forms a plug for the first end 235. In some embodiments, the RF shield structure is coupled to the second end 240. FIG. 3A is a diagram of an RF shield structure 320 coupled to an end 325 of a capsule incubator 310, according to an illustrative embodiment of the invention. The RF shield structure 320 is coupled to the end 325 of the capsule incubator 310 such that the RF shield structure 320 substantially closes the end 325 and can provide RF shielding between an interior and exterior environment of an MRI when the end 325 and capsule incubator 310 are pushed into an MRI such that the RF shield structure 320 form a door to the MRI and closes.

Figure 3B:
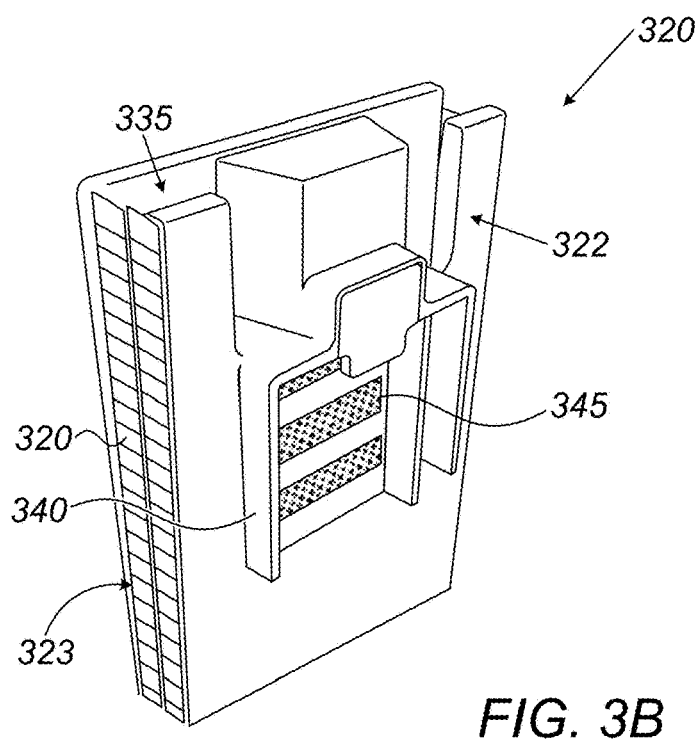
FIG. 3B is a diagram of the RF shield structure of FIG. 3A, according to an illustrative embodiment of the invention.

FIG. 3B is a diagram of the RF shield structure 320, according to an illustrative embodiment of the invention. The RF shield structure 320 can include a first surface 322, a second surface 323, a conduit 335, a protruding portion 340, and an RF shield 345.

The conduit 335 can include a first aperture 337a, a second aperture 337b, and an access port 342. The access port 342 can be a non-magnetic material.

The first surface 322 can face the capsule incubator 310 and the second surface 323 can face an environment exterior to the capsule incubator 310. The first surface 322 can include the protruding portion 340. The protruding portion 340 can have a size and shape such that when the first flap 225 and the second flap 230 are connected, an end edge 332 of the first flap 225 and an end edge 333 of the second flap 230 mate with the protruding portion 340 to seal the end 235, such that the RF shield structure 320 plugs the end 235 of the capsule incubator 310. As shown in FIG. 3A, the protruding portion 340 has a shape such that when the end edge 332 of the first flap 225 closes with the end edge 333 of the second flap 230 they form a substantially square shape around the protruding portion 340 having conduits 327a and 327b to allow one or more tubes to extend from aperture 327a through conduit 335 out of aperture 337b through aperture 327a into the capsule incubator 310. As is apparent to one of ordinary skill in the art, the tubes can extend on the other side of the RF shielding structure with the capsule as shown. For embodiments having a c-shaped first and second flaps, the protruding portion 340 can be circular.

The RF shield 345 is a square shape that fits within the square shaped protruding portion 240. In various embodiments, the RF shield 345 can be a shape that fits within the protruding portion 240 such that the interior of the capsule incubator 310 is RF shielded at the end 235. The RF shield 345 can be a honeycomb tubular structure to allow air in and maintain the 5 to 1 ratio. For example, the honeycomb can be sized such that each individual opening in the honeycomb has a length to width ratio of 5 to 1. The RF shield can be a mesh.

The second surface 323 can be a surface that is capable of mating with the RF shielding structure to connect the capsule incubator to a cart (e.g., cart 120, as described above in FIG. 1). In some embodiments, the second surface 323 is flat.

During operation, one or more tubes (e.g., medical tubes, life support tubes, monitors, and/or any tubing that may need to be present within the capsule incubator 310) are positioned in the conduit 335 via the access port 342. In this manner, tubing connected to the baby can be routed through the RF shield 345 without removing the tubing from the baby. When the capsule incubator 310 is positioned within an MRI device having a bore (e.g., the MRI device as described below in FIG. 11A), the walls of the bore enclose the conduit 335 to form a conduit that is completely closed. The conduit 335 can have a length to width ratio of at least 5 to 1. During operation, the RF shielding structure 320 can prevent RF leakage into and/or out of the capsule incubator 310. The length to width ratio of the conduit 335 can prevent RF leakage through the conduit 335 into and/or out of the capsule incubator 310. The RF shield structure 320 can allow for tubes to enter/exit the capsule incubator 310 without removing the tubes from the baby and without RF leakage into and/or out of the capsule incubator 310.

Turning back to FIG. 2, in some embodiments, a radio frequency (RF) coil positioning system (not shown) is coupled to the second end 240 of the capsule incubator 210, such that when the first flap 225 and the second flap 230 close, the RF coil positioning system forms a plug for the second end 240. In some embodiments, the RF coil positioning system is coupled to the first end 235.

Figure 4A:
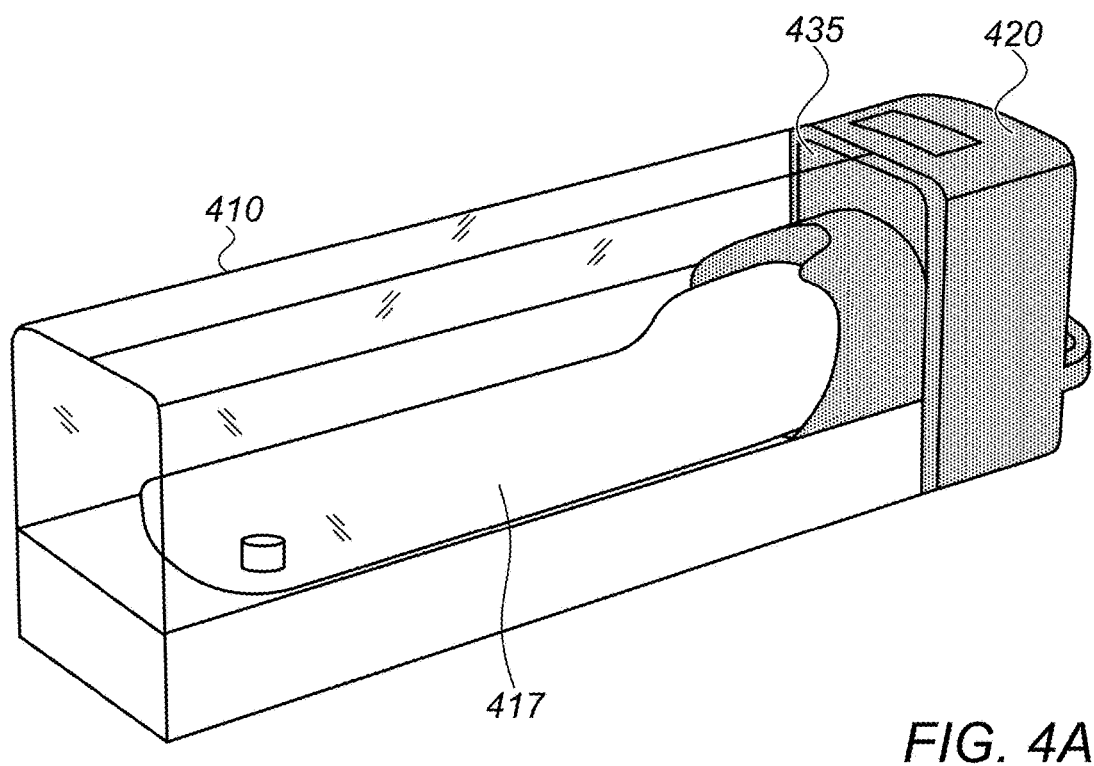
FIG. 4A is a diagram of radio frequency (RF) coil positioning system coupled to an end of a capsule incubator, according to an illustrative embodiment of the invention.

FIG. 4A is a diagram of a RF coil positioning system 420 coupled to an end 435 of the capsule incubator 410, according to an illustrative embodiment of the invention. The RF coil positioning system 420 is coupled to the end 435 of the capsule incubator 410 such that the RF coil positioning system 420 closes the end 435.

Figure 4B:
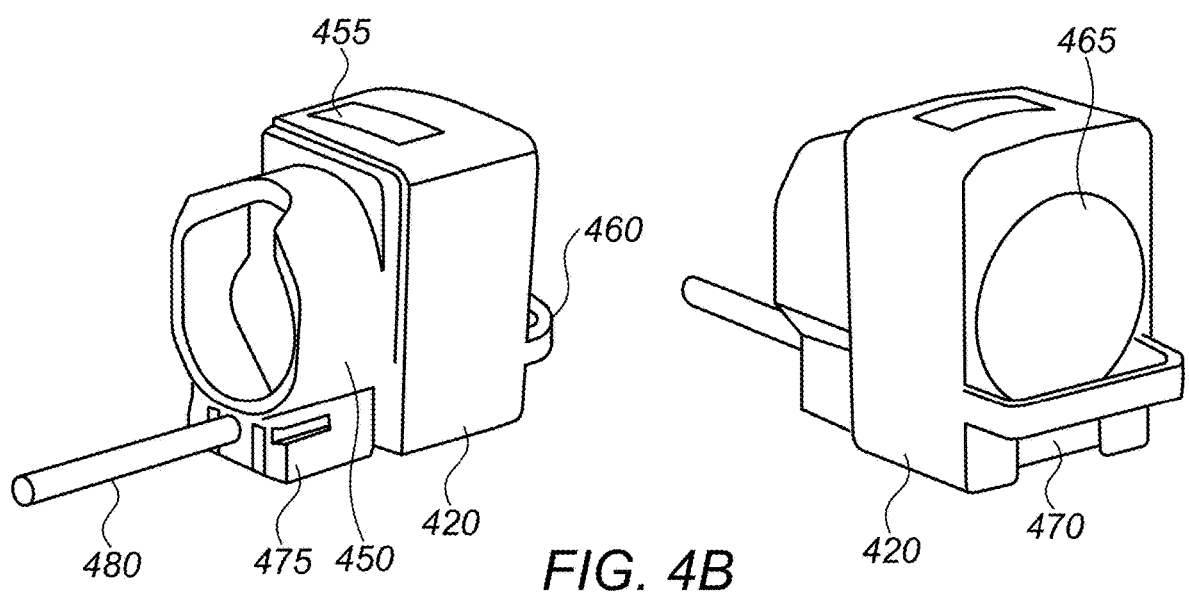
FIG. 4B is a diagram of the RF coil positioning system of FIG. 4A, according to an illustrative embodiment of the invention.
Figure 4E:
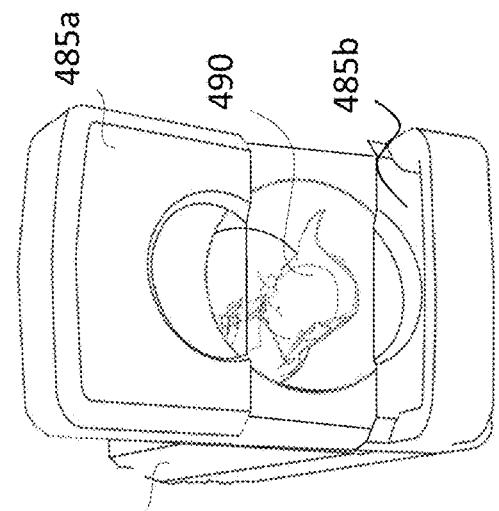
FIGS. 4C-4E show a radio frequency (RF) coil positioning system having a first portion and a second portion, according to illustrative embodiments of the invention.

FIG. 4B is a diagram of the RF coil positioning system 420, according to an illustrative embodiment of the invention. The RF coil positioning system 420 can include a head coil portion 450, a release push button 455, a handle 460, a window 465, a one or more connectors 470, a connector 475, and a centering rod 480. The RF coil positioning system 420 can be used in combination with a patient bed 417 to position a head of the neonate within a particular location within the head coil portion 450. For example, as shown in U.S. provisional patent application No. 62/325,241 filed Apr. 20, 2016 and PCT application no. PCT/IL2017/0504425 filed on Apr. 6, 2017, all of which are incorporate herein by reference in their entireties.

The one or more connectors 470 can allow for the RF coil (not shown) that is within the head coil portion 450 to couple to an MRI (e.g., MRI as described above in FIG. 1) when the capsule incubator 210 with the RF coil positioning system 420 are inserted into the MRI. In particular, the one or more connectors 470 mate with one or more connectors that are positioned within the MRI (e.g., via blind coupling). When coupled to the MRI, the RF coil within the head coil portion 450 can receive signals transmitted from the MRI. The signals can be signals as are known in the art.

In some embodiments, the RF coil positioning system 420 can rotate beneath the capsule incubator 210. The RF coil positioning system 420 can rotate about the centering rod 480. The centering rod 480 can be inserted within an aperture (not shown) that is in the bottom portion of the capsule incubator 410. During operation, the RF coil positioning system 420 can be pulled away from the capsule incubator 210 (e.g., via the handle 460) and remains connected to the capsule incubator 410 via the centering rod 480. The centering rod 480 can be prevented from completely exiting the aperture, such that the RF coil positioning system 420 remains connected to the capsule incubator 210. The RF coil positioning system 420 can rotate about centering rod 480. In this manner, the RF coil positioning system 420 can be quickly removed in an emergency to access a baby within the capsule incubator 210. In some embodiments, the RF coil positioning system 420 can be rotated as described in U.S. Patent Publication No. 2016/0089055 filed on May 21, 2014, the entire contents of which are incorporated herein by reference in its entirety.

Figure 4D:
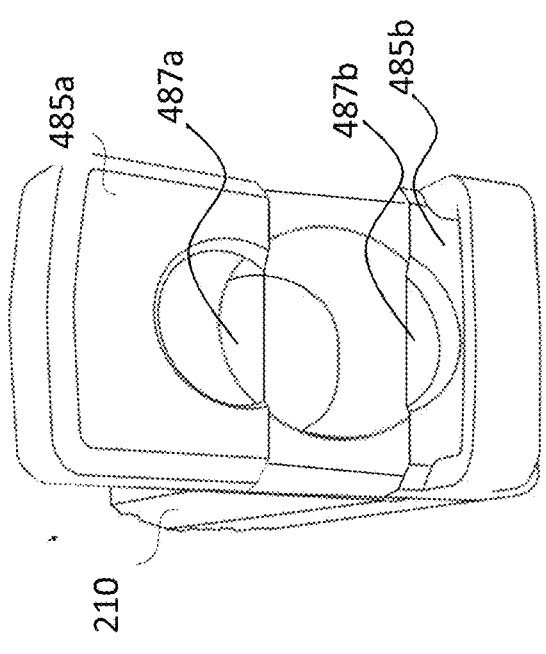
Figure 4C:
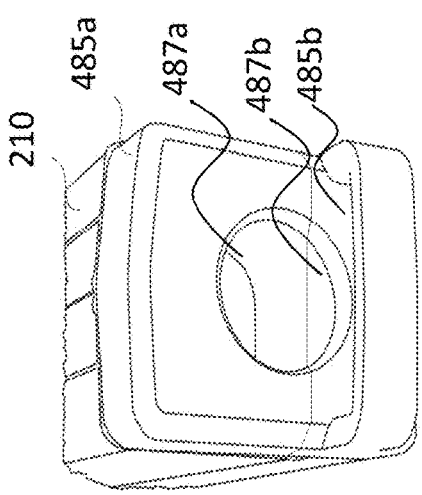

In some embodiments, the RF coil positioning system 420 can include two portions that can slide between an open and closed position to allow access to a baby while the baby's head is within the RF coil positioning system 420. FIGS. 4C-4D show an RF coil positioning system 420 having a first portion 485a, a second portion 485b, window portions 487a and 487b, according to illustrative embodiments of the invention. The first portion 485a can slide with respect to the second portion 485b, such that the RF coil positioning system 420 is open and a baby 490 can be accessed.

The RF coil positioning system 420 can be a RF coil assembly as shown in U.S. patent application Ser. No. 15/545,572 filed on Mar. 9, 2017, incorporated herein by reference in its entirety.

In some embodiments, the RF coil positioning system 420 casing is made of non-magnetic material.

In some embodiments, the RF coil positioning system 420 is not used and an RF coil as is known in the art is positioned around the baby.

Turning back to FIG. 2, in various embodiments, the first end 235 and/or the second end 240 are plugged via an end piece (not shown). In various embodiments, the first end 235 and/or the second end 240 are plugged via the first flap 225 and/or the second flap 230 having respective end portions.

Figure 5A:
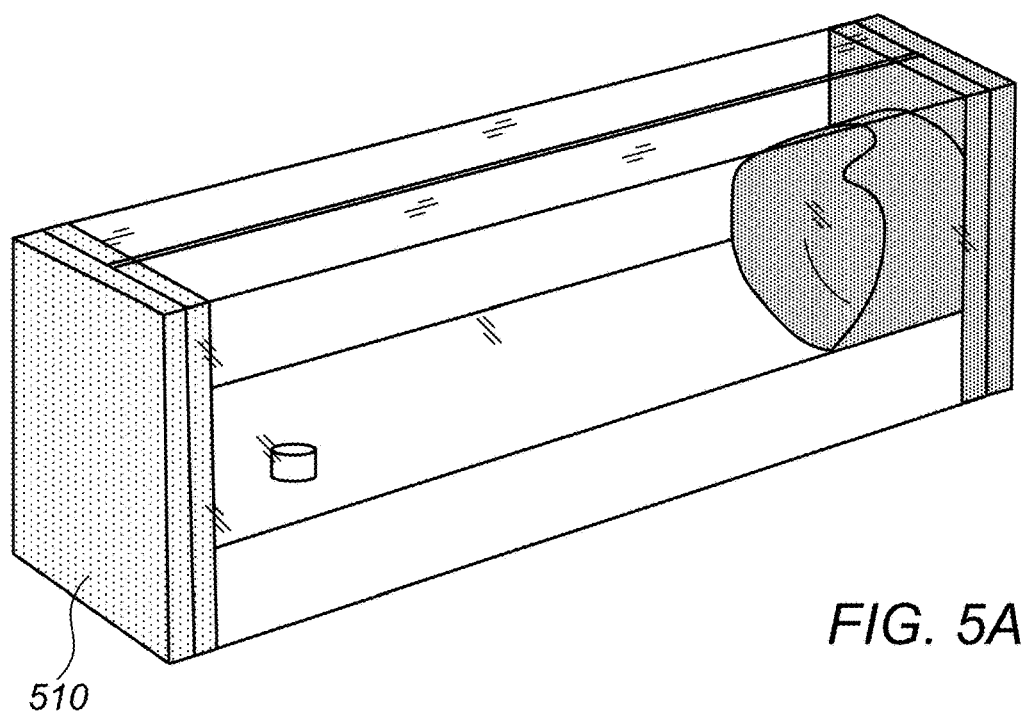
FIG. 5A is a diagram of an end piece for a capsule incubator, according to an illustrative embodiment of the invention.
Figure 5B:
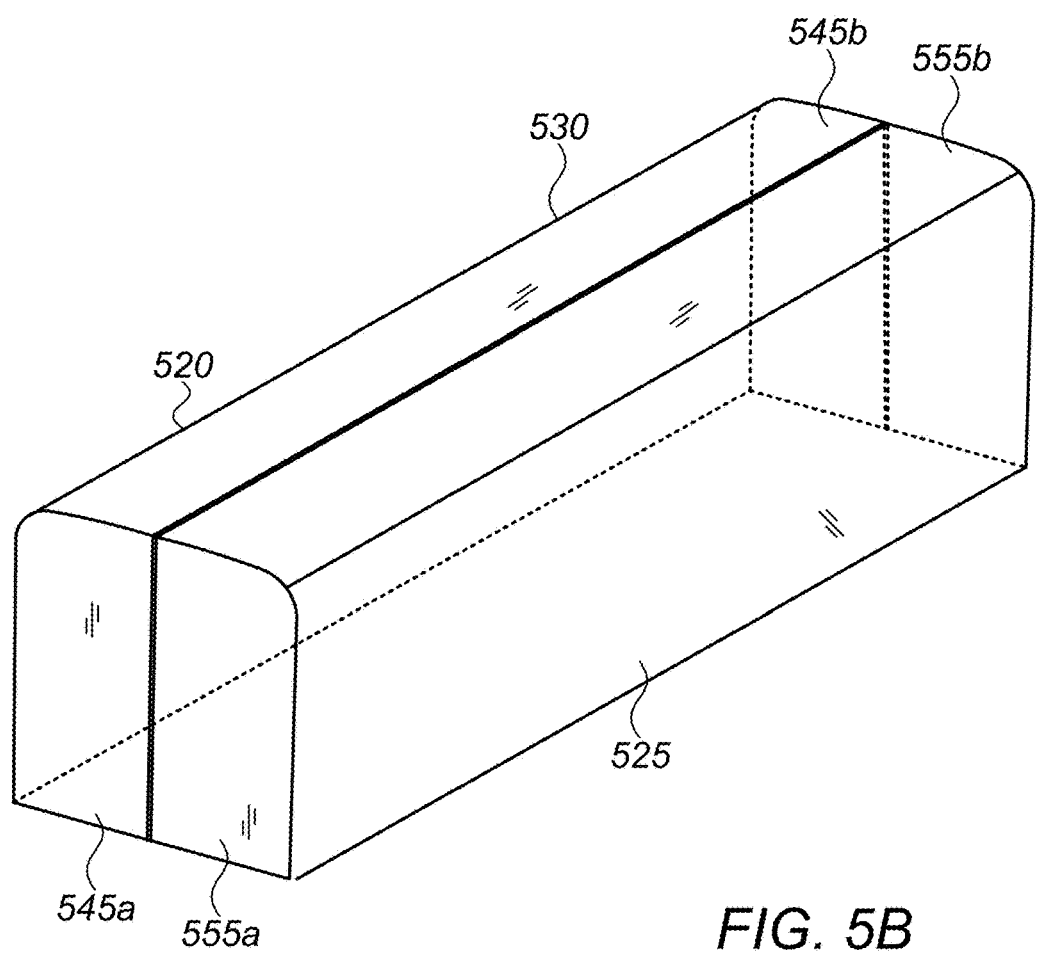
FIG. 5B is a diagram of the capsule incubator of FIG. 5A, according to an illustrative embodiment of the invention.

FIG. 5A is a diagram of an end piece 510 for a capsule incubator 520, according to an illustrative embodiments of the invention. The end piece 510 can be used to plug the first end 235 and/or the second end 240 of the capsule incubator 520. FIG. 5B is an example of a capsule incubator 520, according to an illustrative embodiment of the invention. The capsule incubator 520 includes a first flap 525 and a second flap 530 including respective end portions 545a, 545b, and 555a and 555b. When the first flap 525 and the second flap 530 connect, the respective end portions 545a and 555a connect, and end portions 545b and 555b connect.

Figure 5D:
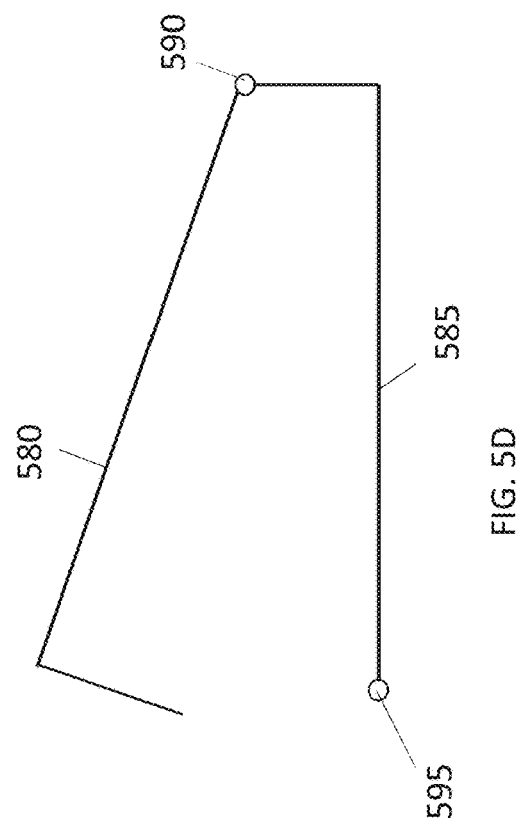
FIG. 5C and FIG. 5D are diagrams of a capsule incubator, according to illustrative embodiments of the invention.
Figure 5C:
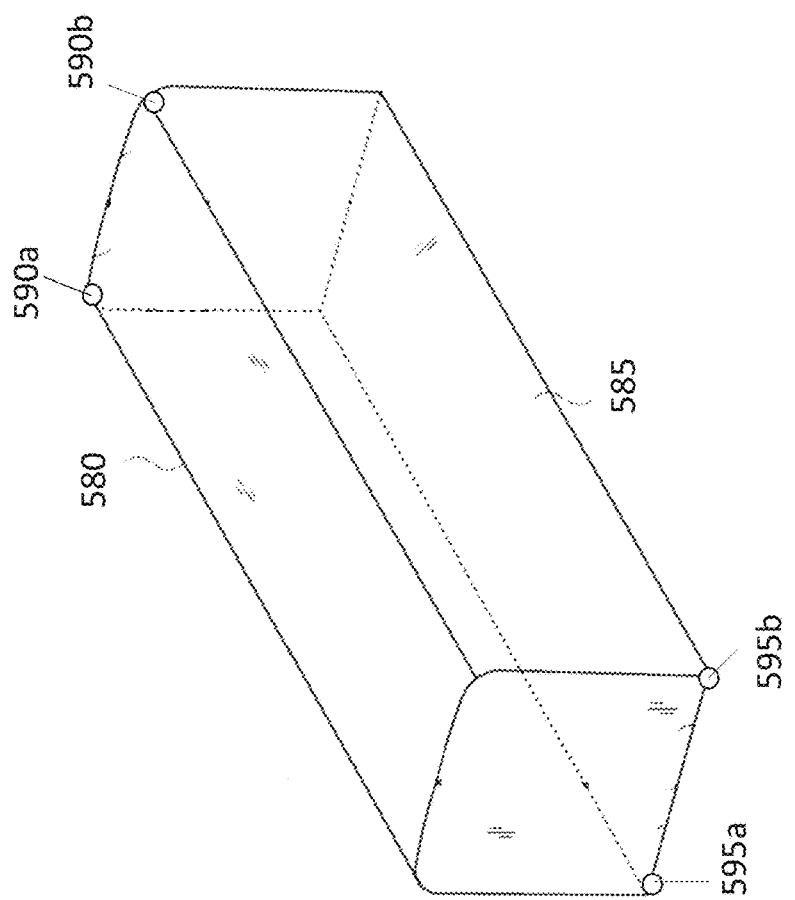

In some embodiments, the capsule incubator 20 can be a single L shaped flap that rotates about an axis. For example, FIG. 5C and FIG. 5D are diagrams an L shaped capsule having one flap 580. The flap 580 rotates about pivot points 590a and 590b, and closes at points 595a and 595b.

Turning back to FIG. 2, in some embodiments, the bottom portion 215 can include a knob 245. The knob 245 can allow a patient bed 250 to be coupled to the bottom portion 215. The patient bed 250 can be raised and lowered to allow the baby's head to be positioned substantially in a center of a RF coil.

Figure 6A:
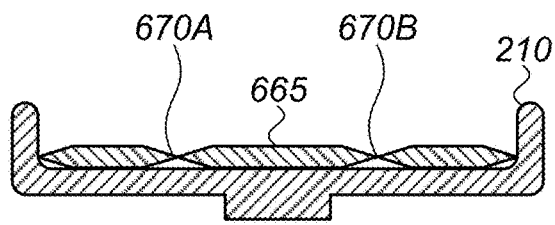
FIG. 6A is a front view diagram of the capsule incubator of FIG. 2, with a patient bed, according to an illustrative embodiment of the invention.
Figure 6B:
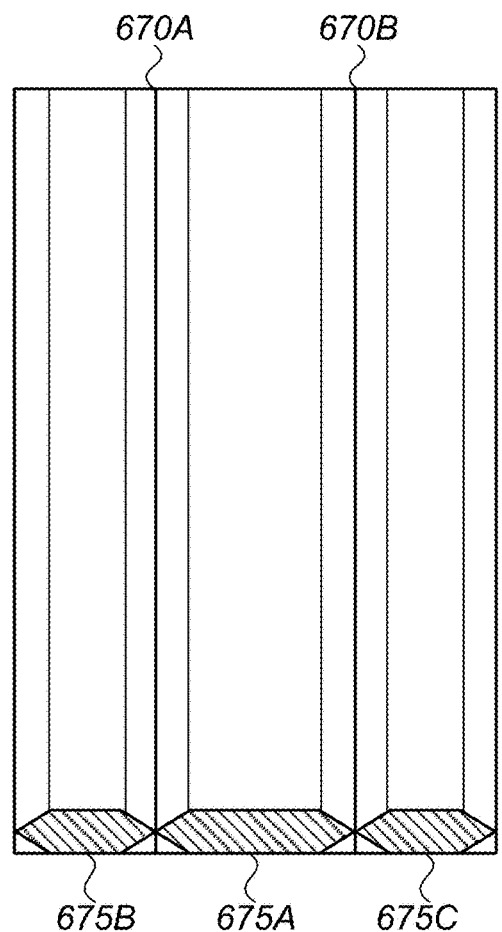
FIG. 6B is a top down view of a patient bed, according to an illustrative embodiment of the invention.
Figure 6C:
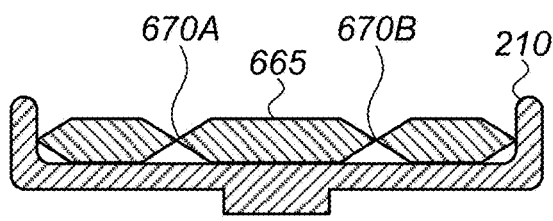
FIG. 6C and FIG. 6D are diagrams of a capsule incubator with a patient bed, according to illustrative embodiments of the invention.
Figure 6D:
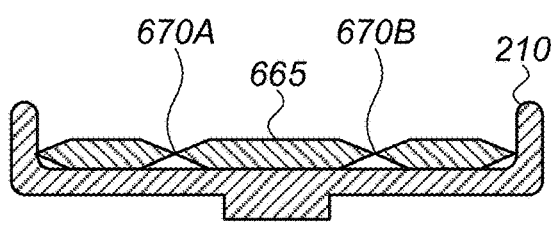

In some embodiments, the patient bed 250 is a foldable bed. FIG. 6A is a front view diagram of the capsule incubator 210 with a patient bed 665, according to an illustrative embodiment of the invention. FIG. 6B is a top down view of the patient bed 665, according to an illustrative embodiment of the invention. The patient bed 665 can include two pivot lines 670a and 670b, and a first portion 675a, a second portion 675b, and a third portion 675c. The baby can lie on the first portion 675a, and the second portion 675b and the third portion 675c can each rotate about its respective pivot line 670a and 670b such that the patient bed 265 can wrap around the baby. In some embodiments, the second portion 675b and the third portion 675c wrap around the baby when the first flap 225 and the second flap 230 of the capsule incubator 210 are closed. For example, the second portion 675b and the third portion 675c can be made of a soft material and manually wrapped around the baby.

In some embodiments, the patient bed 665 has multiple layers of materials. In some embodiments, one of the layers of the patient bed 665 can include a blanket. In some embodiments, the patient bed 665 can include a RF coil layer (not shown) that is positioned within a top layer (e.g., a cushioned fabric layer) and a bottom layer (e.g., a cushioned fabric layer) of the patient bed 665. The RF coil layer can be a rolled flexible printed circuit board (PBC). The size of the RF coil layer can depend on the body part to be imaged. The RF coil layer can be positioned such that when the second portion 675b and the third portion 675c of the patient bed 665 are wrapped around the baby, an RF coil is formed around a desired body part of the baby. For example, a RF coil layer can be positioned in the patient bed 665 such that when the second portion 675b and the third portion 675c are wrapped around the baby, an RF coil is formed around lungs of the baby. In some embodiments, the RF coil layer can be movable or stationary within the patient bed 265. For example, the RF coil layer can be an insert into the bed. In some embodiments, one or more temperature sensors are positioned within and/or on the patient bed 265, such that a temperature of the baby can be monitored.

Figure 7A:
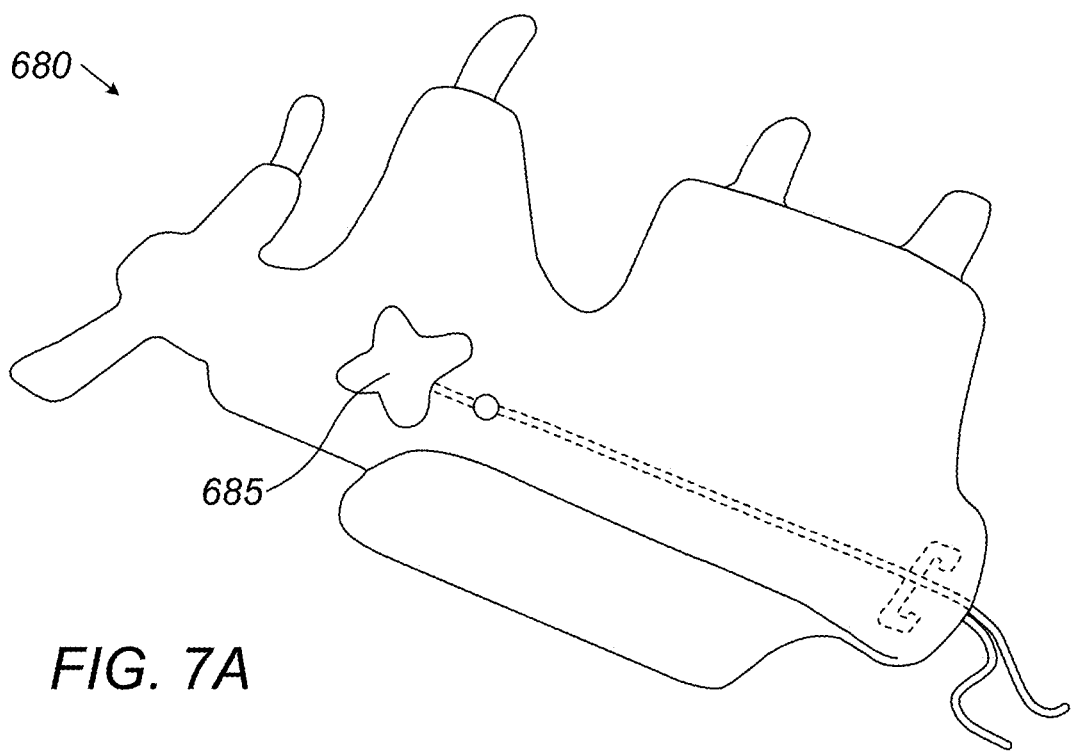
FIG. 7A shows an example of a wrap that has an RF coil embedded therein, according to an illustrative embodiment of the invention.
Figure 7B:
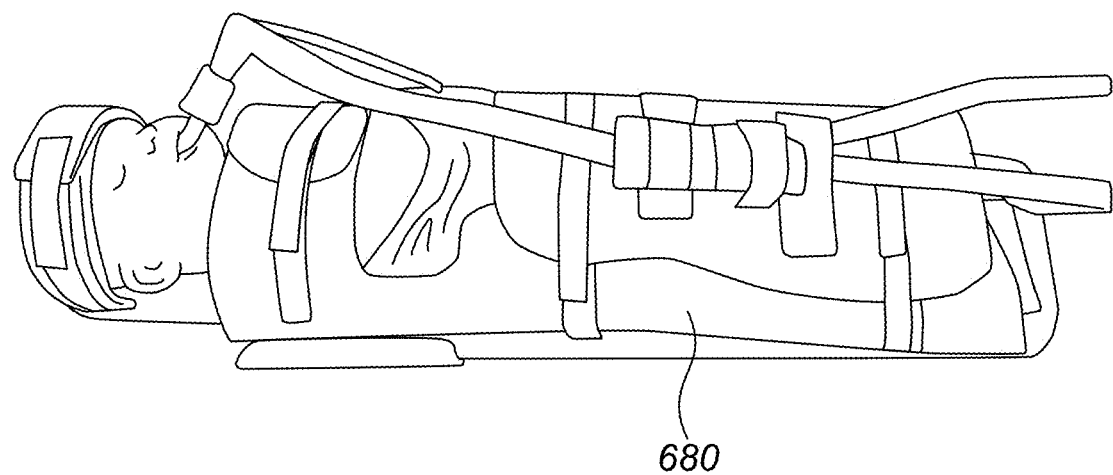
FIG. 7B shows an example of a wrap that has an RF coil embedded therein, according to an illustrative embodiment of the invention

In some embodiments, the baby is placed within a wrap. FIGS. 7A and 7B show an example of a wrap 680 that has an RF coil embedded therein, according to an illustrative embodiment of the invention. The wrap can include multiple layers of materials. In some embodiments, the wrap 680 can include a RF coil layer that is positioned within a top layer (e.g., a cushioned fabric layer) and a bottom layer (e.g., a cushioned fabric layer) of the wrap 680. The RF coil layer can be a rolled flexible printed circuit board (PBC). The RF coil layer can be positioned such that when wrap 680 is in position on the baby, an RF coil is formed around a desired body part of the baby. For example, a RF coil layer can be positioned in the wrap 680 such that when the wrap 680 is closed, an RF coil is formed around a head of the baby. In some embodiments, a temperature sensor 685 can be positioned within the wrap 680, such that the temperature of the baby can be monitored. In some embodiments, one or more sensors (e.g., temperature, motion, and/or oxygen) are positioned within and/or on the wrap 680, such that parameters of the baby can be monitored.

Positioning the RF coil within the patient bed 665 or the wrap 680 can result in an improved signal to noise ratio (SNR) due to, for example, a close proximity of the RF coil to the object to be imaged.

Figure 8A:
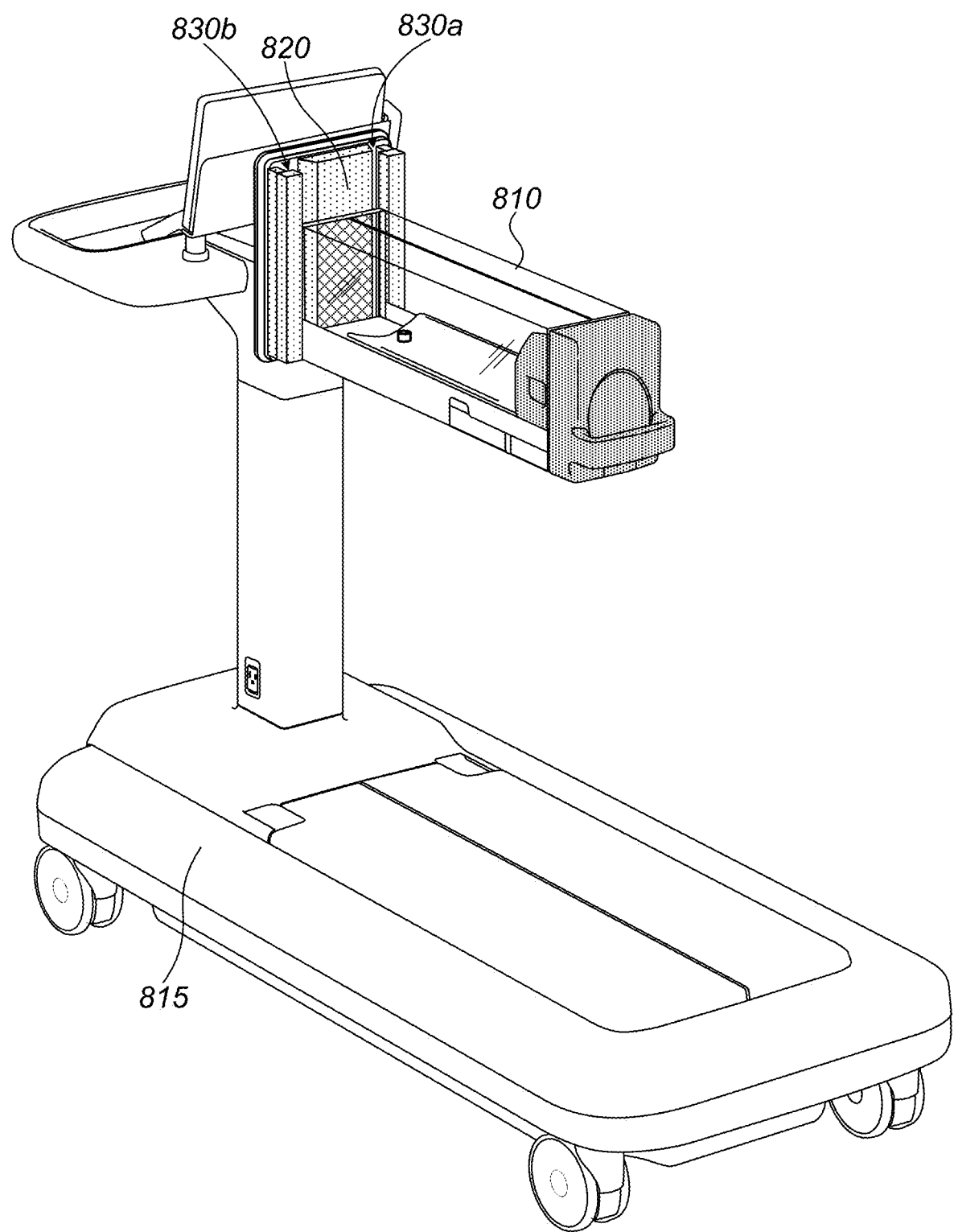
FIG. 8A is a diagram of a capsule incubator coupled to a cart via a RF shield structure, according to an illustrative embodiment of the invention.
Figure 8B:
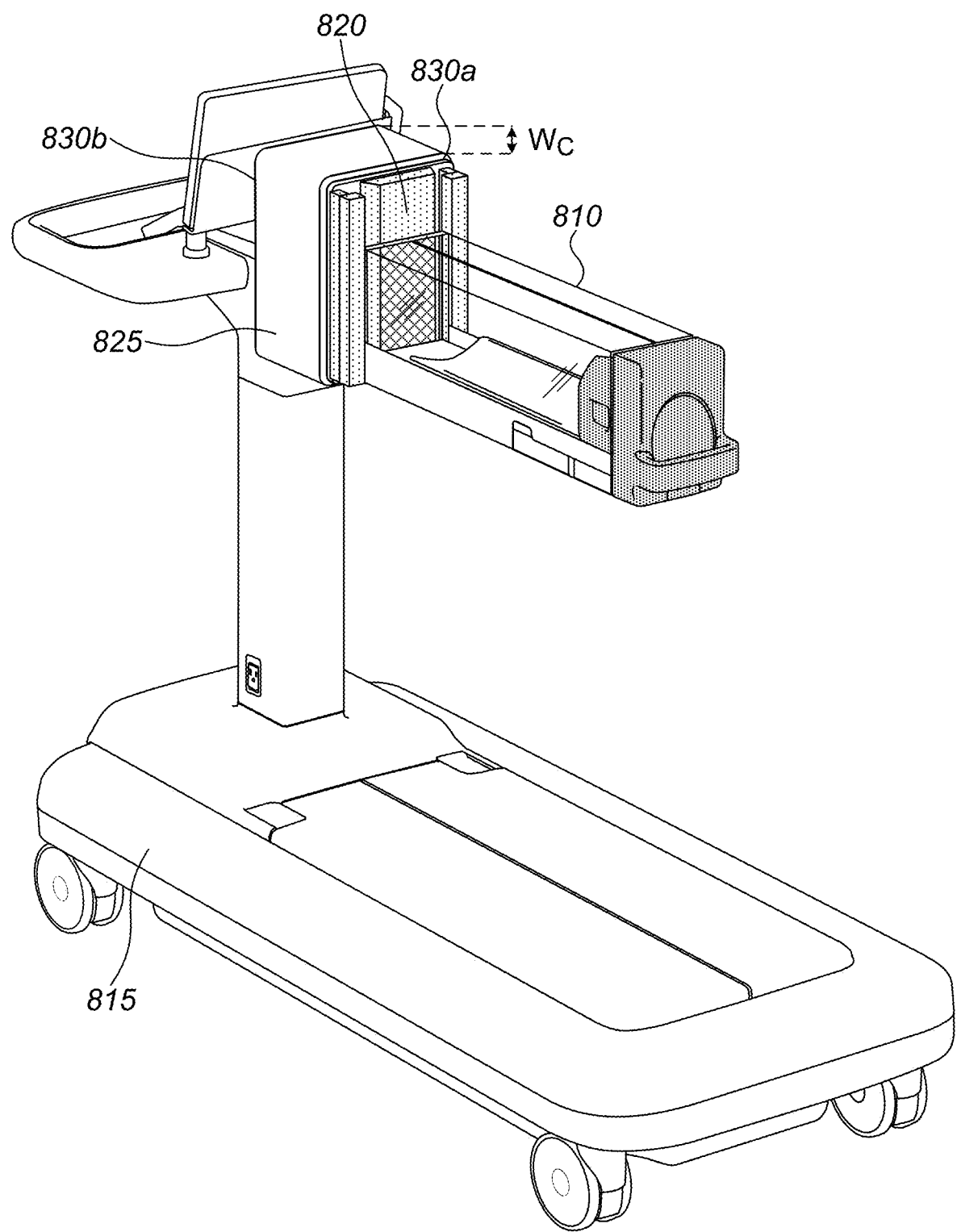
FIG. 8B is a diagram of the capsule incubator coupled to the cart via a connector, according to an illustrative embodiment of the invention.

Turning back to FIG. 2, the capsule incubator 210 can attach to a cart (e.g., the cart 120, as described above in FIG. 1). The capsule incubator 210 can attach to the cart 120 via a RF shield structure (e.g., the second surface 323 of the RF shield structure 320, as described above in FIG. 3B). FIG. 8A is a diagram of a capsule incubator 810 coupled to a cart 815 via a RF shield structure 820, according to an illustrative embodiment of the invention. In some embodiments, the capsule incubator 810 can attach to the cart 815 via a connector. FIG. 8B is a diagram of the capsule incubator 810 coupled to the cart 815 via the connector 825, according to an illustrative embodiment of the invention. The connector 825 can include a first surface 830a that faces the capsule incubator 810 and a second surface 830b that faces the cart 815. The first surface 830a can mate with the capsule incubator 810 or the RF shield structure 820. For example, via mating structures as are known in the art. The second surface 820b can mate with the cart 815. For example, via mating structures, as are known in the art.

The connector 825 can have a width $W_C$. The width $W_C$ can depend on where the capsule incubator 810 is to be positioned within an imaging device. For example, as shown below in FIG. 11B, the capsule incubator 810 can be inserted into a MRI having a bore sized such that the capsule incubator 810 can be positioned with one end very close to the bore entrance (e.g., a length and a width substantially equal to a length and a width of the bottom portion of the capsule incubator, as described above in FIG. 2). In another example, the capsule incubator 810 can be inserted into a MRI having an open bore such that the capsule incubator 810 can be positioned a distance from the bore entrance (e.g., 1.5 feet to 5 feet). There can be multiple connectors 825 each having different widths W such that the capsule incubator 810 can be positioned in multiple imaging devices without having to detach the capsule incubator 810 from the cart 815.

Figure 8C:
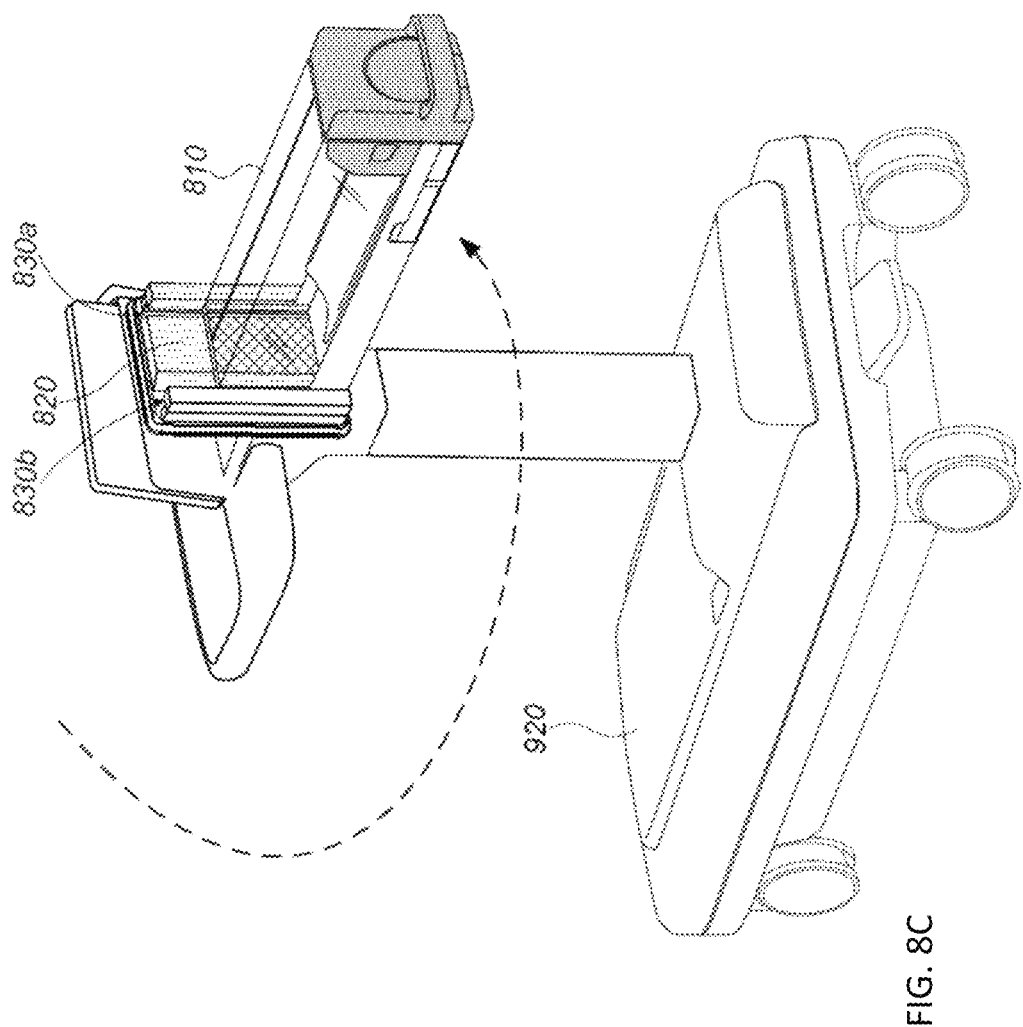
FIG. 8C is a diagram of the capsule incubator coupled to the cart, according to an illustrative embodiment of the invention.

In some embodiments, the capsule incubator 810 is rotated about the pillar such that the capsule incubator 810 extends away from the cart 920, as is shown in FIG. 8C. In these embodiments, when the capsule incubator 810 is pushed into the MRI, the cart 920 does not need to dock under the MRI. In this manner, the cart can be used to transport the capsule incubator to imaging devices that do not allow for the cart bottom to be docked under the imaging device.

Figure 9A:
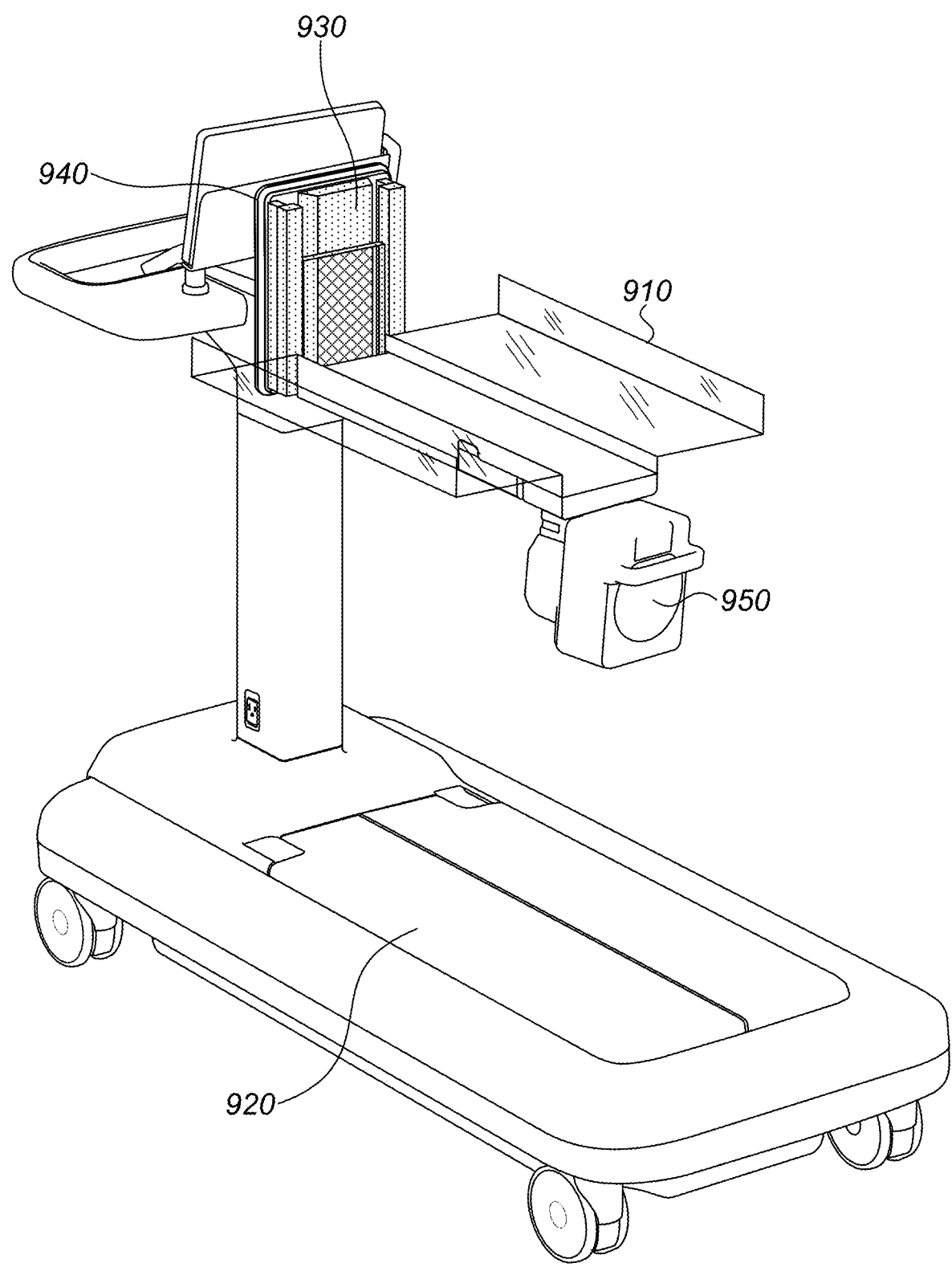
FIG. 9A is a diagram of a capsule incubator coupled to a cart via a RF shield structure and connector, with an RF coil positioning system, according to an illustrative embodiment of the invention.
Figure 9B:
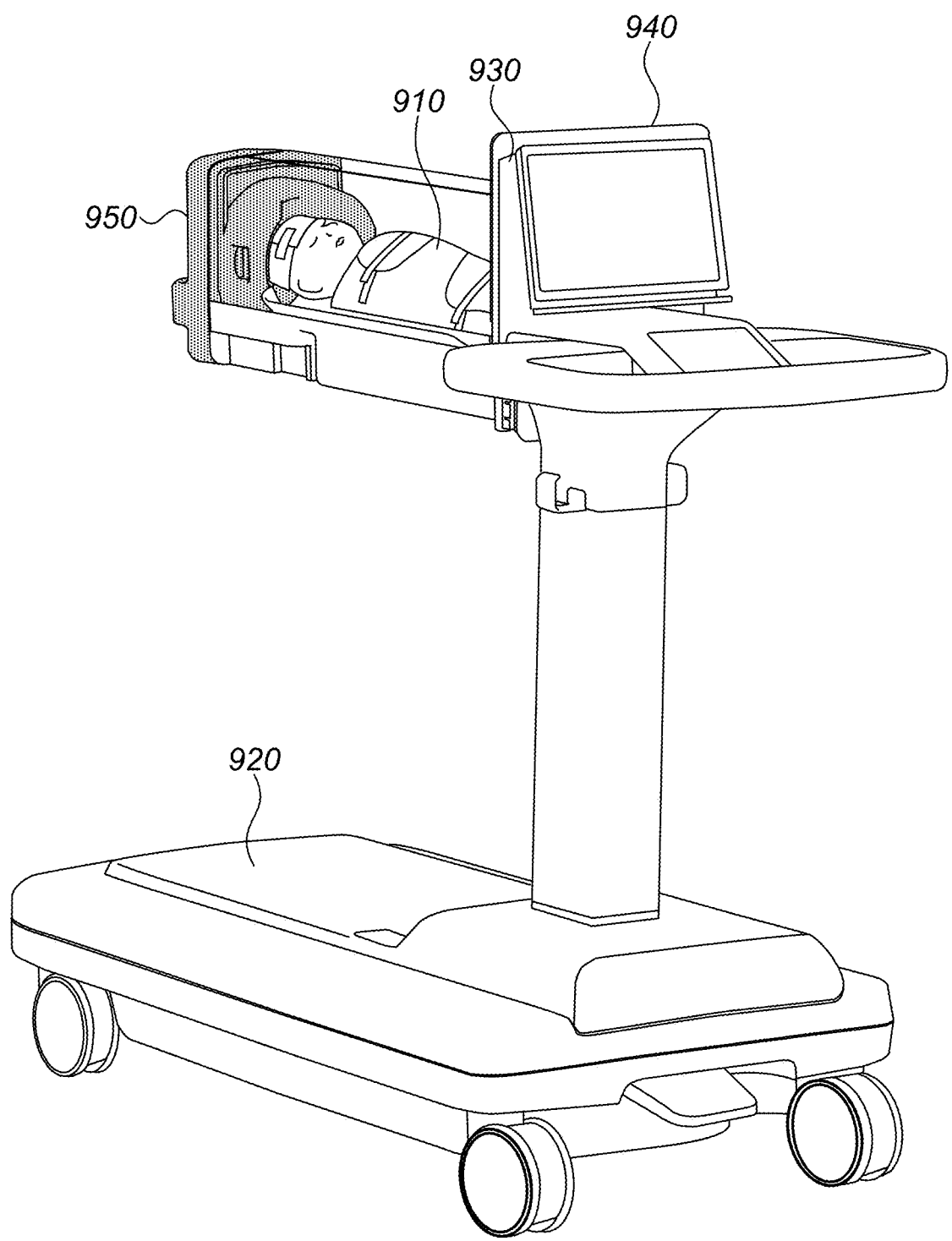
FIG. 9B is a diagram of the capsule incubator of FIG. 9A attached to the cart of FIG. 9A via the RF shielded structure of FIG. 9A and connector of FIG. 9A, with the RF coil positioning system of FIG. 9A, according to an illustrative embodiment of the invention.
Figure 9C:
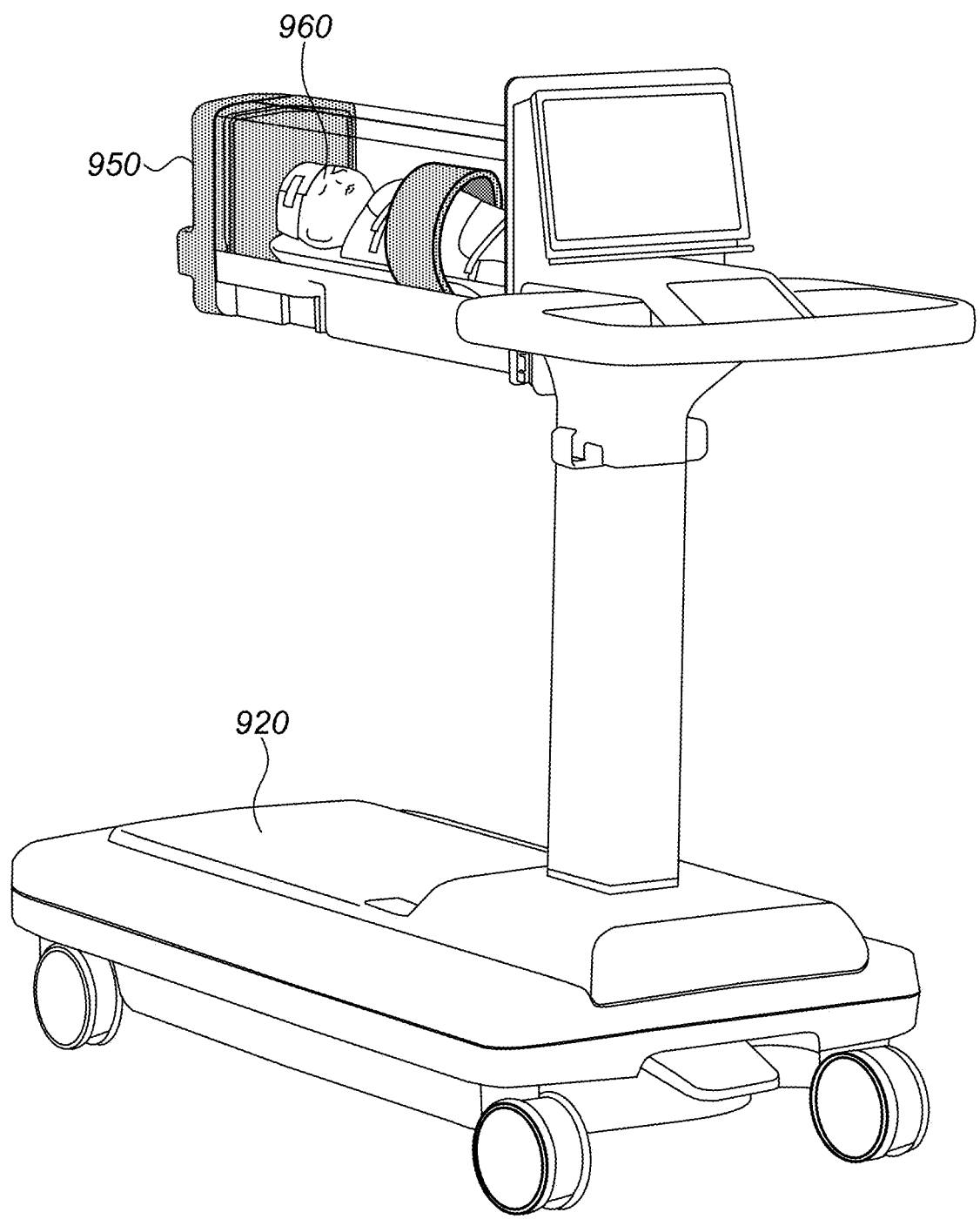
FIG. 9C is a diagram of the capsule incubator of FIG. 9A attached to the cart of FIG. 9A via the RF shielded structure of FIG. 9A with an RF coil positioned around a neonate, according to an illustrative embodiment of the invention.

FIG. 9A is a diagram of a capsule incubator 910 coupled to a cart 920 via a RF shield structure 930 and connector 940, with an RF coil positioning system 950 positioned under the capsule incubator 910, according to an illustrative embodiment of the invention. The capsule incubator 910 is in an open configuration. The RF coil positioning system 950 can rotate between being positioned under the capsule incubator 910 and positioned such that it can slide into the capsule incubator 910 (e.g., as described above in FIGS. 4A and 4B). FIG. 9B is a diagram of the capsule incubator 910 attached to the cart 920 via the RF shielded structure 930 and connector 940, with the RF coil positioning system 950 positioned around a head of a baby 960 within the capsule incubator 910, according to an illustrative embodiment of the invention. The capsule incubator 910 is in a closed position. FIG. 9C is a diagram of the capsule incubator 910 attached to the cart via the RF shielded structure 930, have a first end 955, according to an illustrative embodiment of the invention. In FIG. 9C, a RF coil 965 is positioned around a mid-section of the neonate. As is apparent to one of ordinary skill in the art, an RF coil can be positioned around any body part of the neonate to be imaged.

In some embodiments, the capsule incubator includes a safety mechanism to support a first and/or second flap of the capsule incubator in an open position. FIGS. 9E and 9D are an example of a support 980 that extends out from a bottom the capsule incubator 210 such that when a flap of the capsule incubator is in an open position, the flap can rest on the support 980. The support 980 can allow for additional weight to be positioned on the flap (e.g., the baby), without the flap breaking. In some embodiments, there is a support for each of the two flaps. In some embodiments, there are two supports to support each flap. As is apparent to one of ordinary skill in the art, additional supports can be included to increase the weight the respective flap can bear.

In some embodiments, the support is a flap that extends the entire length of the capsule incubator.

Figure 10:
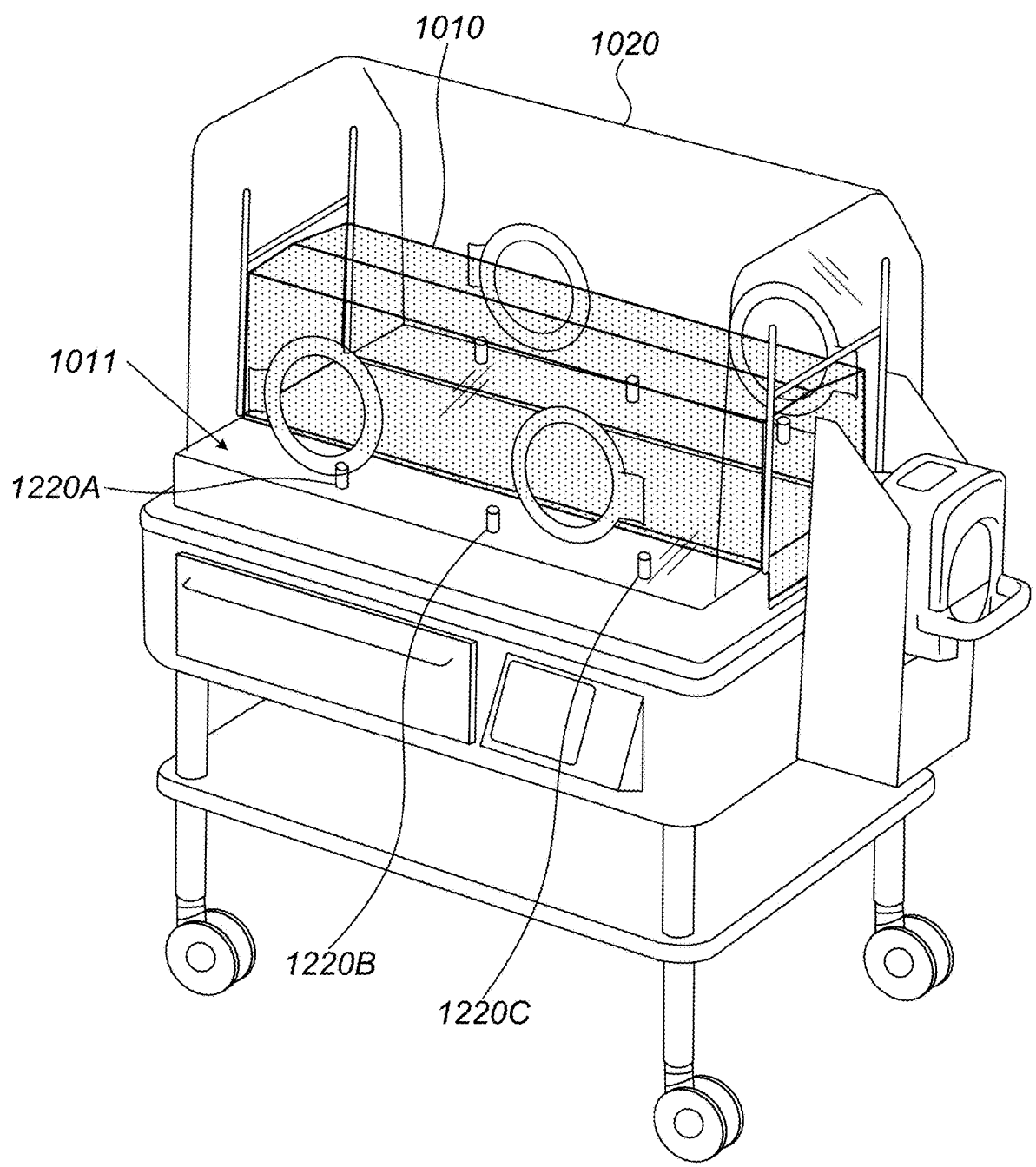
FIG. 10 is a diagram of a capsule incubator docked in a dock incubator, according to an illustrative embodiment of the invention.

Turning back to FIG. 2, in some embodiments, the capsule incubator 210 is inserted into a dock incubator (not shown). FIG. 10 is a diagram of a capsule incubator 1110 docked in a dock incubator 1020, according to an illustrative embodiment of the invention. The dock incubator 1020 can have an indent 1015 that can receive the capsule incubator 1110. In this manner, the capsule incubator 1110 can be positioned in an exact location the dock incubator 1020. In various embodiments, the bottom portion 1117 of the capsule incubator 1110 includes a recess (not shown) and the dock incubator 1020 includes a track (not shown) such that the capsule incubator 1110 slides into a predetermined position within the dock incubator 1020. In some embodiments, the bottom portion 1117 of the capsule incubator 1110 and the dock incubator 1020 includes any mechanism as is known in the art to cause the capsule incubator 1110 to dock at a particular location within the docking incubator 1020.

Figure 11A:
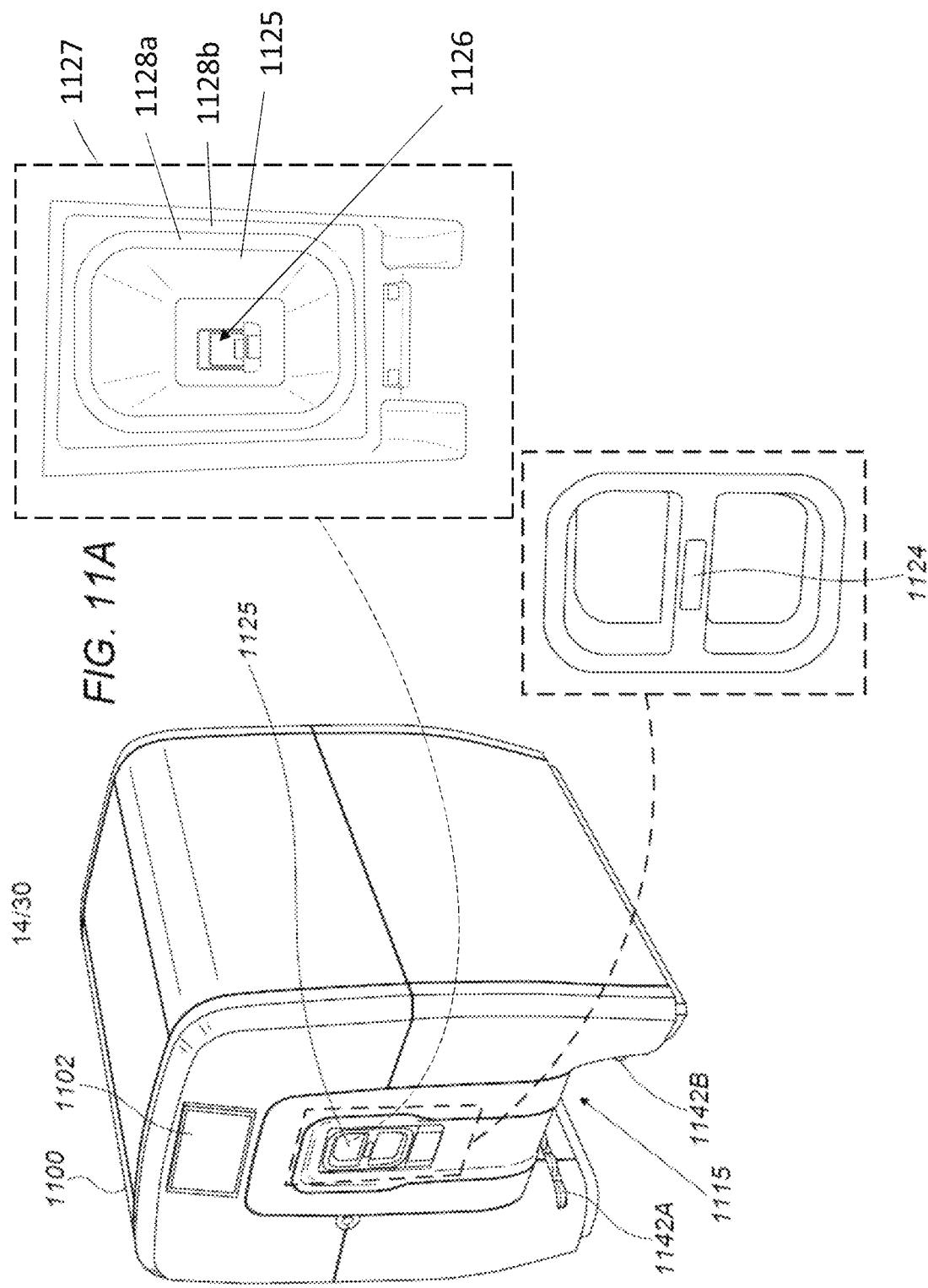
FIG. 11A is a diagram of a MRI device that can receive a capsule incubator, according to an illustrative embodiment of the invention.

Turning back to FIG. 2, in some embodiments, the capsule incubator 210 is inserted into a MRI device having a bore that receives the capsule incubator 210. FIG. 11A is a diagram of a MRI device 1100 that can receive a capsule incubator 1110, according to an illustrative embodiment of the invention. The MRI device 1100 can include a bore 1125 and a recess 1115. The bore 1125 can receive the capsule incubator 1110 and the recess 1115 can receive a horizontal base 1117 of the cart 1140, as shown in FIG. 11B. Blow up 1127 shows an example of the bore without the bore plug 1124 positioned there. The bore 1125 can include a connector 1126 that can couple with one or more connectors on the RF positioning system (e.g., the one or more connectors 470, as described above). The surfaces of the bore 1128a, 1128b can mate with the surfaces of the RF shielding structure, such that the access port 342 is substantially closed to form a closed tubular like structure for one or more medical devices to remain connected to a baby while within the MRI.

In some embodiments, the MRI device 1100 includes an anti-slam locking system as described in further detail below with respect to FIG. 11H. The recess 1115 can include tracks 1142a and 1142b to receive the bottom portion 1117. The MRI 1100 can include a bore plug 1124 that can be used to close the bore 1125 when the capsule incubator 1110 is not inserted therein. In some embodiments, the bore 1125 and the bore plug 1124 size is based on the size of the capsule incubator 1110.

A housing of the MRI device 1100 can be made of a material that shields an environment exterior to the MRI device 1100 from the magnetic fields generated by magnets (e.g., magnetic fringe fields), such as permanent magnets, within the MRI device 1110 and RF energy generated by one or more RF coils within the MRI device 1100 or inserted into the MRI device (not shown). The housing of the MRI device 1100 can also prevent magnetic fields and RF energy exterior to the MRI device 1100 from entering the MRI device 1100, and thus causing interference in the imaging results. The MRI device 1100 can be a permanent magnet based MRI. The MRI device 1100 can be an MRI device as described in U.S. Pat. Nos. 7,400,147 and/or 7,315,168, both of which are incorporate herein by reference in their entireties.

The MRI device 1100 can include a video display 1102. The video display 1102 can display an image of a baby when the capsule incubator 1110 is within the MRI device 1100. In this manner, the baby can be visually monitored when inside of the MRI device 1100. The placement of the camera within the MRI device 1100 can be as is describe in U.S. patent application Ser. No. 15/402,437, incorporate herein by reference in its entirety.

Turning to FIG. 11B, an end 1120 of the capsule incubator 1110 that connects to the cart 1140 can mate with the bore 1125 of the MRI device 1100 in a manner that can allow the end 1120 to close the bore 1125 of the MRI device 1100. The end 1120 of the capsule incubator 1110 can be made of a material that shields an environment exterior to the MRI device 1100 from the magnetic fields generated by magnets within the MRI device 1100 and/or RF energy generated by the RF coils within the MRI device 1100. The end 1120 of the capsule incubator 1110 of the MRI device 1100 can also prevent magnetic fields and/or RF energy exterior to the MRI device 1100 from entering the MRI device 1100, and thus causing interference in the imaging results.

The end 1120 of the capsule incubator 1110 can include an RF shield structure (e.g., the RF shield structure 320, as described above in FIG. 3B). The RF shield structure 330A can allow for tubes attached to the baby to remain attached to the baby while the baby is inserted into the MRI device 1100 via the capsule and the cart, and allow the tubes to extend between inside and out of the MRI device 1100 without magnetic and/or RF leakage.

Because the RF shielding structure and the MRI device 1100 shields an environment outside of the MRI device 1100 from the magnetic fields and RF fields inside of the MRI device 1100, and vice versa, the MRI device 1100 can be positioned at any location (e.g., within a baby intensive care unit (NICU) in a hospital or within a baby delivery unit), eliminating the requirement for an MRI room. The hours typically required to prepare the baby for an MRI (e.g., removing/replacing life support with MRI life support equipment, removing the baby from its incubator environment, transporting the baby in a transport incubator and/or transporting the baby into the MRI device) can be reduced to minutes with the MRI device collocated in a room with the baby, and without needing to remove/reconnect the baby's life support equipment or move the baby from its environment.

Figure 11C:
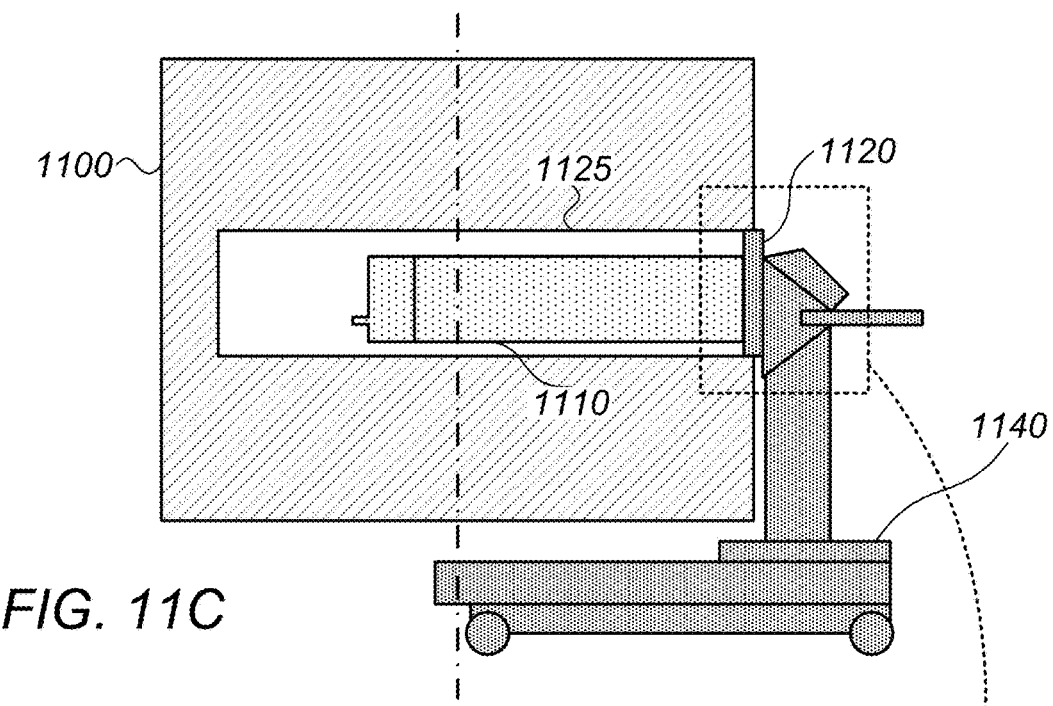
FIG. 11C is a side view diagram of an end the capsule incubator of FIG. 11B having an RF shielding structure mating with the bore of the MRI device of FIG. 11A, according to an illustrative embodiment of the invention.
Figure 11D:
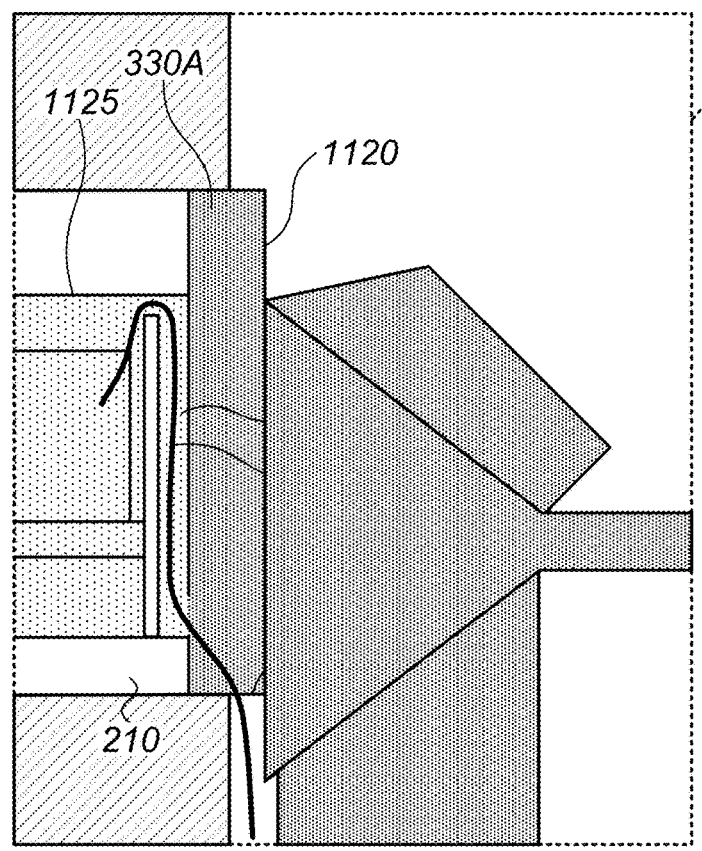
FIG. 11D is a diagram of tubing extending between the MRI device and capsule incubator of FIG. 11C and an exterior environment, according to an illustrative embodiment of the invention.

FIG. 11C is a side view of the end 1120 the capsule incubator 1110 having an RF shielding structure 330A mating with the bore 1125 of the MRI device 1100, according to an illustrative embodiment of the invention. When the capsule incubator 1110 is inserted into the MRI device 1100, the RF shielding structure 330A mates with and substantially closes the bore 1125 of the MRI device 1100. As shown in more detail in FIG. 11D, medical tubing 1140 can extend from an interior of the bore 1125 of the MRI device 1100 through the RF shielding structure 330A to a location exterior to the MRI device 1100.

Figure 11E:
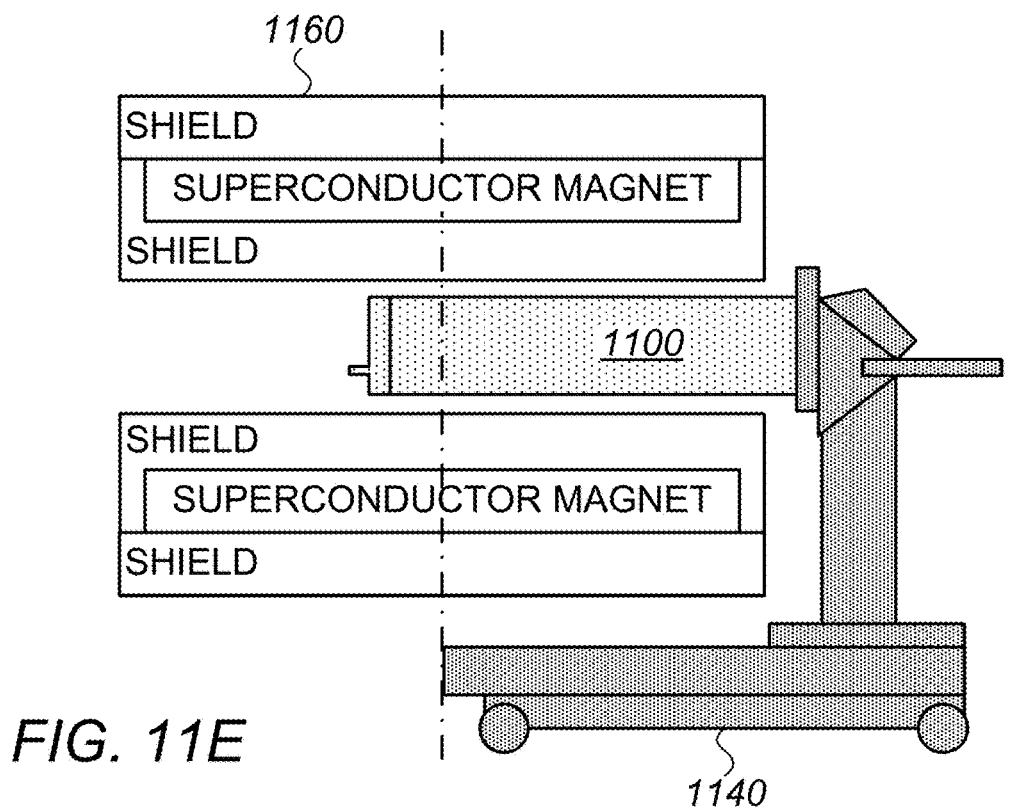
FIG. 11E is cross-sectional side view of a superconductor MRI device where the cart is used to transport the capsule incubator to the MRI device, according to an illustrative embodiment of the invention.

In some embodiments, the capsule incubator 1110 and/or cart 1140 are used to transport the capsule to a MRI device 1100 where neither the end 1120 of the capsule incubator 1110 nor the cart 1140 close a bore of the MRI device 1100. FIG. 11E is cross-sectional side view of an MRI device 1160 (e.g., superconductor MRI device as is known in the art) where the cart 1140 is used to transport the capsule incubator 1110 to the MRI device 1160.

Figure 11F:
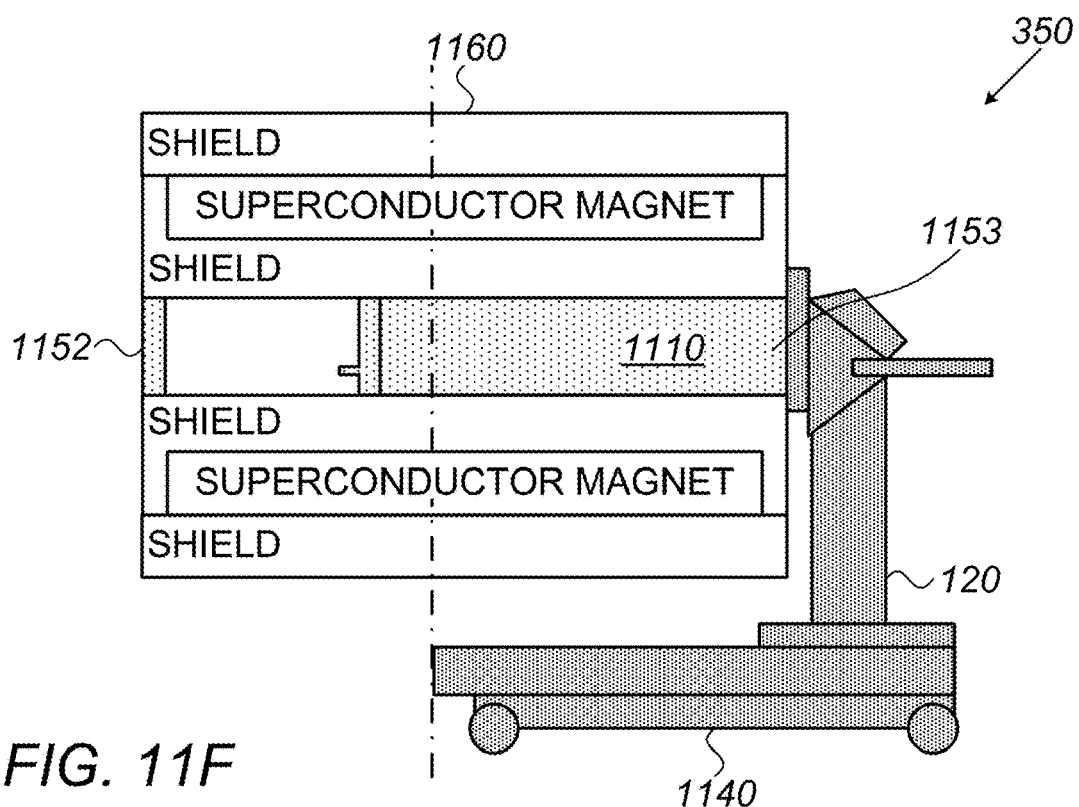
FIG. 11F is a diagram of the capsule incubator coupled to the cart and inserted into a superconductor magnet MRI device, according to an illustrative embodiment of the invention.

FIG. 11F is a diagram of the capsule incubator 1110 coupled to the cart 1140 and inserted into a superconductor magnet MRI device 1160, according to an illustrative embodiment of the invention. In some embodiments, the superconductor magnet MRI device 1160 can include a first RF and magnetic shielding door 1152 and a second RF and magnetic shielding door 1152. The RF and magnetic shielding doors 1152 and 1153 can be made of a material that substantially shields RF and magnetic fields. The door 1152 can include an opening (not shown) that allows the RF shielding structure coupled to the capsule incubator 1110 to seal the opening of the door 1152 such that the RF and magnetic radiation does not enter/exit the superconductor magnet MRI device 1160. The doors 1152 and 1153 can be retrofit onto existing superconductor magnet MRI devices. In this manner, superconductor magnet MRI devices can be removed from MRI shielded rooms, and put in any location for imaging a baby within the capsule incubator 1110.

In some embodiments, the capsule incubator 1110 can be disconnected from the cart 1140 and placed within the MRI device 1160, as is shown in FIG. 11G. In some embodiments, the doors 1152 and 1153 can both be retrofit and can be RF and magnetic shielding doors. At least one of the two shielding doors 1152 and 1153 can include two openings and a conduit having a length to width ratio (e.g., 5 to 1) such that medical tubing can extend from an interior of the MRI device 1160 to an exterior of the MRI device 1160 and RF and magnetic shielding substantially maintained.

In some embodiments, at least one of the doors 1152 and 1153 is made of a honeycomb tubing or mesh material, such that air can be flowed through the bore 1125 of the MRI device 1160 to, for example, allow for temperature and/or humidity control within the bore 1125. In some embodiments, at least one of the two shielding doors 360 can include a RF shielded sleeve, such that the capsule incubator 1110 is inserted into the MRI device via the sleeve. In these variations, each tube of the honeycomb tubing, each hole in the mesh, and or the sleeve can adhere to a length to width ratio for RF shielding (e.g., 5 to 1).

As is shown in FIGS. 11E, 11F, 11G, MRI of a baby disposed within the capsule incubator 1110 can be performed with an existing MRI device (e.g., superconductor MRI as is known in the art), without removing the medical tubes of the baby. MRI of a baby can be performed without having the MRI in an RF shielded room (e.g., aluminum shield). As is known in the art, RF shielding an MRI room is very expensive, thus an ability to perform an MRI within a generic room, rather than in an RF shielded room, can provide significant cost savings and/or allow doctor's offices, smaller hospitals and/or urban hospitals lacking space to perform MRI imaging.

Transporting the baby within the capsule via the cart can provide a constant environment for the baby and prevent medical personnel from having to sterilize one or more environments and/or equipment during transport and/or imaging of the baby. Transporting the baby within the capsule via the cart can also provide a less physically challenging mechanism for transporting the baby (e.g., less heavy, less bulky, require less personnel to move, etc.)

FIG. 11H is a diagram of an anti-slam locking system 1190, according to an illustrative embodiment of the invention. The anti-slam locking system 1190 can include a hydraulic piston 1191 attached to the MRD device 1160 and a collet 1192 attached to the cart 1140. During operation, when the cart 1140 is moved into the recess 1115 of the MRI device 1160, the hydraulic piston 1191 and the collet 1192 mate such that even the cart 1140 is pushed with great force, the cart 1140 slows down as it approaches its final position within the recess 1115 of the MRD device 1160. In this manner, even if the cart 1140 is forcefully pushed, a baby in the capsule incubator can experience a smooth transition into the MRD device 1160.

Figure 11I:
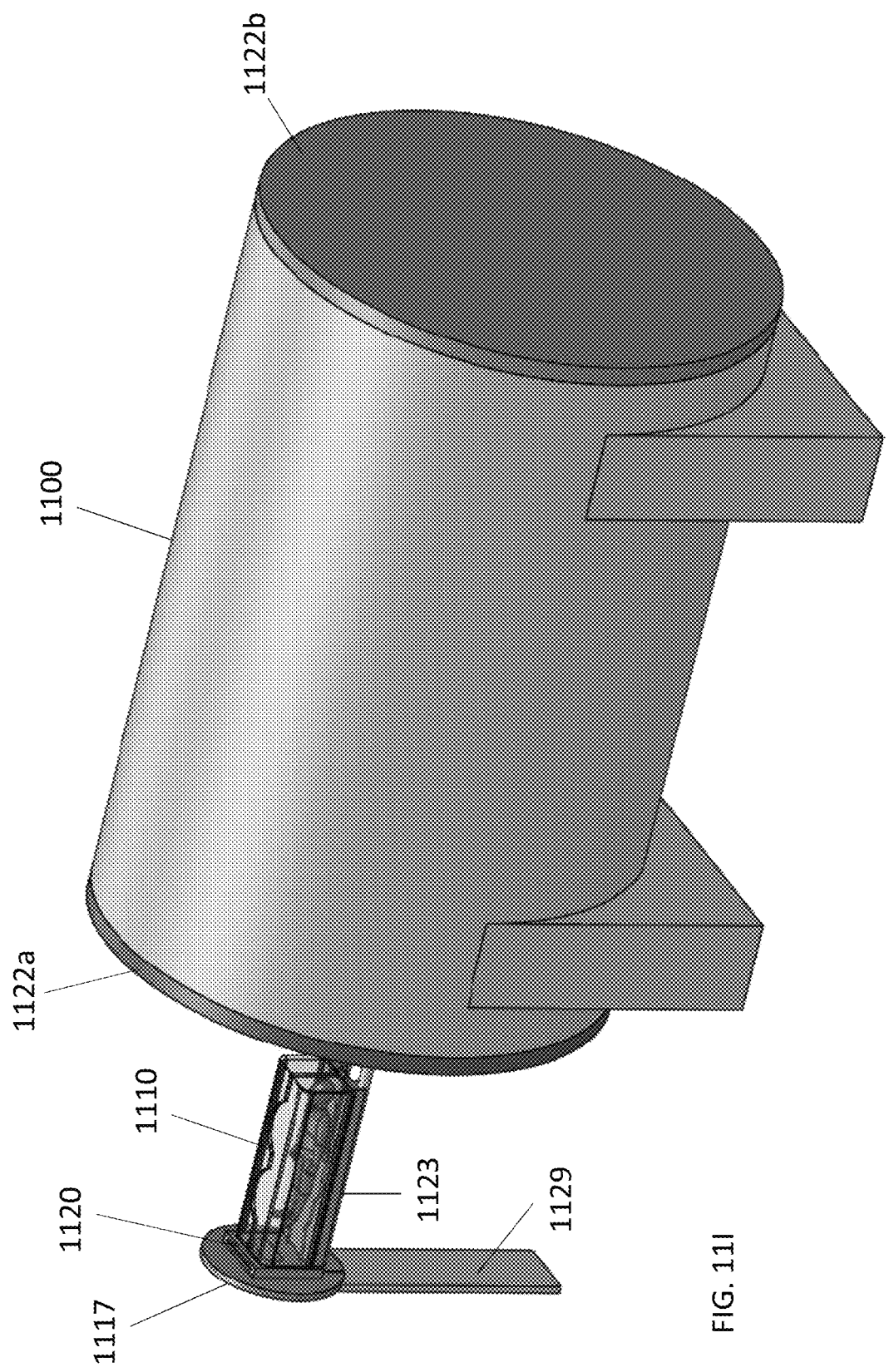
FIGS. 11I, 11J, and 11K are diagrams of a superconductor MRI device where a capsule is inserted into the superconductor MRI device, according to illustrative embodiments of the invention.
Figure 11K:
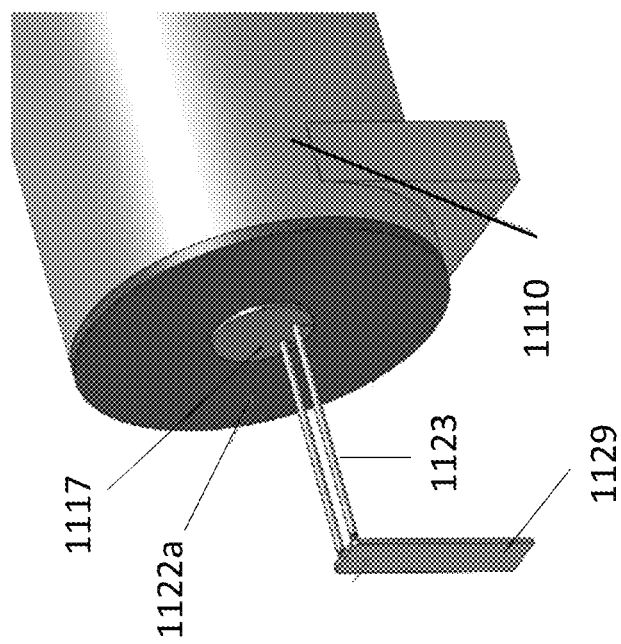
Figure 11J:
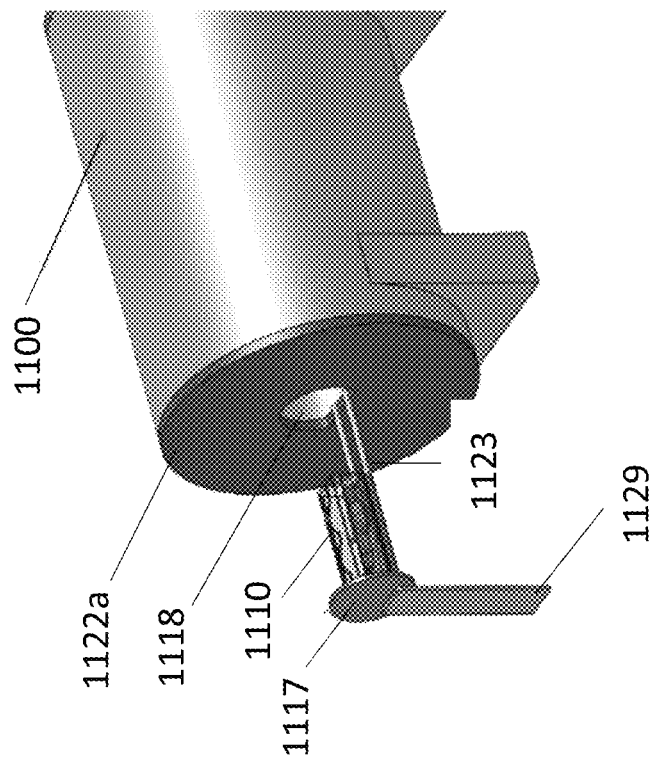

FIGS. 11I, 11J, and 11K are diagrams of a superconductor MRI device 1100 where a capsule 1110 is inserted into the superconductor MRI device 1100, according to illustrative embodiments of the invention. The superconductor MRI device 1100 can include two doors 1122a and 1122b, respectively. The door 1122a can include a bore 1118. The capsule 1110 can be inserted into the bore 1118 into the MRI device 1100. The bore 1118 can be electrically and magnetically sealed by an end 1117. The end 1117 can include the RF shield structure 1120. The end 1117 can be coupled to a support 1129. The end 1117 coupled to the capsule 1110 can slide into the superconductor MRI device 1100 via a guide rail 1123. In some embodiments, the end 1117 and the RF shield 1120 are coupled to a cart (e.g., the cart as shown in FIG. 8C as described above), and the cart is used to position the capsule in the superconductor MRI device 1100.

FIG. 11F is a diagram of the capsule incubator coupled to the cart and inserted into a superconductor magnet MRI device, according to an illustrative embodiment of the invention.

FIG. 12A is a diagram of a cart 1220 and capsule for transporting a capsule incubator 1210, according to an illustrative embodiment of the invention. The cart 1220 can include a horizontal base 1225, a pillar 1230, a connector 1245, a control panel 1250 and four wheels 1255.

The horizontal base 1225 can include a storage compartment 1260. The four wheels 1255 can be coupled to the horizontal base 1225. In various embodiments, the horizontal base 1225 has less than four wheels, three wheels, and/or two large wheels. The horizontal base 1225 can include a brake pedal (not shown). The brake pedal can cause the cart 1220 to stop when depressed.

The pillar 1230 can be coupled to the horizontal base 1225 and extend vertically from the horizontal base 1225. The pillar 1230 can include an electric power socket 1232, an air inlet 1233, and/or a grommet (note shown). In some embodiments, the pillar 1230 includes a clip (not shown) such that tubing extending from the baby in the capsule incubator through the RF shielding structure can be stabilized. The stabilization can ensure, for example, that unwanted movement of the tubing does not occur, such that tubes connected to the baby are not moved. For example, if the baby has IV tubing, it can be important that the tubing remain in the same place as to not tug on the baby.

FIG. 12B is a diagram of the air inlet 1233, according to an illustrative embodiment of the invention. The air inlet 1233 can allow for an air suction mechanism (e.g., a fan) positioned within the pillar 1230 to pull fresh air into the pillar 1230 which can then be circulated into the capsule incubator 1210 (e.g., via the RF shield 345, as described above in FIG. 3B). The air inlet 1233 can also allow heated and/or cooled air (e.g., heated via a heater in the pillar 1230 and/or cooled via an air conditioner in the pillar 1230) to enter the incubator.

FIG. 12C is a diagram of the electric power socket 1232, according to an illustrative embodiment of the invention. The electric power socket 1232 can allow the cart 1220 to receive power from an AC or DC power source (e.g., a standard AC wall outlet and/or a portable AC or DC charging device). The control panel 1250 and/or air suction/air outlet can receive power from the electric power socket 1232. In some embodiments, the pillar 1230 is telescopic such that the height of a capsule incubator coupled to the cart 1220 is adjustable.

The cart 1220 can include a handle 1265 and/or a display 1252. FIG. 12D is a diagram of the handle 1265, the display 1252, and the control panel 1250, according to an illustrative embodiment of the invention. The display 1252 can be a touch screen. The control panel 1250 can have the following functions: a) turn the bed on and off; b) set temperature inside of the capsule incubator; c) display visual and/or audio alert signals; d) display indicators regarding power and/or docking status; e) adjust alert volume; and/or f) turn a light inside of the capsule incubator on and off.

In some embodiments, the alert indicates that the difference between a temperature of the RF shielding structure and flaps is greater than a threshold (e.g., 2-10 degrees), thus indicating that the flaps may not be sufficiently closed. In some embodiments, the alert indicates that air temperature inside of the capsule incubator is greater than the air temperature set by an operator by a threshold (e.g., 3 degrees). In some embodiments, the alert indicates that the temperature inside of the capsule incubator is greater than an allowable threshold (e.g., 38 degrees Celsius). In some embodiments, the alert indicates that the temperature inside of the capsule incubator is below than an allowable threshold (e.g., 3 degrees Celsius). In some embodiments, the alert indicates that a fan in the capsule incubator has stopped working. In some embodiments, the alert indicates an obstruction of air flow in the capsule incubator. In some embodiments, the alert indicates a low battery condition (e.g., when the cart is connected to a portable power supply). In some embodiments, the alert indicates a system fault (e.g., the scan did not complete).

The cart 1220 can be made of a RF and magnetic field shielding material, or from non-magnetic materials, such that any computer equipment, life support equipment or any objects stored within a body of the cart 1140 can be shielded from the magnetic field and/or RF field of the MRI device.

In some embodiment, the cart 1220 and any other equipment outside the capsule are made from non-magnetic materials such that they can be used in an environment of an MRI device with an external magnetic field, such as a super conductor MRI device.

FIG. 13A is an example of a dock incubator 1300, in accordance with an illustrative embodiment of the invention. The dock incubator 1300 can include two doors 1313a and 1313b, one or more access ports 1312, one or more knobs 1325 and a protrusion 1350.

The two doors 1313a and 1313b can be vertical sliding doors as shown. In various embodiments, the two doors 1313a and 1313b are horizontal sliding doors, swinging doors, and/or other doors as are known in the art. The two doors 1310a and 1310b can be automatically or manually actuated.

The one or more access ports 1312a, 1312b, . . . , 1312n, generally 1312, can be positioned at various locations of the dock incubator 1300. The access ports 1312, can allow for inserting of hands and/or medical equipment into the dock incubator 1300 without substantially disturbing the environment inside of the incubator 1300. In some embodiments, the two doors 1313a and 1313b each include an access port (not shown).

The dock incubator 1300 can include a protrusion 1350 (e.g., or any type of connection guide) positioned to mate with a recess (e.g., the recess 1015 as shown in further detail in FIG. 10) of the capsule (not shown), such that when the capsule is inserted into the dock incubator 1300, the capsule is guided into a particular position within the dock incubator 1300. The protrusion 1350 and recess can be any mate able mechanism as is known in the art for coupling two objects into a particular position.

The one or more knobs 1325a, 1325b, . . . . 1325n, generally 1

325, can be positioned such that when flaps (e.g. first flap 225 and second flap 230 as described above in FIG. 2) of the capsule incubator are completely open, the first flap and second flap rest on top of the one or more knobs 1325.

Figure 13B:
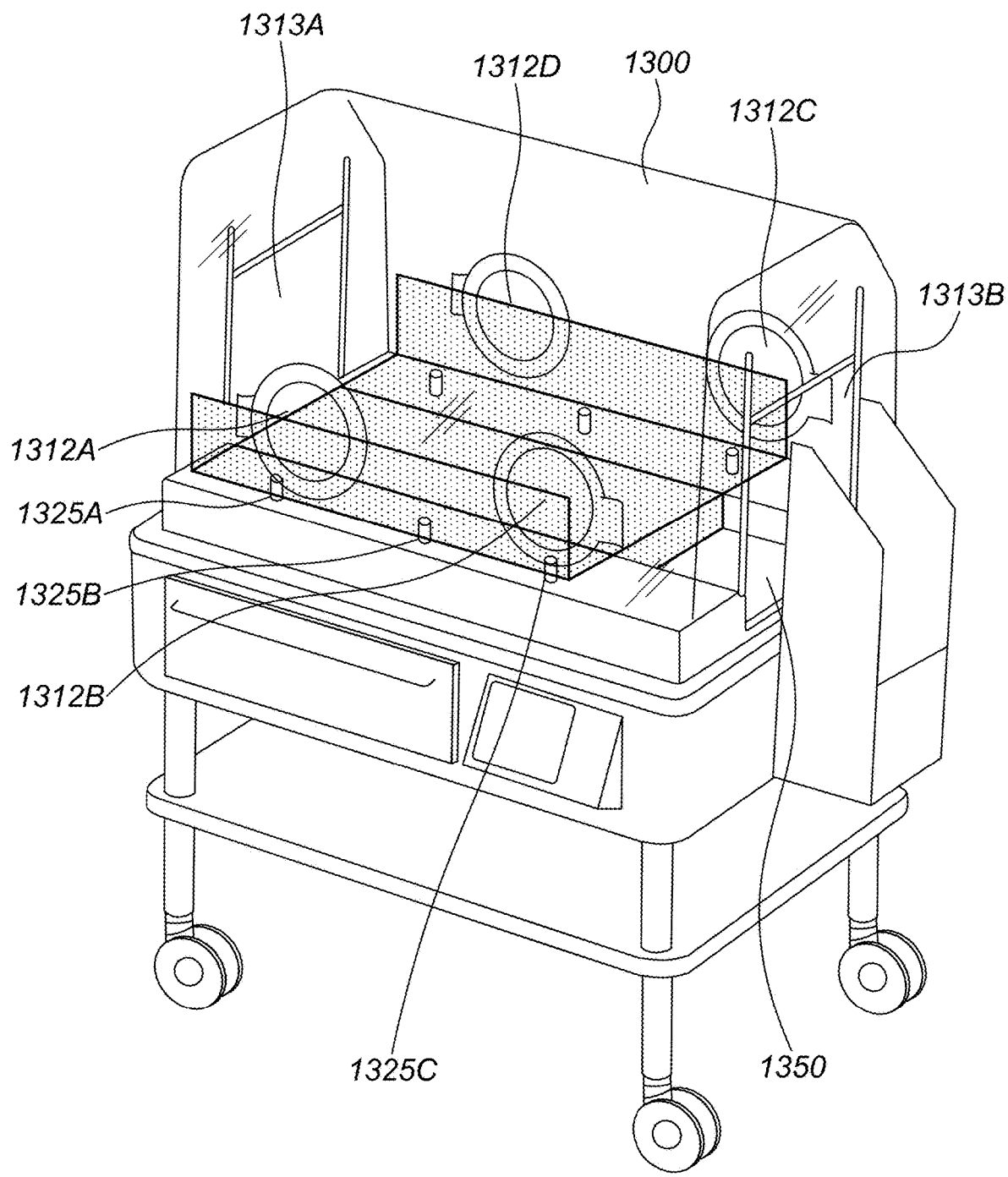
FIG. 13B is a cross sectional view of the dock incubator of FIG. 13A with capsule incubator flaps of a capsule resting on knobs, according to an illustrative embodiment of the invention.

FIG. 13B is a cross sectional view of the dock incubator 1300 with capsule incubator flaps 1355a and 1355b of a capsule 1310 resting on knobs 1325, according to an illustrative embodiment of the invention. With the flaps 1355a and 1355b resting on the knobs 1325, a space can be created such that air can be flowed into a bottom of the dock incubator 1300 and circulated around the side flaps.

Figure 14A:
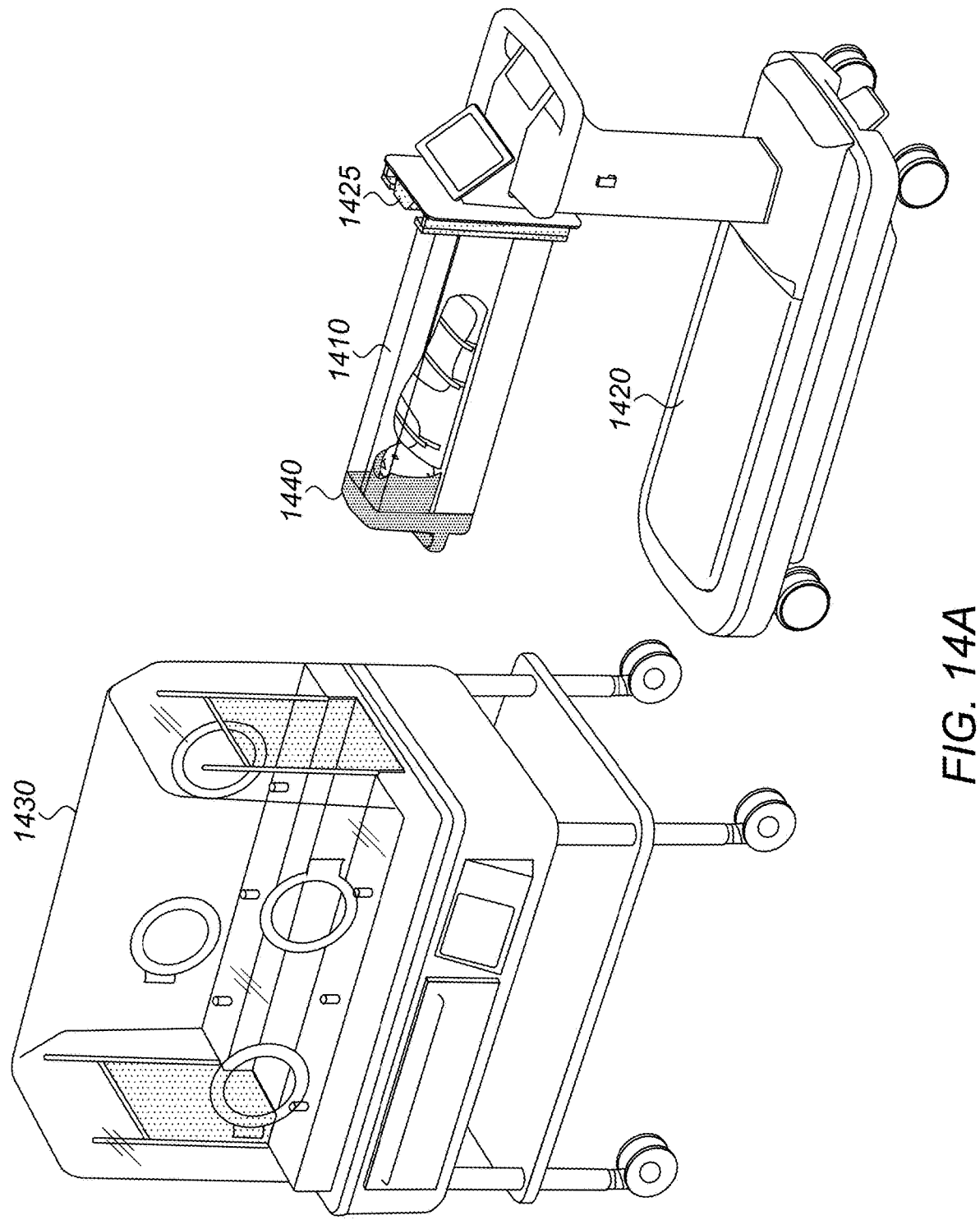
FIGS. 14A-14I are diagrams of a capsule incubator docking in a dock incubator, according to illustrative embodiments of the invention.

FIGS. 14A-14I are diagrams of a capsule incubator docking in a dock incubator, according to illustrative embodiments of the invention. In particular, the figures show a progression from the capsule incubator attached to a cart to the capsule incubator being docked within a docking incubator. FIG. 14A shows a capsule incubator 1410 coupled to a cart 1420 via a RF shielding structure 1425 and a dock incubator 1430. A radio frequency coil positioning system 1440 is coupled to the capsule incubator 1410.

Figure 14B:
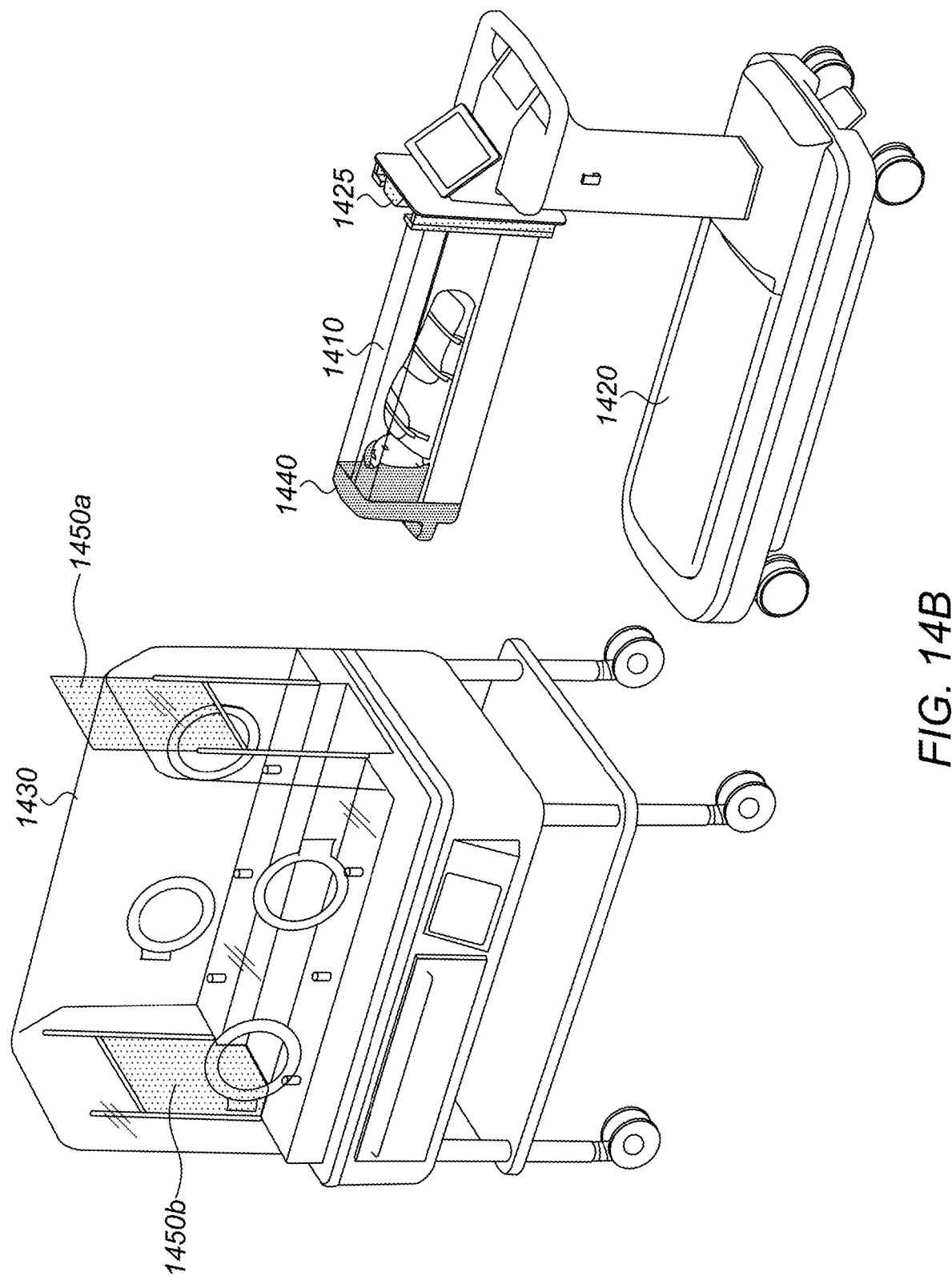
Figure 14C:
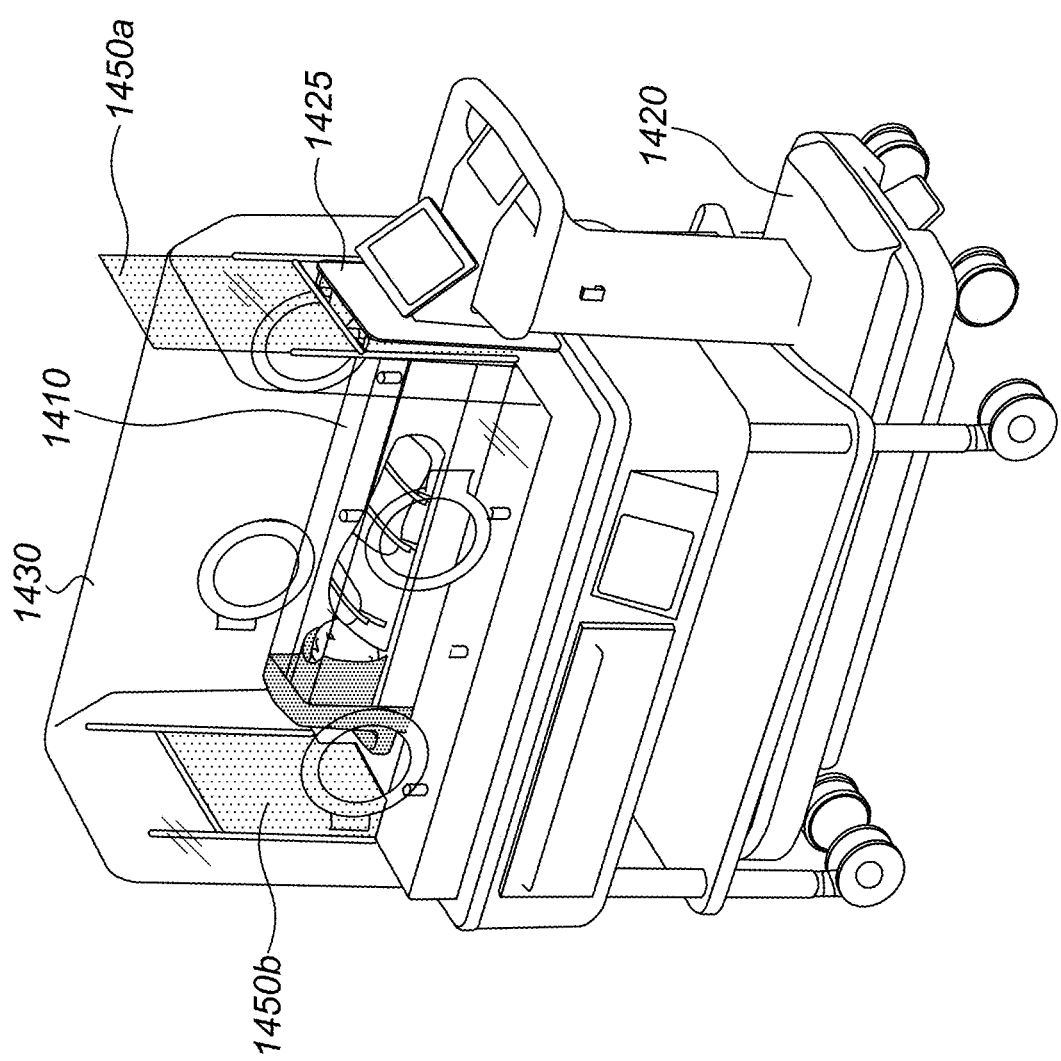
Figure 14D:
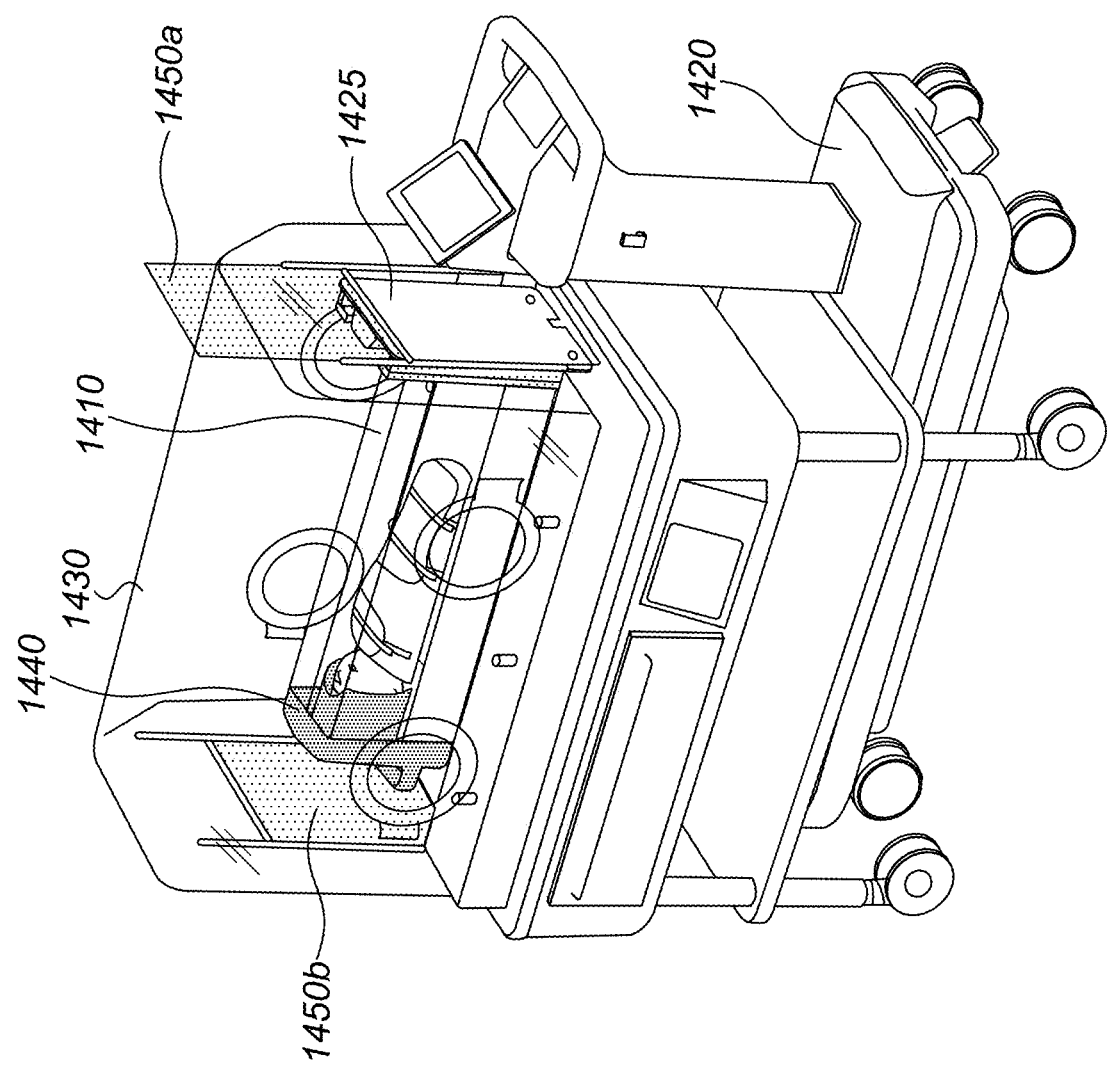
Figure 14E:
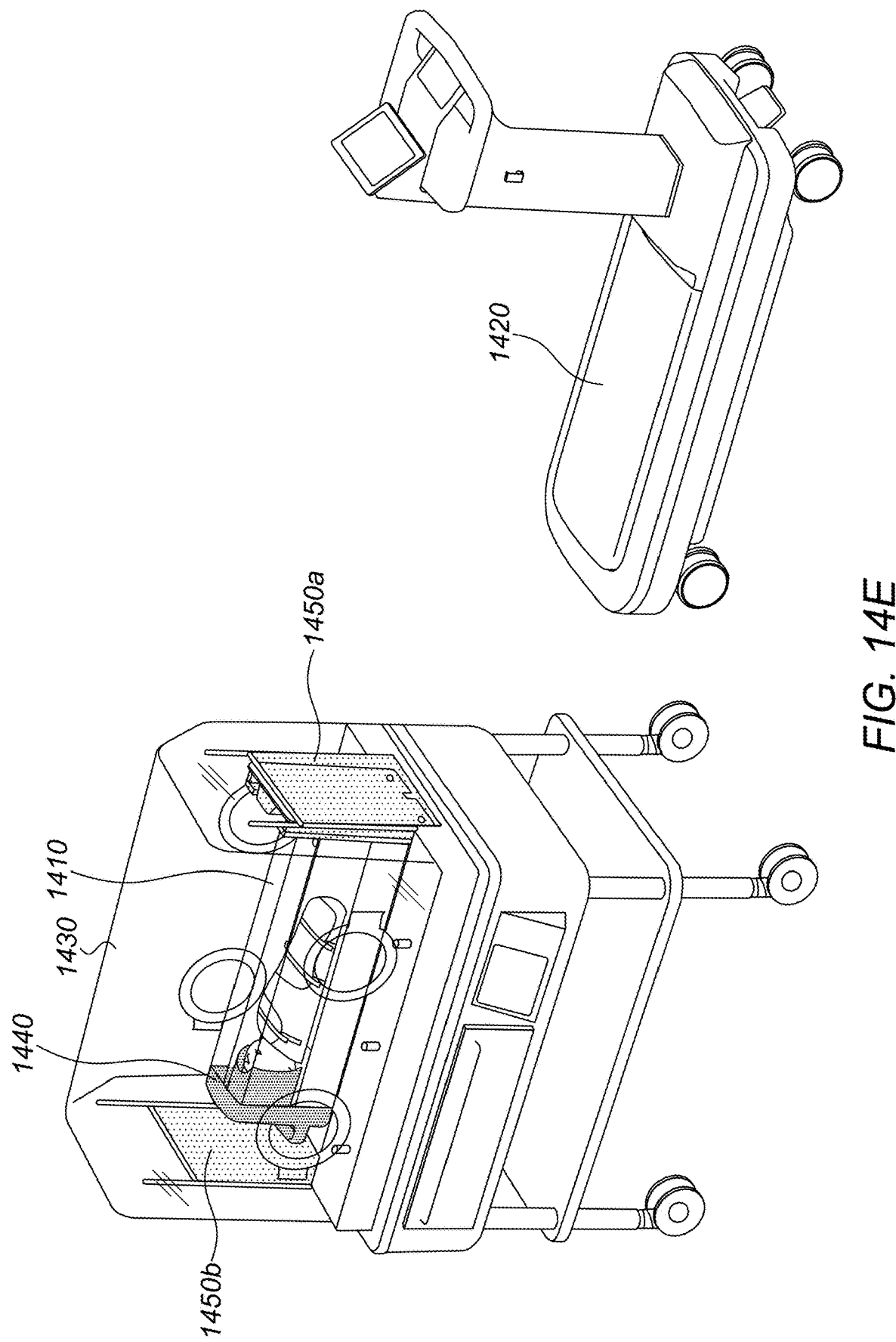

FIG. 14B shows the dock incubator 1430 having a first door 1450a and a second door 1450b. The first door 1450a is open. FIG. 14C shows the capsule incubator 1410 inserted through the first door 1450a via the cart 1420. FIG. 14D shows the cart 1420 detached from the capsule incubator 1410 as the capsule incubator 1410 is docked within the docking incubator 1430. FIG. 14E shows cart 1420 moved away from the docking incubator 1430, the first door 1450a is closed, and the capsule incubator 1410 is docked within the docking incubator 1430.

Figure 14F:
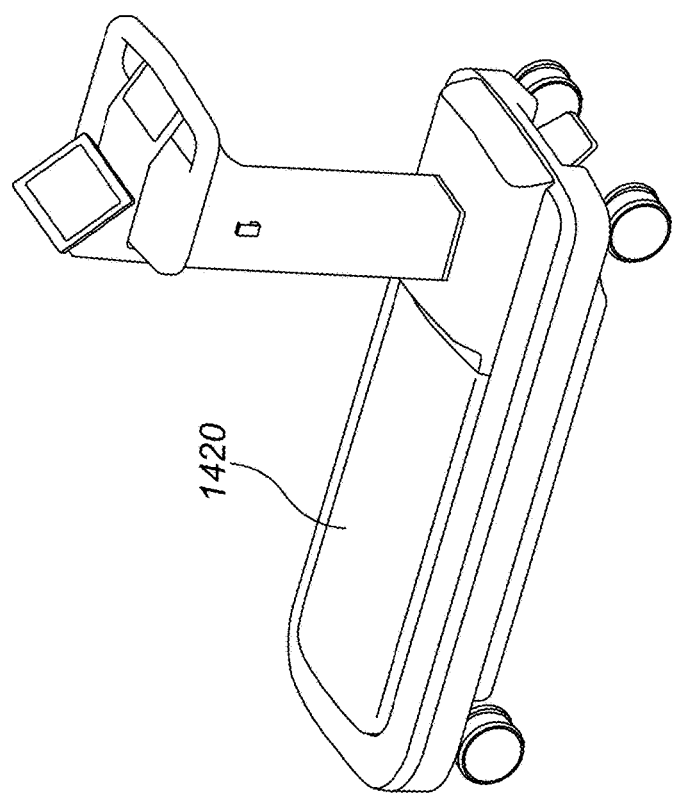
Figure 14F:
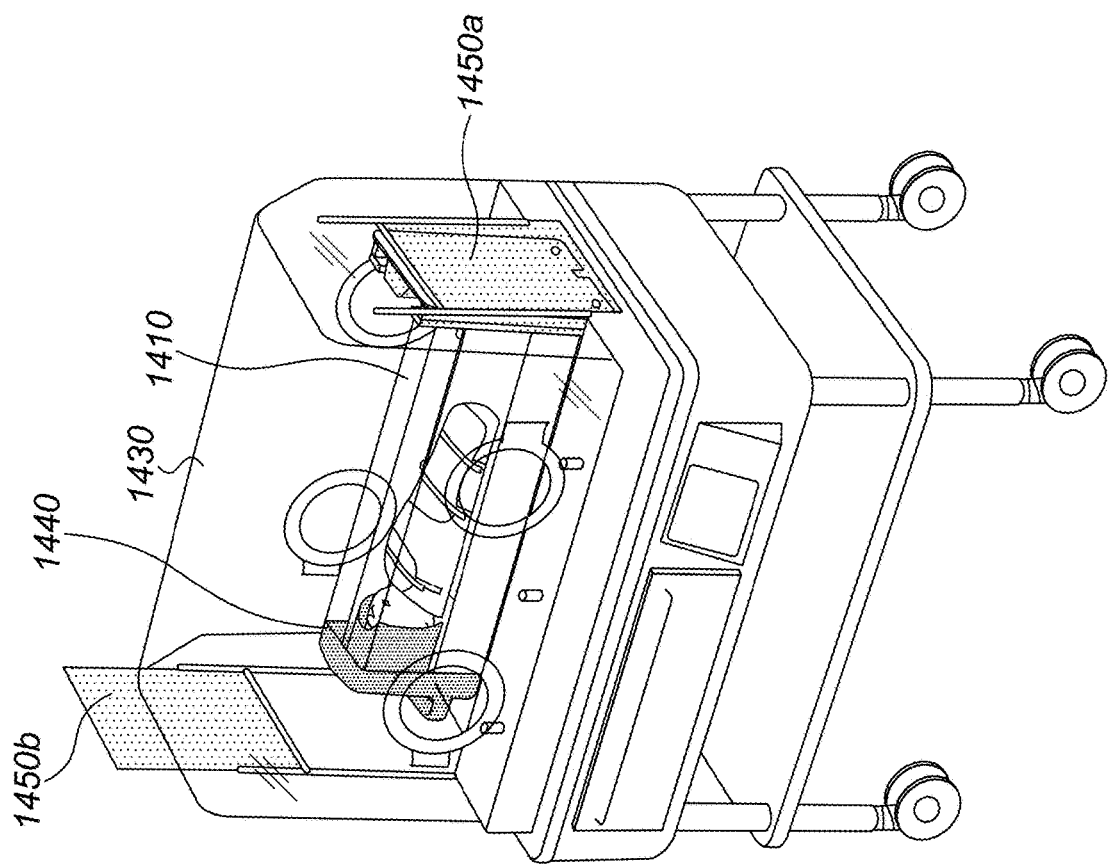

FIG. 14F shows a second door 1450b of the docking incubator 1430 open. FIG. 14G shows that the RF coil positioning system 1440 is removed. The RF coil positioning system 1440 can be removed through the second door 1450b. In some embodiments, the capsule incubator 1410 is inserted into the docking incubator 1430 through the second door 1450b, and the RF coil positioning system 1440 is removed through the first door 1450a. In some embodiments, the first and/or second doors, 1450a, and 1450b, respectively, are used to remove a body RF coil from the baby.

Figure 14H:
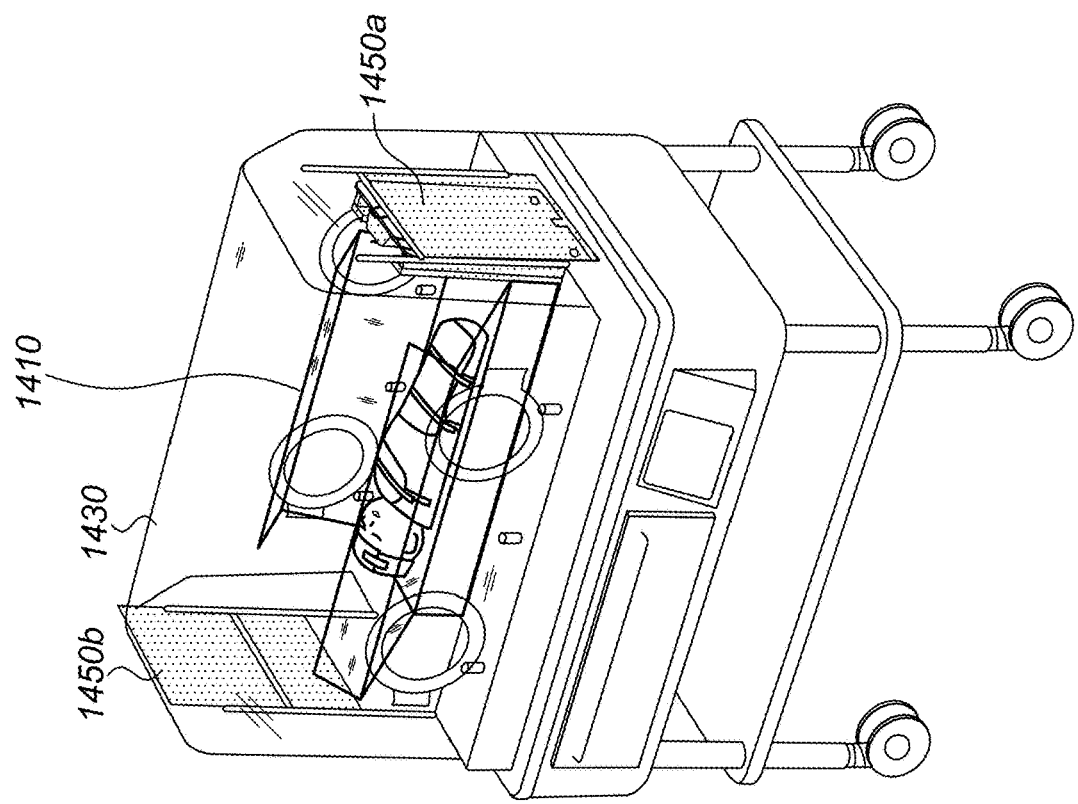
Figure 14G:
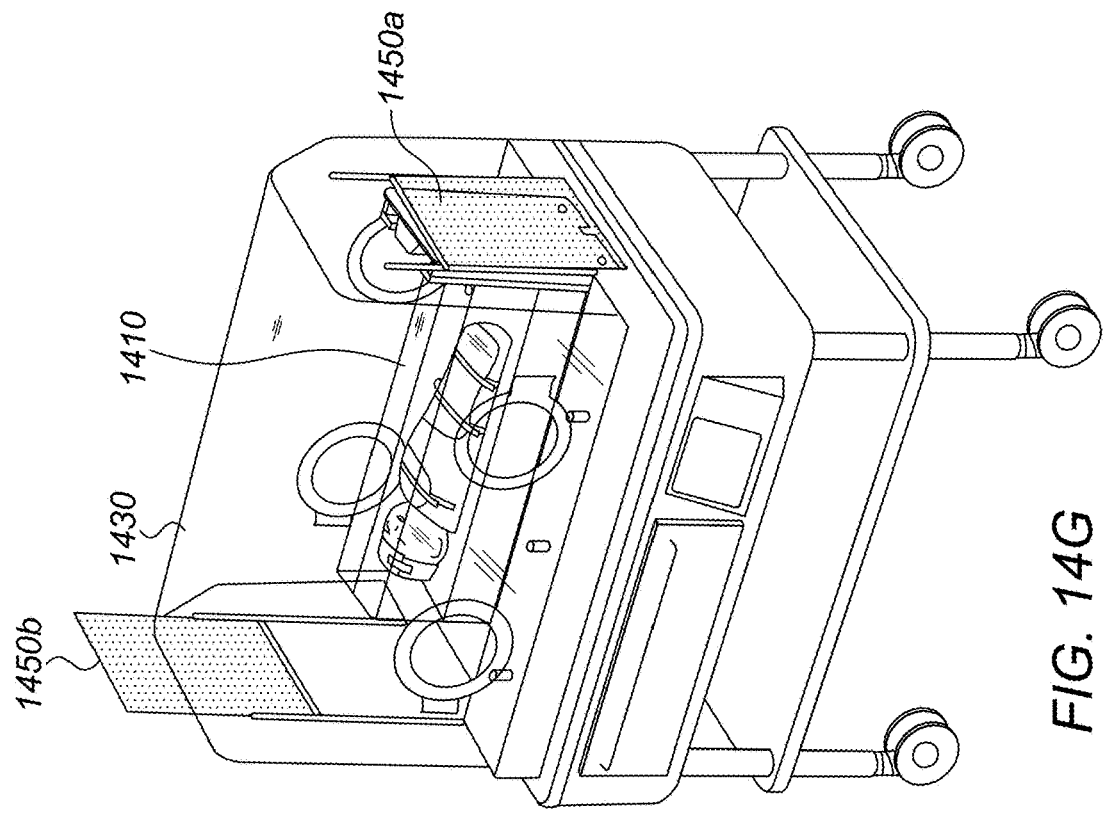
Figure 14I:
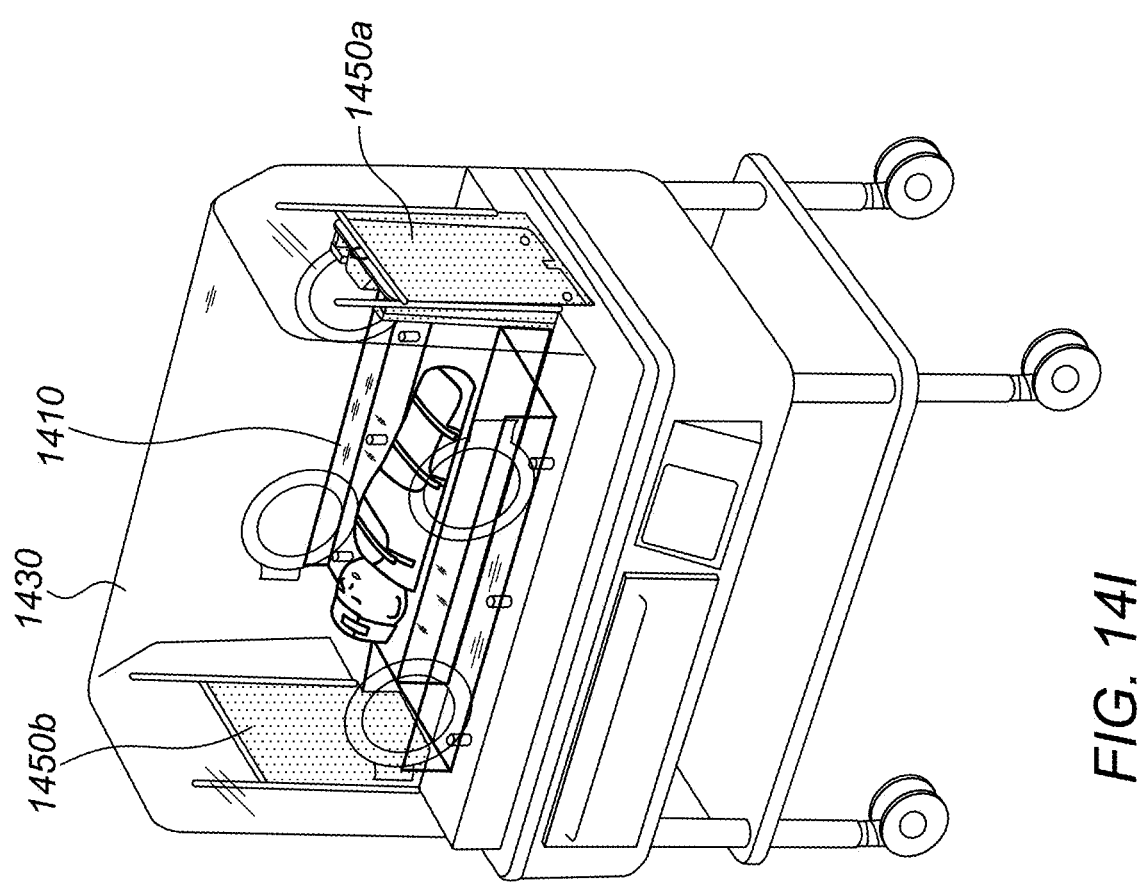

FIG. 14H shows the second door 1450b closing, and flaps of the capsule incubator 1410 opening. FIG. 14I shows the second door 1450 closed and the flaps of the capsule incubator 1410 fully open.

While FIGS. 14A-I show the progression of the capsule incubator being docked within the docking incubator, it is apparent to one of ordinary skill, that the reverse progression is also within the scope of the invention. For example, while the capsule incubator is docked within the docking station and the flaps of the capsule incubator are open, the flaps of the capsule incubator can close, a first door of the docking incubator can open, a RF coil can be positioned on the baby (e.g., the RF coil positioning or a body RF coil), the capsule incubator can be plugged (e.g., via the RF coil assembly or another plug as described above), a second door of the docking incubator can open, the cart can be pushed to the docking incubator such that the RF shielding structure couples to the cart (e.g., via a connector or directly to the cart itself), the cart can move away from the docking incubator with the capsule incubator attached, and the second door of the docking incubator can close. With the capsule incubator attached to the cart, the capsule incubator can transport the baby to a MRI device, or any location as described above.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the foregoing detailed description, numerous specific details are set forth in order to provide an understanding of the invention. However, it will be understood by those skilled in the art that the invention can be practiced without these specific details. In other instances, well-known methods, procedures, and components, modules, units and/or circuits have not been described in detail so as not to obscure the invention. Some features or elements described with respect to one embodiment can be combined with features or elements described with respect to other embodiments.

Although embodiments of the invention are not limited in this regard, discussions utilizing terms such as, for example, "processing," "computing," "determining," "determining," "establishing", "analyzing", "checking", or the like, can refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that can store instructions to perform operations and/or processes. Although embodiments of the invention are not limited in this regard, the terms "plurality" and "a plurality" as used herein can include, for example, "multiple" or "two or more". The terms "plurality" or "a plurality" can be used throughout the specification to describe two or more components, devices, elements, units, parameters, or the like. The term set when used herein can include one or more items. Unless explicitly stated, the method embodiments described herein are not constrained to a particular order or sequence. Additionally, some of the described method embodiments or elements thereof can occur or be performed simultaneously, at the same point in time, or concurrently.

What is claimed is:

1. A capsule incubator comprising:
   a surface for positioning a neonate thereon, the surface having a width and length sufficient for positioning a human baby;
   at least one closing structure, the closing structure to create a housing for the human baby when in a closed position and to create access to the human baby when in an open position;
   at least one coupling structure, to couple the capsule incubator to a cart; and a radio frequency (RF) shielding structure configured to plug an end of the capsule incubator when the at least one closing structure is in the closed position, the RF shield structure comprising a conduit having a first aperture and a second aperture, wherein the first aperture provides access to an exterior environment and the second aperture provides access to the interior of the capsule incubator when the closing structure is in a closed position, and wherein the conduit has a length to width ratio of at least 5 to 1, such that RF leakage through the conduit with respect to the exterior environment and the interior of the capsule incubator is substantially prevented.

2. A radio frequency (RF) shielding structure configured to plug an end of a capsule incubator designed to be inserted into the bore of an MRI device, the RF shielding structure comprising:
   a first surface having a RF shield, wherein:
      the first surface is adapted to mate with at least a portion of one or more walls of the capsule incubator, and
      the RF shield comprises a material such that when the portion of the one or more walls of the capsule incubator are mated to the first surface and the capsule incubator is inserted into the bore of the MRI device, the RF shield is operable to provide RF shielding between an interior and exterior environment of the MRI device; and
   a second surface that together with the first surface at last partially define a conduit having a first aperture and a second aperture, wherein:
      the first aperture provides access to the exterior environment of the MRI device,
      the second aperture provides access to the interior of the capsule incubator when the portion of the one or more walls of the capsule incubator are mated to the first surface,
      the conduit is configured to support one or more tubes for medical or life support equipment, and
      the conduit has a length-to-width ratio of at least 5-to-1 such that RF leakage through the conduit with respect to the exterior environment of the MRI device and the interior of the capsule incubator is substantially prevented.

3. The RF shielding structure of claim 2, wherein:
   the first surface further includes a protruding portion that is configured to mate with the portion of the one or more walls of the capsule incubator, and
   the RF shield is located adjacent to the protruding portion.

4. The RF shielding structure of claim 3, wherein an outside surface of the protruding portion is configured to mate with an inside surface of the portion of the one or more walls of the capsule incubator.

5. The RF shielding structure of claim 3, wherein the second aperture is defined at least in part by the protruding portion.

6. The RF shielding structure of claim 5, wherein the second aperture is defined at least in part by an outside surface of the protruding portion and the first surface.

* * * * *